(12) United States Patent
Li et al.

(10) Patent No.: US 9,695,395 B2
(45) Date of Patent: Jul. 4, 2017

(54) GENERATION AND MAINTENANCE OF STEM CELLS

(71) Applicant: The Scripps Research Institute, La Jolla, CA (US)

(72) Inventors: Wenlin Li, Shanghai (CN); Sheng Ding, Orinda, CA (US)

(73) Assignee: The Scripps Research Institute, La Jolla, CA (US)

( * ) Notice: Subject to any disclaimer, the term of this patent is extended or adjusted under 35 U.S.C. 154(b) by 118 days.

(21) Appl. No.: 14/490,433

(22) Filed: Sep. 18, 2014

(65) Prior Publication Data
US 2015/0079675 A1   Mar. 19, 2015

Related U.S. Application Data

(63) Continuation of application No. 13/140,108, filed as application No. PCT/US2009/068274 on Dec. 16, 2009, now Pat. No. 8,906,677.

(60) Provisional application No. 61/138,407, filed on Dec. 17, 2008.

(51) Int. Cl.
C12N 5/00       (2006.01)
C12N 5/0735    (2010.01)
C12N 5/074     (2010.01)

(52) U.S. Cl.
CPC ......... *C12N 5/0606* (2013.01); *C12N 5/0696* (2013.01); *C12N 2501/115* (2013.01); *C12N 2501/16* (2013.01); *C12N 2501/235* (2013.01); *C12N 2501/2306* (2013.01); *C12N 2501/602* (2013.01); *C12N 2501/603* (2013.01); *C12N 2501/604* (2013.01); *C12N 2501/727* (2013.01); *C12N 2510/00* (2013.01)

(58) Field of Classification Search
CPC .............................. C12N 5/0605; C12N 5/0696
See application file for complete search history.

(56) References Cited

U.S. PATENT DOCUMENTS

| 5,824,837 | A  | 10/1998 | Chen et al. |
| 5,843,780 | A  | 12/1998 | Thomson |
| 6,200,806 | B1 | 3/2001  | Thomson |
| 7,029,913 | B2 | 4/2006  | Thomson |
| 7,265,138 | B2 | 9/2007  | Doherty et al. |
| 8,298,825 | B1 | 10/2012 | Hochedlinger et al. |
| 8,603,818 | B1 | 12/2013 | Hochedlinger et al. |
| 8,906,677 | B2 | 12/2014 | Li et al. |
| 2002/0142457 | A1 | 10/2002 | Umezawa et al. |
| 2004/0157324 | A1 | 8/2004  | Spradling et al. |
| 2006/0182724 | A1 | 8/2006  | Riordan |
| 2007/0032447 | A1 | 2/2007  | Eilertsen |
| 2007/0128719 | A1 | 6/2007  | Tseng et al. |
| 2007/0134215 | A1 | 6/2007  | Fukuda et al. |
| 2007/0141703 | A1 | 6/2007  | Stanley et al. |
| 2007/0161107 | A1 | 7/2007  | Mummery et al. |
| 2007/0172946 | A1 | 7/2007  | Smith et al. |
| 2007/0196919 | A1 | 8/2007  | Reh et al. |
| 2007/0254359 | A1 | 11/2007 | Rezania et al. |
| 2007/0259423 | A1 | 11/2007 | Odorico et al. |
| 2007/0264709 | A1 | 11/2007 | Smith et al. |
| 2007/0269412 | A1 | 11/2007 | Kopyov |
| 2007/0281355 | A1 | 12/2007 | Dalton et al. |
| 2008/0066197 | A1 | 3/2008  | Ying et al. |
| 2008/0242594 | A1 | 10/2008 | McKay et al. |
| 2008/0268533 | A1 | 10/2008 | Dalton et al. |
| 2009/0068742 | A1 | 3/2009  | Yamanaka |
| 2009/0117439 | A1 | 5/2009  | Fujinami et al. |
| 2009/0203690 | A1 | 8/2009  | Akritopoulou-Zanze et al. |
| 2009/0227032 | A1 | 9/2009  | Yamanaka et al. |
| 2010/0233804 | A1 | 9/2010  | Zhou et al. |
| 2010/0267141 | A1 | 10/2010 | Shi et al. |
| 2011/0033931 | A1 | 2/2011  | Schwartz et al. |
| 2011/0039332 | A1 | 2/2011  | Sakurada et al. |
| 2012/0122212 | A1 | 5/2012  | Grskovic et al. |
| 2012/0129172 | A1 | 5/2012  | Okano et al. |
| 2012/0196360 | A1 | 8/2012  | Okita et al. |
| 2013/0323833 | A1 | 12/2013 | Zhu et al. |

FOREIGN PATENT DOCUMENTS

| CN | 101356270 A1 | 1/2009 |
| EP | 1970446 A1   | 9/2008 |
| GB | 2 436 737    | 10/2007 |
| GB | 2 450 603 A  | 12/2008 |
| JP | 2007/508026  | 4/2007 |
| JP | 2008/307007  | 12/2008 |
| JP | 2010/529851  | 9/2010 |
| WO | 03/095628 A2 | 11/2003 |
| WO | 2007/016566 A2 | 2/2007 |
| WO | 2007/069666 | 6/2007 |
| WO | 2007/113505 | 10/2007 |
| WO | 2008/015418 A2 | 2/2008 |
| WO | 2008/056173 A2 | 5/2008 |
| WO | 2008/088882 | 7/2008 |
| WO | 2008/089351 | 7/2008 |
| WO | 2008/105630 A1 | 9/2008 |
| WO | 2009/006422 A1 | 1/2009 |
| WO | 2009/032194 A1 | 3/2009 |
| WO | 2009/032456 A1 | 3/2009 |
| WO | 2009/057831 | 5/2009 |
| WO | 2009/067756 A1 | 6/2009 |
| WO | 2009/067757 A1 | 6/2009 |
| WO | 2009/073523 A2 | 6/2009 |
| WO | 2009/117439 A1 | 9/2009 |
| WO | 2011/047300 A1 | 4/2011 |
| WO | 2011/109695 A1 | 9/2011 |

OTHER PUBLICATIONS

Office Action mailed Sep. 25, 2015; U.S. Appl. No. 12/933,391.
(Continued)

*Primary Examiner* — Marcia S Noble
(74) *Attorney, Agent, or Firm* — Kilpatrick Townsend & Stockton LLP

(57) ABSTRACT

The present invention provides for the generation and maintenance of pluripotent cells by culturing the cells in the presence of an ALK5 inhibitor.

22 Claims, 16 Drawing Sheets
(3 of 16 Drawing Sheet(s) Filed in Color)

(56) References Cited

OTHER PUBLICATIONS

Egler et al., "Histone Deacetylase Inhibition and Blockade of the Glycolytic Pathway Synergistically Induce Glioblastoma Cell Death," Clin. Cancer Res., 2008, vol. 14(10), pp. 3132-3140.
Engel et al., "Allosteric activation of the protein kinase PDK1 with low molecular weight compounds," The EMBO Journal, 2006, vol. 25, pp. 5469-5480.
Gonzalez et al., "Generation of mouse-induced pluripotent stem cells by transient expression of a single nonviral polycistronic vector," PNAS, Jun. 2009, vol. 106(22), pp. 8918-8922.
Pesce et al., "Differential expression of the Oct-4 transcription factor during mouse germ cell differentiation," Mechanisms of Development, 1998, vol. 71, pp. 89-98.
Wang et al., "The Immunophilin FKBP12 Functions as a Common Inhibitor of the TGFβ Family Type 1 Receptors," Cell, Aug. 1996, vol. 86, pp. 435-444.
Watanabe et al., "Activation of Akt signaling is sufficient to maintain pluripotency in mouse and primate embryonic stem cells," Oncogene, 2006, vol. 25, pp. 2697-2707.
Zhao et al., "Resorcylic Acid Lactones: Naturally Occurring Potent and Selective Inhibitors of MEK," The Journal of Antibiotics, Dec. 1999, vol. 52(12), pp. 1086-1094.
Aasen et al., Nat Biotechnol 26:1276-1284 (2008).
Aoi et al., "Generation of Pluripotent Stem Cells from Adult Mouse Liver and Stomach Cells," Sciencexpress, Feb. 2008, DOI 10.1126/science.1154884, 8 pages.
Artyomov et al., PLoS Comput Biol 6, e1000785 (2010).
Beaujean et al., Dev. Biol., 2000, vol. 221, pp. 337-354.
Brambrink et al., Cell Stem Cell 2, 151-9 (2008).
Brons et al., Nature, 2007, vol. 448, pp. 191-195.
Chambers et al., Nature, 2007, vol. 450, pp. 1230-1234.
Chen et al., "Self-renewal of embryonic stem cells by a small molecule," PNAS, 103(46):17266-17271, 2006.
Chen et al., Proc Natl Acad Sci USA, 2007, vol. 104, pp. 10482-10487.
Chou et al., Cell, 2008, vol. 135, pp. 449-461.
Christen et al., BMC Biol 8, 5 (2010).
Claassen et al., "ROCK inhibition enhances the recovery and growth of cryopreserved human embryonic stem cells and human induced pluripotent stem cells," Molecular Reproduction and Developments, 2009, vol. 76, No. 8, pp. 722-732.
Collas et al., Reproductive BioMedicine Online: 762-770, 2006.
D'Amour et al., Nat Biotechnol, 2005, vol. 23, pp. 1534-1541.
Debs et al., J. Biol. Chem., 1990, vol. 265, pp. 10189-10192.
Demers et al., Cloning Stem Cells, 2007, vol. 9, pp. 512-522.
Dimos et al., Science, 2008, vol. 321, pp. 1218-1221.
Djuric et al., 202, Stem Cell Research and Therapy, 2010, 1:3.
Dvorak et al., Stem Cells, 2005, vol. 23, pp. 1200-1211.
Ernst et al., "gp130-mediated Signal Transduction in Embryonic Stem Cells Involves Activation of Jak and Ras/Mitogen-activated Protein Kinase Pathways," J. Biol. Chem., Nov. 22, 1996, vol. 271, No. 47, pp. 30163-30143.
Feldman et al., "G9a-mediated irreversible epigenetic inactivation of Oct-3/4 during early embryogenesis," Nature Cell Biology, 2006, vol. 8(2), pp. 188-194.
Feng et al, "Molecules that Promote or Enhance Reprogramming of Somatic Cells to Induced Pluripotent Stem Cells," Cell Stem Cell, 2009, 4, 301-12.
Graf et al., Nature 462(7273):587-594 (2009).
Guo et al., Development, 2009, vol. 136, pp. 1063-1069.
Hakelien et al., "Transient alteration of cell fate using a nuclear and cytoplasmic extract of an insulinoma cell line," BBRC, vol. 316, pp. 834-841.
Han et al., Curr Stem Cell Res Ther, 2008, vol. 3, pp. 66-74.
Han et al., Nat Cell Biol 13(1):66-71 (2011).
Hanna et al., Cell 133, 250-64.
Hanna et al., Nature 462, 595-601 (2009).

Hanna et al, "Treatment of Sickle Cell Anemia Mouse Model with iPS Cells Generated from Autologous Skin," Science, Dec. 21, 2007, vol. 318, pp. 1920-1922.
Hayashi et al., Cell Stem Cell, 2008, vol. 3, pp. 391-401.
Hindie et al., Structure and allosteric effects of low-molecular-weight activators on the protein kinase PDK1, Nat. Chem Biol., Oct. 2009, vol. 5, No. 10, pp. 758-764.
Ho et al., Cancer Res., 2001, vol. 61, pp. 474-477.
Hochedlinger et al., Development 136, 509-23 (2009).
Hochedlinger, et al., "Nuclear reprogramming and pluripotency," Nature, Jun. 2006, vol. 441, pp. 1061-1067.
Huangfu et al., Induction of pluripotent stem cells by defined factors is greatly improved by small-molecule compounds, Nature Biotechnology, 2008, vol. 26, pp. 795-797 (last name mb Danwei).
Huangfu et al., "Induction of pluripotent stem cells from primary human fibroblasts with only Oct4 and Sox2," 2008, Nature Biotechnology, 26:11, pp. 1269-1275.
Hudecz et al., Medicinal Research Reviews, 25(6): 679-736, 2005.
Ieda et al., Cell 142, 375-86 (2010).
Jia et al., Nat Methods 7(3):197-199 (2010).
Kanatsu-Shinohara et al., Cell, 2004, vol. 119, pp. 1001-1012.
Kim et al., Cell, 2009, vol. 136, pp. 411-419.
Kim et al., Cell Stem Cell, 4(6):472-476, 2009.
Kim et al., "Direct reprogramming of mouse fibroblasts to neural progenitors," Proc. Natl. Acad. Sci., USA, May 10, 2011, vol. 108, No. 9, pp. 7838-7843.
Krippl et al., Proc. Natl. Acad. Sci. USA, 1984, vol. 81, pp. 6988-6992.
Kubicek, et al., "Reversal of H3K9me2 by a Small-Molecule Inhibitor for the G9a Histone Methyltransferase," Molecular Cell, Feb. 2007, vol. 25, No. 3, pp. 473-481.
Kuzmenkin et al., FASEB J. 23, 4168-80 (2009).
Li et al., "Generation of rat and human induced pluripotent stem cells by combining genetic reprogramming and chemical inhibitors," Cell Stem Cell, 2009, vol. 4, pp. 16-19 (Last Name MB Wenlin).
Li et al., Differentiation, 2007, vol. 75, pp. 299-307.
Li et al., "Small molecules that modulate embryonic stem cell fate and somatic cell reprogramming," Trends Pharmacol Sci, Jan. 2010, vol. 31, No. 1, pp. 36-45.
Li et al., "Generation of Human-Induced Pluripotent Stem Cells in the Absence of Exogenous Sox2," Stem Cells 27:2992-3000 (2009).
Lin et al., Nat Methods 6:805-808 (2009).
Lin et al., Nat Methods 6:805-808 (2009), Supplemental Information, 7 pages.
Lowry et al., Proc Natl Acad Sci USA, 2008, vol. 105, pp. 2883-2888.
Maherali et al., "Directly Reprogrammed Fibroblasts Show Global Epigenetic Remodeling and Widespread Tissue Contribution," Cell Stem Cell, 2007, 1, pp. 55-70.
Maherali et al., "Tgfβ Signal Inhibition Cooperates in the Induction of iPSCs and Replaces Sox2 and cMyc," Current Biology, 2009, vol. 19, pp. 1718-1723.
Meissner, et al., "Direct reprogramming of genetically unmodified fibroblasts into pluripotent stem cells," Nature Biotechnology, Oct. 2007, vol. 25, No. 10, pp. 1177-1181.
Mi et al., Mol. Ther., 2001, vol. 4, pp. 339-347.
Mikkelsen et al., Nature 454(7200):49-55 (2008).
Muller et al., "Upping the Ante: Recent Advances in Direct Reprogramming," Mol. Ther., 2009, vol. 17, pp. 947-953.
Nakagawa et al., Nat Biotechnol, 2008, vol. 26, pp. 101-106.
Noggle et al., "A Molecular Basis for Human Embryonic Stem Cell Pluripotency," Stem Cell Reviews and Reports, Jan. 2005, vol. 1(2), pp. 1550-8943; DOI: 10.1385/scr:1:2:111.
Okada et al., Biochem Biophys Acta 1800, 956-63 (2010).
Okita et al., Nature 448, 313-317 (2007).
Okita et al., Science 322:949-953, 2008.
Oliver! et al., Regenerative Medicine, 2(5): 795-816, Sep. 2007.
Pan et al., J. Biol. Chem., 2004, vol. 279, pp. 37013-37020.
Peerani et al., EMBO J., 2007, vol. 26, pp. 4744-4755.
Plath et al., Nature Reviews, 12: 253-265, 2011.

(56) References Cited

OTHER PUBLICATIONS

Plews, et al., "Activation of Pluripotency Genes in Human Fibroblast Cells by a Novel mRNA Based Approach," PLoS ONE, Dec. 2010, vol. 5, No. 12, pp. 1-10.
Roberts et al., (PD98059 Enhanced Insulin, Cytokine, and Growth Factor Activation of Xanthine Oxidoreductase in Epithelial Cells Involves STAT3 and the Glucocoticoid Receptor, Journal of Cellular Biochemistry 2007, 101: 1567-1587.
Ruhnke et al., Stem Cells, 2003, vol. 21, pp. 428-436.
Saha et al., Biophys. J., 2008, vol. 94, pp. 4123-4133.
Sato et al., Dev. Biol., 2003, vol. 260, pp. 404-413.
Schenke-Layland et al., Stem Cell 26, 1537-46 (2008).
Schugar et al., Gene Ther, 2008, vol. 15, pp. 126-135.
Schulze et al., Methods Mol Biol, 2006, vol. 329, pp. 45-58.
Sells et al., BioTechniques, 1995, vol. 19, pp. 72-78.
Shi, et al., "A Combined Chemical and Genetic Approach for the Generation of Induced Pluripotent Stem Cells," Cell Stem Cell, Jun. 2008, vol. 2, No. 6, pp. 525-528.
Shi "Induction of Pluripotent Stem Cells from Mouse Embryonic Fibroblasts by Oct4 and Klf4 with Small-Molecule Compounds," Cell Stem Cell, 2008, vol. 3, pp. 568-574.
Shields et al., J. Biol. Chem., 1997, vol. 272, pp. 18504-18507.
Silva et al., Cell 138, 722-37 (2009).
Silva et al., PLoS Biology, 6(10): 2237-2247, Oct. 2008.
Singh et al., Stem Cells, 2007, vol. 25, pp. 2534-2542.
Sridharan et al., Cell 136(2):364-377 (2009).
Stacey et al., Mol. Cell. Biol., 1987, vol. 7, pp. 523-527.
Stadtfeld et al., "Reprogramming of Pancreatic β Cells into Pluripotent Stem Cells," Curr. Biol., Jun. 2008, vol. 18(12): 890, doi: 10.1016/j.cub.2008.05.010.
Stadtfeld et al., Cell Stem Cell 2, 230-40 (2008).
Stadtfeld et al., Nat Methods 7, 53-55 (2010).
Stadtfeld et al., Science 322:945-949, 2008.
Sullivan et al., Reproductive BioMed. Online, 16(1): 41-50, Nov. 2008.
Sylvester et al. (Arch Surg. 136:93-99, 2004).
Szabo et al., Nature 468(7323):521-526 (2010).
Tada, et al., "Nuclear reprogramming of somatic cells by in vitro hybridization with ES cells," Current Biology, 2001, vol. 11, pp. 1553-1558.
Takahashi, et al., "Induction of Pluripotent Stem Cells from Mouse Embryonic and Adult Fibroblast Cultures by Defined Factors," Cell, Aug. 2006, vol. 126, No. 4, pp. 663-676.
Takahashi et al.; "Induction of Pluripotent Stem Cells from Adult Human Fobroblasts by Defined Factors"; Cell, 2007, vol. 131, pp. 861-872.
Takahashi et al., Nat Protoc 2, 3081-9 (2007).
Taranger et al., "Induction of Dedifferentiation, Genomewide Transcriptional Programming, and Epigenetic Reprogramming by Extracts of Carcinoma and Embryonic Stem Cells," Molecular Biology of the Cell, 2005, vol. 16, pp. 5719-5735.
Tesar et al., Nature, 2007, vol. 448, pp. 196-199.
Tighe et al., BMC 8:34 doi//:www.biomedcentral.com/1471-2121/8/34, printout pp. 1-17.
Tojo, et al., "The ALK-5 inhibitor A-83-01 inhibits Smad signaling and epithelia-to-mesenchymal transition by transforming growth factor-β," Cancer Sci, Nov. 2005, vol. 96, No. 11, pp. 791-800.
Toyooka et al., Development, 2008, vol. 135, pp. 909-918.
Ueda et al., PLoS ONE 3, 2008, e2800.
Vallier et al., "Activin/Nodal and FGF pathways cooperate to maintain pluripotency of human embryonic stem cells," Journal of Cell Science, Oct. 2005, vol. 118(19), pp. 4495-4509, DOI: 10.1111/J.1432-0436.2006.00143.X.
Vierbuchen et al., "Direct conversion of fibroblasts to functional neurons by defined factors," Nature, Feb. 25, 2010, vol. 463, No. 7284, pp. 1035-1042.
Wadia et al., Curr. Opin. Biotechnol., 2002, vol. 13, pp. 52-56.
Warren et al., Cell Stem Cell 7(5):618-630 (2010).
Watanabe et al., "A ROCK inhibitor permits survival of dissociated human embryonic stem cells," Nature Biotechnology, 25(6):681-868, 2007.
Wenlin et al., "Generation of novel rat and human pluripotent stem cells by reprogramming and chemical approaches," Methods in Molecular Biology, Jan. 2010, vol. 636, pp. 293-300 (Last Name MB Li).
Wernig et al., Nat Biotechnol 26, 916-24 (2008).
Wering et al., "c-Myc is Dispensable for Direct Reprogramming of Mouse Fibroblasts," Cell Stem Cell, 2008, 2, 10-12.
Wernig, et al., "In vitro reprogramming of fibroblasts into a pluripotent ES-cell-like state," Nature, Jul. 2007, vol. 448, No. 7151, pp. 318-324.
Wu et al., "Cellular senescence is an important mechanism of tumor regression upon c-Myc inactivation," PNAS, 2007, vol. 104(32), pp. 13028-13033.
Xiong et al., "Histone deacetylase inhibitors DNA methyltransferase-3B messenger RNA stability and down-regulate de novo DNA methyltransferase activity in human endometrial cells," Cancer Res., Apr. 2005, vol. 65(7), pp. 2684-2689.
Xu et al., Nat. Biotechnol, 2002, vol. 20, pp. 1261-1264.
Xu et al., Nature 453, 338-44 (2008).
Xu et al., "Revealing a core signaling regulatory mechanism for pluripotent stem cell survival and self-renewal by small molecules," PNAS, 2010, vol. 107(8), pp. 8129-8134.
Yamanaka, S. Cell 126, 663-676 (2006).
Yamanaka, "Strategies and New Developments in the Generation of Patient-Specific Pluripotent Stem Cells," Cell Stem Cell, Jul. 2007, vol. 1, pp. 39-49.
Ying et al, Nature, 2008, vol. 453, pp. 519-523.
Ying et al., Cell, 2003, vol. 115, pp. 281-292.
Yu et al., Science, 2007, vol. 318, pp. 1917-1920.
Zhao et al., Cell Death and Differentiation, 2007, vol. 14, pp. 489-499.
Zheng et al., Cancer Res., 2003, vol. 63, pp. 6909-6913.
Zhou et al., "Conversion of Mouse Epiblast Stem Cells to an Earlier Pluripotency State by Small Molecules," Journal of Biological Chemistry, Sep. 2010, vol. 285(39), pp. 29676-29680; DOI: 10.1074/jbc.C110.150599.
Zhou et al., Nature 455(7213):627-632 (2008).
Zhou, Hongyan et al.; Generation of Induced Pluripotent Stem Cells Using Recombinant Proteins; Cell Stem Cell, 4: 381-384 (2009).
Zhu et al, "Reprogramming of human primary somatic cells by OCT4 and chemical compounds," Cell Stem Cell, Dec. 2010, vol. 7, No. 6, pp. 651-655.
Condorelli, G. et al., "Cardiomyocytes induce endothelial cells to trans-differentiate into cardiac muscle: Implications for myocardium regeneration," PNAS, vol. 98, No. 19, Sep. 11, 2001, pp. 10733-10738.
Dravida, S. et al., "The transdifferentiation potential of limbal fibroblast-like cells," Developmental Brain Research, vol. 160, No. 2, Dec. 7, 2005, pp. 239-251.
Efe, Jem E. et al., "Conversion of mouse fibroblasts into cardiomyocytes using a direct reprogramming strategy," Nature Cell Biology, vol. 13, No. 3, Mar. 1, 2011, pp. 215-222.
Kaji et al., "Virus free induction of pluripotency and subsequent excision of reprogramming factors," Nature, Apr. 2009, vol. 458(7239), pp. 771-775.
Kim et al., "Pluripotent stem cells induced from adult neural stem cells by reprogramming with two factors," 2008, Nature 454:646-651.
Loh et al., "Generation of induced pluripotent stem cells from human blood," Blood, May 2009, vol. 113(22), pp. 5476-5479.
Takei, Shunsuke et al., "Bone morphogenetic protein-4 promotes induction of cardiomyocytes from human embryonic stem cells in serum-based embryoid body development," AJP Heart and Circulatory Physiology, vol. 296, No. 6, Jun. 2009, pp. H1793-H1803.
Takeuchi, Jun K. et al., "Directed transdifferentiation of mouse mesoderm to heart tissue by defined factors," Nature, vol. 459, No. 7247, Jun. 4, 2009, pp. 708-711.

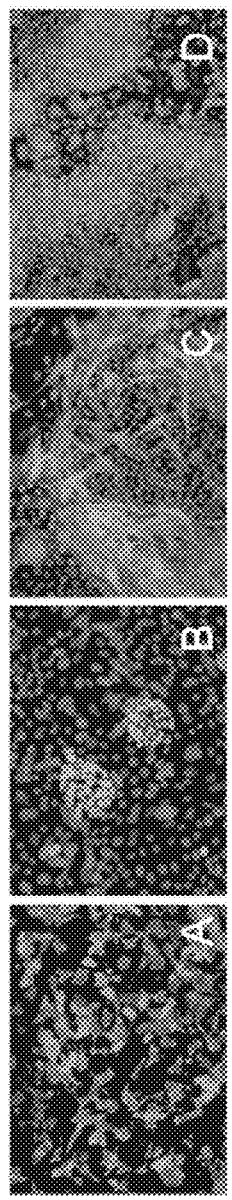
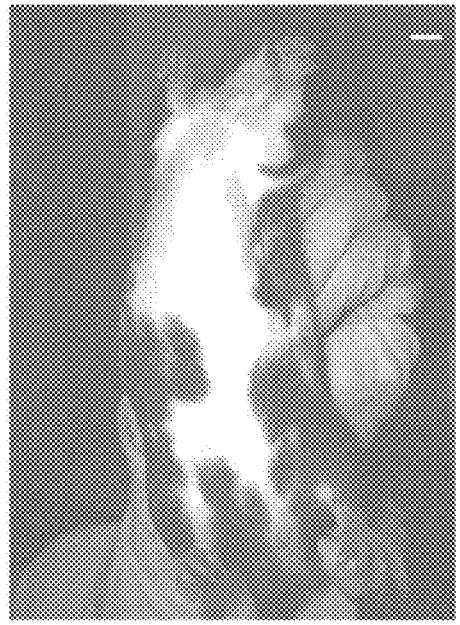
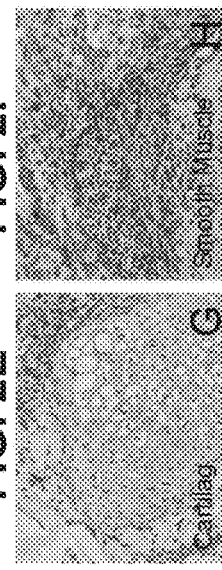

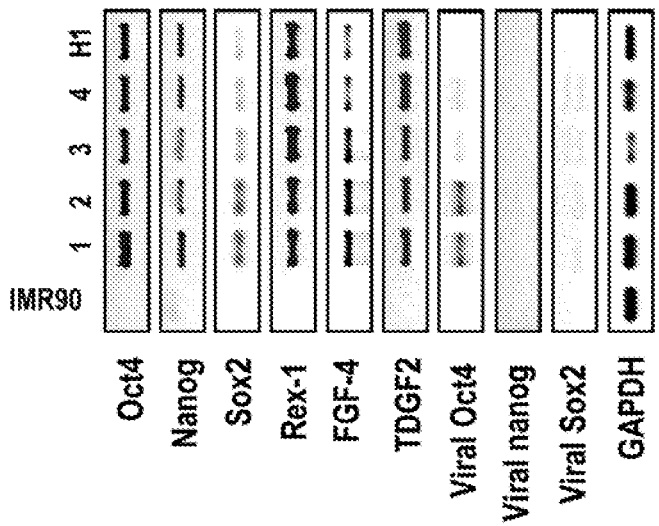
FIG. 3J
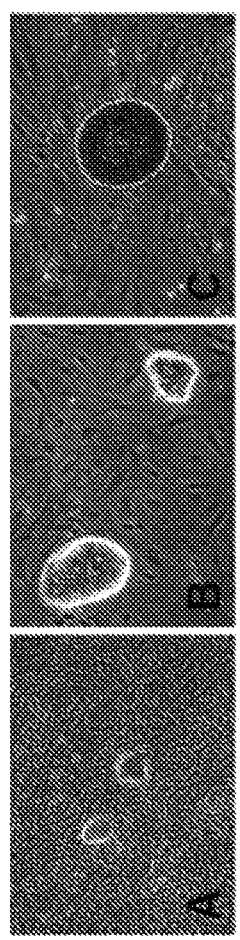
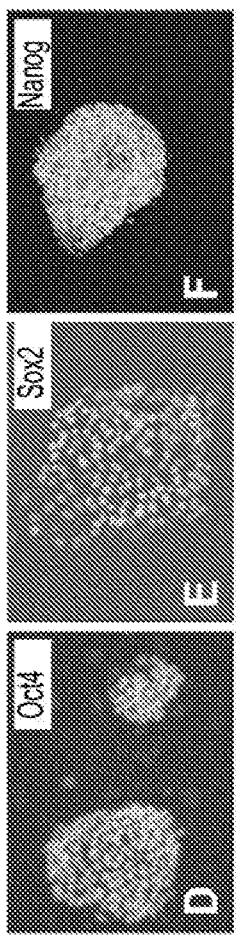
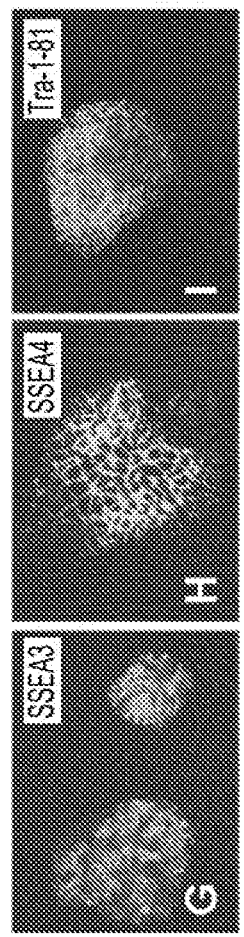

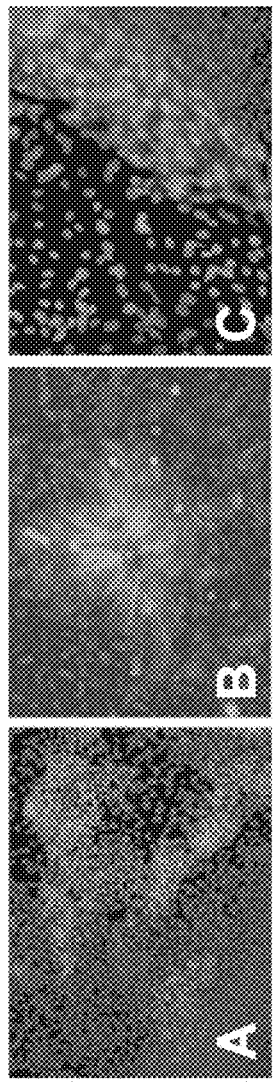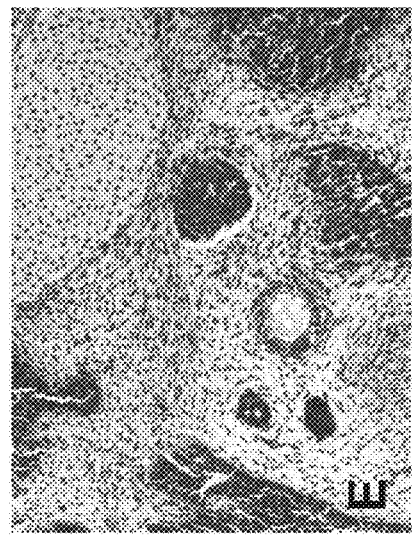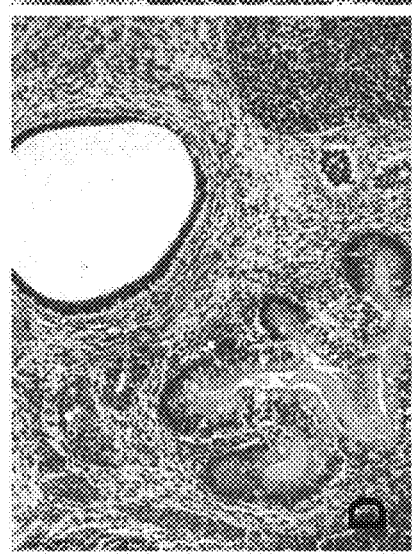
FIG. 4A  FIG. 4B  FIG. 4C  FIG. 4D  FIG. 4E

Efficiency of chimera generation

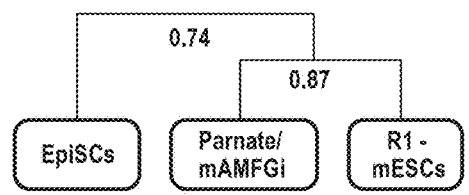
FIG. 8C
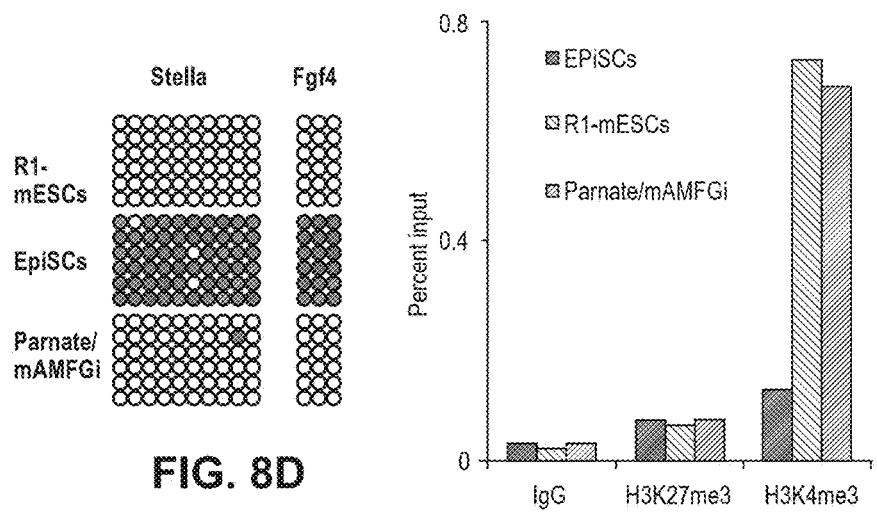
FIG. 8D
FIG. 8E

Summary of GFP genotyping

|  | Heart | Lung | Liver | Brain | Spleen |
|---|---|---|---|---|---|
| Chimera-1 | + | + | + | + | - |
| Chimera-2 | + | + | + | + | - |
| Chimera-3 | + | + | + | + | + |
| Chimera-4 | + | + | + | + | + |
| Chimera-5 | + | + | + | + | - |

SEQUENCE LISTING

```
<160> NUMBER OF SEQ ID NOS: 91

<210> SEQ ID NO 1
<211> LENGTH: 11
<212> TYPE: PRT
<213> ORGANISM: Artificial Sequence
<220> FEATURE:
<223> OTHER INFORMATION: synthetic GSK3 inhibitor L803, unmyristoylated
      GSK3beta Inhibitor XIII
<220> FEATURE:
<221> NAME/KEY: MOD_RES
<222> LOCATION: (10)...(10)
<223> OTHER INFORMATION: phosphoserine
<220> FEATURE:
<221> NAME/KEY: MOD_RES
<222> LOCATION: (11)...(11)
<223> OTHER INFORMATION: prolinamide

<400> SEQUENCE: 1

Lys Glu Ala Pro Pro Ala Pro Pro Gln Ser Pro
1               5                   10
```

-continued

<210> SEQ ID NO 2
<211> LENGTH: 17
<212> TYPE: DNA
<213> ORGANISM: Artificial Sequence
<220> FEATURE:
<223> OTHER INFORMATION: synthetic RT-PCR forward primer for rat Oct4

<400> SEQUENCE: 2
tactgcccgc cccagcg                                                    17

<210> SEQ ID NO 3
<211> LENGTH: 19
<212> TYPE: DNA
<213> ORGANISM: Artificial Sequence
<220> FEATURE:
<223> OTHER INFORMATION: synthetic RT-PCR reverse primer for rat Oct4

<400> SEQUENCE: 3
gctgcttggc aatgctagt                                                  19

<210> SEQ ID NO 4
<211> LENGTH: 20
<212> TYPE: DNA
<213> ORGANISM: Artificial Sequence
<220> FEATURE:
<223> OTHER INFORMATION: synthetic RT-PCR forward primer for rat Sox2

<400> SEQUENCE: 4
aaggccgtgc acgccgacga                                                 20

<210> SEQ ID NO 5
<211> LENGTH: 22
<212> TYPE: DNA
<213> ORGANISM: Artificial Sequence
<220> FEATURE:
<223> OTHER INFORMATION: synthetic RT-PCR reverse primer for rat Sox2

<400> SEQUENCE: 5
accacaccat gaaggcattc at                                              22

<210> SEQ ID NO 6
<211> LENGTH: 20
<212> TYPE: DNA
<213> ORGANISM: Artificial Sequence
<220> FEATURE:
<223> OTHER INFORMATION: synthetic RT-PCR forward primer for rat Nanog

<400> SEQUENCE: 6
tagccctgat tcttctagca                                                 20

<210> SEQ ID NO 7
<211> LENGTH: 20
<212> TYPE: DNA
<213> ORGANISM: Artificial Sequence
<220> FEATURE:
<223> OTHER INFORMATION: synthetic RT-PCR reverse primer for rat Nanog

<400> SEQUENCE: 7
tttgctgcaa cggcacataa                                                 20

<210> SEQ ID NO 8
<211> LENGTH: 20
<212> TYPE: DNA
<213> ORGANISM: Artificial Sequence
<220> FEATURE:
<223> OTHER INFORMATION: synthetic RT-PCR forward primer for rat Rex-1

-continued

<400> SEQUENCE: 8
aaatcatgac gaggcaaggc                                                  20

<210> SEQ ID NO 9
<211> LENGTH: 20
<212> TYPE: DNA
<213> ORGANISM: Artificial Sequence
<220> FEATURE:
<223> OTHER INFORMATION: synthetic RT-PCR reverse primer for rat Rex-1

<400> SEQUENCE: 9
tgagttcgct ccaacagtct                                                  20

<210> SEQ ID NO 10
<211> LENGTH: 19
<212> TYPE: DNA
<213> ORGANISM: Artificial Sequence
<220> FEATURE:
<223> OTHER INFORMATION: synthetic RT-PCR forward primer for rat Klf4

<400> SEQUENCE: 10
cagacctgga aagtggtgg                                                   19

<210> SEQ ID NO 11
<211> LENGTH: 19
<212> TYPE: DNA
<213> ORGANISM: Artificial Sequence
<220> FEATURE:
<223> OTHER INFORMATION: synthetic RT-PCR reverse primer for rat Klf4

<400> SEQUENCE: 11
acctgtgttg cccgcagcc                                                   19

<210> SEQ ID NO 12
<211> LENGTH: 25
<212> TYPE: DNA
<213> ORGANISM: Artificial Sequence
<220> FEATURE:
<223> OTHER INFORMATION: synthetic RT-PCR forward primer for rat TDGF2

<400> SEQUENCE: 12
aacaccaaca atattttatg tggcc                                            25

<210> SEQ ID NO 13
<211> LENGTH: 24
<212> TYPE: DNA
<213> ORGANISM: Artificial Sequence
<220> FEATURE:
<223> OTHER INFORMATION: synthetic RT-PCR reverse primer for rat TDGF2

<400> SEQUENCE: 13
tcatttctag gaaaaggcag atgc                                             24

<210> SEQ ID NO 14
<211> LENGTH: 23
<212> TYPE: DNA
<213> ORGANISM: Artificial Sequence
<220> FEATURE:
<223> OTHER INFORMATION: synthetic RT-PCR forward primer for rat FGF-4

<400> SEQUENCE: 14
tgtggtgagc atcttcggag tgg                                              23

<210> SEQ ID NO 15

```
<211> LENGTH: 23
<212> TYPE: DNA
<213> ORGANISM: Artificial Sequence
<220> FEATURE:
<223> OTHER INFORMATION: synthetic RT-PCR reverse primer for rat FGF-4

<400> SEQUENCE: 15
ccttcttggt ccgcccgttc tta                                           23

<210> SEQ ID NO 16
<211> LENGTH: 24
<212> TYPE: DNA
<213> ORGANISM: Artificial Sequence
<220> FEATURE:
<223> OTHER INFORMATION: synthetic RT-PCR forward primer for rat Eras

<400> SEQUENCE: 16
gctgcccctc agccgactgc tact                                          24

<210> SEQ ID NO 17
<211> LENGTH: 24
<212> TYPE: DNA
<213> ORGANISM: Artificial Sequence
<220> FEATURE:
<223> OTHER INFORMATION: synthetic RT-PCR reverse primer for rat Eras

<400> SEQUENCE: 17
cactgccttg tactccggta gctg                                          24

<210> SEQ ID NO 18
<211> LENGTH: 18
<212> TYPE: DNA
<213> ORGANISM: Artificial Sequence
<220> FEATURE:
<223> OTHER INFORMATION: synthetic RT-PCR forward primer for rat
      transgenic Oct4

<400> SEQUENCE: 18
ggggtggacc atcctcta                                                 18

<210> SEQ ID NO 19
<211> LENGTH: 18
<212> TYPE: DNA
<213> ORGANISM: Artificial Sequence
<220> FEATURE:
<223> OTHER INFORMATION: synthetic RT-PCR reverse primer for rat
      transgenic Oct4

<400> SEQUENCE: 19
cctccgcaga actcgtat                                                 18

<210> SEQ ID NO 20
<211> LENGTH: 18
<212> TYPE: DNA
<213> ORGANISM: Artificial Sequence
<220> FEATURE:
<223> OTHER INFORMATION: synthetic RT-PCR forward primer for rat
      transgenic Sox2

<400> SEQUENCE: 20
cccaccgccc tcaaagta                                                 18

<210> SEQ ID NO 21
<211> LENGTH: 21
<212> TYPE: DNA
<213> ORGANISM: Artificial Sequence
<220> FEATURE:
```

```
<223> OTHER INFORMATION: synthetic RT-PCR reverse primer for rat
      transgenic Sox2

<400> SEQUENCE: 21
ggaccatacc atgaaggcgt t                                              21

<210> SEQ ID NO 22
<211> LENGTH: 18
<212> TYPE: DNA
<213> ORGANISM: Artificial Sequence
<220> FEATURE:
<223> OTHER INFORMATION: synthetic RT-PCR forward primer for rat
      transgenic Klf4

<400> SEQUENCE: 22
cccaccgccc tcaaagta                                                  18

<210> SEQ ID NO 23
<211> LENGTH: 19
<212> TYPE: DNA
<213> ORGANISM: Artificial Sequence
<220> FEATURE:
<223> OTHER INFORMATION: synthetic RT-PCR reverse primer for rat
      transgenic Klf4

<400> SEQUENCE: 23
gctggacgca gtgtcttct                                                 19

<210> SEQ ID NO 24
<211> LENGTH: 20
<212> TYPE: DNA
<213> ORGANISM: Artificial Sequence
<220> FEATURE:
<223> OTHER INFORMATION: synthetic RT-PCR forward primer for rat GADPH

<400> SEQUENCE: 24
ccttcattga cctcaactac                                                20

<210> SEQ ID NO 25
<211> LENGTH: 20
<212> TYPE: DNA
<213> ORGANISM: Artificial Sequence
<220> FEATURE:
<223> OTHER INFORMATION: synthetic RT-PCR reverse primer for rat GADPH

<400> SEQUENCE: 25
ggaaggccat gccagtgagc                                                20

<210> SEQ ID NO 26
<211> LENGTH: 20
<212> TYPE: DNA
<213> ORGANISM: Artificial Sequence
<220> FEATURE:
<223> OTHER INFORMATION: synthetic RT-PCR forward primer for human
      endogenous Oct4

<400> SEQUENCE: 26
agtttgtgcc agggttttg                                                 20

<210> SEQ ID NO 27
<211> LENGTH: 20
<212> TYPE: DNA
<213> ORGANISM: Artificial Sequence
<220> FEATURE:
<223> OTHER INFORMATION: synthetic RT-PCR reverse primer for human
      endogenous Oct4
```

```
<400> SEQUENCE: 27
acttcacctt ccctccaacc                                              20

<210> SEQ ID NO 28
<211> LENGTH: 20
<212> TYPE: DNA
<213> ORGANISM: Artificial Sequence
<220> FEATURE:
<223> OTHER INFORMATION: synthetic RT-PCR forward primer for human
      endogenous Nanog

<400> SEQUENCE: 28
tttggaagct gctggggaag                                              20

<210> SEQ ID NO 29
<211> LENGTH: 20
<212> TYPE: DNA
<213> ORGANISM: Artificial Sequence
<220> FEATURE:
<223> OTHER INFORMATION: synthetic RT-PCR reverse primer for human
      endogenous Nanog

<400> SEQUENCE: 29
gatgggagga ggggagagga                                              20

<210> SEQ ID NO 30
<211> LENGTH: 20
<212> TYPE: DNA
<213> ORGANISM: Artificial Sequence
<220> FEATURE:
<223> OTHER INFORMATION: synthetic RT-PCR forward primer for human
      endogenous Sox2

<400> SEQUENCE: 30
caaaaatggc catgcaggtt                                              20

<210> SEQ ID NO 31
<211> LENGTH: 24
<212> TYPE: DNA
<213> ORGANISM: Artificial Sequence
<220> FEATURE:
<223> OTHER INFORMATION: synthetic RT-PCR reverse primer for human
      endogenous Sox2

<400> SEQUENCE: 31
agttgggatc gaacaaaagc tatt                                         24

<210> SEQ ID NO 32
<211> LENGTH: 24
<212> TYPE: DNA
<213> ORGANISM: Artificial Sequence
<220> FEATURE:
<223> OTHER INFORMATION: synthetic RT-PCR forward primer for human Rex-1

<400> SEQUENCE: 32
cagatcctaa acagctcgca gaat                                         24

<210> SEQ ID NO 33
<211> LENGTH: 23
<212> TYPE: DNA
<213> ORGANISM: Artificial Sequence
<220> FEATURE:
<223> OTHER INFORMATION: synthetic RT-PCR reverse primer for human Rex-1

<400> SEQUENCE: 33
gcgtacgcaa attaaagtcc aga                                          23
```

<210> SEQ ID NO 34
<211> LENGTH: 23
<212> TYPE: DNA
<213> ORGANISM: Artificial Sequence
<220> FEATURE:
<223> OTHER INFORMATION: synthetic RT-PCR forward primer for human FGF-4

<400> SEQUENCE: 34
ctacaacgcc tacgagtcct aca                                            23

<210> SEQ ID NO 35
<211> LENGTH: 24
<212> TYPE: DNA
<213> ORGANISM: Artificial Sequence
<220> FEATURE:
<223> OTHER INFORMATION: synthetic RT-PCR reverse primer for human FGF-4

<400> SEQUENCE: 35
gttgcaccag aaaagtcaga gttg                                           24

<210> SEQ ID NO 36
<211> LENGTH: 25
<212> TYPE: DNA
<213> ORGANISM: Artificial Sequence
<220> FEATURE:
<223> OTHER INFORMATION: synthetic RT-PCR forward primer for human TDGF2

<400> SEQUENCE: 36
ctgctgcctg aatgggggaa cctgc                                          25

<210> SEQ ID NO 37
<211> LENGTH: 27
<212> TYPE: DNA
<213> ORGANISM: Artificial Sequence
<220> FEATURE:
<223> OTHER INFORMATION: synthetic RT-PCR reverse primer for human TDGF2

<400> SEQUENCE: 37
gccacgaggt gctcatccat cacaagg                                        27

<210> SEQ ID NO 38
<211> LENGTH: 19
<212> TYPE: DNA
<213> ORGANISM: Artificial Sequence
<220> FEATURE:
<223> OTHER INFORMATION: synthetic RT-PCR forward primer for human
      transgenic Oct4

<400> SEQUENCE: 38
cagtgcccga aacccacac                                                 19

<210> SEQ ID NO 39
<211> LENGTH: 24
<212> TYPE: DNA
<213> ORGANISM: Artificial Sequence
<220> FEATURE:
<223> OTHER INFORMATION: synthetic RT-PCR reverse primer for human
      transgenic Oct4

<400> SEQUENCE: 39
agaggaactg cttccttcac gaca                                           24

<210> SEQ ID NO 40
<211> LENGTH: 20
<212> TYPE: DNA

<213> ORGANISM: Artificial Sequence
<220> FEATURE:
<223> OTHER INFORMATION: synthetic RT-PCR forward primer for human
      transgenic Sox2

<400> SEQUENCE: 40
tacctcttcc tcccactcca                                             20

<210> SEQ ID NO 41
<211> LENGTH: 24
<212> TYPE: DNA
<213> ORGANISM: Artificial Sequence
<220> FEATURE:
<223> OTHER INFORMATION: synthetic RT-PCR reverse primer for human
      transgenic Sox2

<400> SEQUENCE: 41
agaggaactg cttccttcac gaca                                        24

<210> SEQ ID NO 42
<211> LENGTH: 20
<212> TYPE: DNA
<213> ORGANISM: Artificial Sequence
<220> FEATURE:
<223> OTHER INFORMATION: synthetic RT-PCR forward primer for human
      transgenic Nanog

<400> SEQUENCE: 42
cagaaggcct cagcacctac                                             20

<210> SEQ ID NO 43
<211> LENGTH: 24
<212> TYPE: DNA
<213> ORGANISM: Artificial Sequence
<220> FEATURE:
<223> OTHER INFORMATION: synthetic RT-PCR reverse primer for human
      transgenic Nanog

<400> SEQUENCE: 43
agaggaactg cttccttcac gaca                                        24

<210> SEQ ID NO 44
<211> LENGTH: 20
<212> TYPE: DNA
<213> ORGANISM: Artificial Sequence
<220> FEATURE:
<223> OTHER INFORMATION: synthetic RT-PCR forward primer for human GADPH

<400> SEQUENCE: 44
gtggacctga cctgccgtct                                             20

<210> SEQ ID NO 45
<211> LENGTH: 20
<212> TYPE: DNA
<213> ORGANISM: Artificial Sequence
<220> FEATURE:
<223> OTHER INFORMATION: synthetic RT-PCR reverse primer for human GADPH

<400> SEQUENCE: 45
ggaggagtgg gtgtcgctgt                                             20

<210> SEQ ID NO 46
<211> LENGTH: 23
<212> TYPE: DNA
<213> ORGANISM: Artificial Sequence
<220> FEATURE:
<223> OTHER INFORMATION: synthetic bisulfite-sequencing forward primer for rat Oct4

<400> SEQUENCE: 46
atgggatttt ggaggatttt tag                                        23

<210> SEQ ID NO 47
<211> LENGTH: 23
<212> TYPE: DNA
<213> ORGANISM: Artificial Sequence
<220> FEATURE:
<223> OTHER INFORMATION: synthetic bisulfite-sequencing reverse primer
      for rat Oct4

<400> SEQUENCE: 47
ctcaaaccca aatacccccta ctt                                       23

<210> SEQ ID NO 48
<211> LENGTH: 27
<212> TYPE: DNA
<213> ORGANISM: Artificial Sequence
<220> FEATURE:
<223> OTHER INFORMATION: synthetic bisulfite-sequencing forward primer
      for human Oct4

<400> SEQUENCE: 48
ggatgttatt aagatgaaga tagttgg                                    27

<210> SEQ ID NO 49
<211> LENGTH: 25
<212> TYPE: DNA
<213> ORGANISM: Artificial Sequence
<220> FEATURE:
<223> OTHER INFORMATION: synthetic bisulfite-sequencing reverse primer
      for human Oct4

<400> SEQUENCE: 49
cctaaactcc ccttcaaaat ctatt                                      25

<210> SEQ ID NO 50
<211> LENGTH: 24
<212> TYPE: DNA
<213> ORGANISM: Artificial Sequence
<220> FEATURE:
<223> OTHER INFORMATION: synthetic RT-PCR forward primer for Blimp1

<400> SEQUENCE: 50
tcagcctctt ccctaggttg tatc                                       24

<210> SEQ ID NO 51
<211> LENGTH: 25
<212> TYPE: DNA
<213> ORGANISM: Artificial Sequence
<220> FEATURE:
<223> OTHER INFORMATION: synthetic RT-PCR reverse primer for Blimp1

<400> SEQUENCE: 51
aatcttaagg atccatcggt tcaac                                      25

<210> SEQ ID NO 52
<211> LENGTH: 20
<212> TYPE: DNA
<213> ORGANISM: Artificial Sequence
<220> FEATURE:
<223> OTHER INFORMATION: synthetic RT-PCR forward primer for Brachyury

<400> SEQUENCE: 52

```
atgccaaaga aagaaacgac                                              20

<210> SEQ ID NO 53
<211> LENGTH: 20
<212> TYPE: DNA
<213> ORGANISM: Artificial Sequence
<220> FEATURE:
<223> OTHER INFORMATION: synthetic RT-PCR reverse primer for Brachyury

<400> SEQUENCE: 53
agaggctgta gaacatgatt                                              20

<210> SEQ ID NO 54
<211> LENGTH: 20
<212> TYPE: DNA
<213> ORGANISM: Artificial Sequence
<220> FEATURE:
<223> OTHER INFORMATION: synthetic RT-PCR forward primer for Cdx2

<400> SEQUENCE: 54
aggctgagcc atgaggagta                                              20

<210> SEQ ID NO 55
<211> LENGTH: 21
<212> TYPE: DNA
<213> ORGANISM: Artificial Sequence
<220> FEATURE:
<223> OTHER INFORMATION: synthetic RT-PCR reverse primer for Cdx2

<400> SEQUENCE: 55
cgaggtccat aattccactc a                                            21

<210> SEQ ID NO 56
<211> LENGTH: 24
<212> TYPE: DNA
<213> ORGANISM: Artificial Sequence
<220> FEATURE:
<223> OTHER INFORMATION: synthetic RT-PCR forward primer for Dax1

<400> SEQUENCE: 56
gtggcagggc agcatcctct acaa                                         24

<210> SEQ ID NO 57
<211> LENGTH: 16
<212> TYPE: DNA
<213> ORGANISM: Artificial Sequence
<220> FEATURE:
<223> OTHER INFORMATION: synthetic RT-PCR reverse primer for Dax1

<400> SEQUENCE: 57
caaaagaagc ggtaca                                                  16

<210> SEQ ID NO 58
<211> LENGTH: 23
<212> TYPE: DNA
<213> ORGANISM: Artificial Sequence
<220> FEATURE:
<223> OTHER INFORMATION: synthetic RT-PCR forward primer for Essrb

<400> SEQUENCE: 58
cgccatcaaa tgcgagtaca tgc                                          23

<210> SEQ ID NO 59
<211> LENGTH: 22
<212> TYPE: DNA
<213> ORGANISM: Artificial Sequence
```

```
<220> FEATURE:
<223> OTHER INFORMATION: synthetic RT-PCR reverse primer for Esrrb

<400> SEQUENCE: 59
gaatcaccat ccaggcactc tg                                              22

<210> SEQ ID NO 60
<211> LENGTH: 22
<212> TYPE: DNA
<213> ORGANISM: Artificial Sequence
<220> FEATURE:
<223> OTHER INFORMATION: synthetic RT-PCR forward primer for
      Fbxo15/ECAT3

<400> SEQUENCE: 60
tagattcttg gacttccgtt ca                                              22

<210> SEQ ID NO 61
<211> LENGTH: 20
<212> TYPE: DNA
<213> ORGANISM: Artificial Sequence
<220> FEATURE:
<223> OTHER INFORMATION: synthetic RT-PCR reverse primer for
      Fbxo15/ECAT3

<400> SEQUENCE: 61
accaaggtca ccgcatccaa                                                 20

<210> SEQ ID NO 62
<211> LENGTH: 23
<212> TYPE: DNA
<213> ORGANISM: Artificial Sequence
<220> FEATURE:
<223> OTHER INFORMATION: synthetic RT-PCR forward primer for Fgf4

<400> SEQUENCE: 62
cgtggtgagc atcttcggag tgg                                             23

<210> SEQ ID NO 63
<211> LENGTH: 23
<212> TYPE: DNA
<213> ORGANISM: Artificial Sequence
<220> FEATURE:
<223> OTHER INFORMATION: synthetic RT-PCR reverse primer for Fgf4

<400> SEQUENCE: 63
ccttcttggt ccgcccgttc tta                                             23

<210> SEQ ID NO 64
<211> LENGTH: 23
<212> TYPE: DNA
<213> ORGANISM: Artificial Sequence
<220> FEATURE:
<223> OTHER INFORMATION: synthetic RT-PCR forward primer for Fgf5

<400> SEQUENCE: 64
ctgtactgca gagtgggcat cgg                                             23

<210> SEQ ID NO 65
<211> LENGTH: 23
<212> TYPE: DNA
<213> ORGANISM: Artificial Sequence
<220> FEATURE:
<223> OTHER INFORMATION: synthetic RT-PCR reverse primer for Fgf5

<400> SEQUENCE: 65
```

```
gacttctgcg aggctgcgac agg                                          23

<210> SEQ ID NO 66
<211> LENGTH: 21
<212> TYPE: DNA
<213> ORGANISM: Artificial Sequence
<220> FEATURE:
<223> OTHER INFORMATION: synthetic RT-PCR forward primer for GADPH

<400> SEQUENCE: 66
gtgttcctac ccccaatgtg t                                            21

<210> SEQ ID NO 67
<211> LENGTH: 24
<212> TYPE: DNA
<213> ORGANISM: Artificial Sequence
<220> FEATURE:
<223> OTHER INFORMATION: synthetic RT-PCR reverse primer for GADPH

<400> SEQUENCE: 67
attgtcatac caggaaatga gctt                                         24

<210> SEQ ID NO 68
<211> LENGTH: 28
<212> TYPE: DNA
<213> ORGANISM: Artificial Sequence
<220> FEATURE:
<223> OTHER INFORMATION: synthetic RT-PCR forward primer for Gata6

<400> SEQUENCE: 68
accttatggc gtagaaatgc tgagggtg                                     28

<210> SEQ ID NO 69
<211> LENGTH: 28
<212> TYPE: DNA
<213> ORGANISM: Artificial Sequence
<220> FEATURE:
<223> OTHER INFORMATION: synthetic RT-PCR reverse primer for Gata6

<400> SEQUENCE: 69
ctgaatactt gaggtcactg ttctcggg                                     28

<210> SEQ ID NO 70
<211> LENGTH: 20
<212> TYPE: DNA
<213> ORGANISM: Artificial Sequence
<220> FEATURE:
<223> OTHER INFORMATION: synthetic RT-PCR forward primer for Pecam1

<400> SEQUENCE: 70
gtcatggcca tggtcgagta                                              20

<210> SEQ ID NO 71
<211> LENGTH: 20
<212> TYPE: DNA
<213> ORGANISM: Artificial Sequence
<220> FEATURE:
<223> OTHER INFORMATION: synthetic RT-PCR reverse primer for Pecam1

<400> SEQUENCE: 71
agcaggacag gtccaacaac                                              20

<210> SEQ ID NO 72
<211> LENGTH: 22
<212> TYPE: DNA
<213> ORGANISM: Artificial Sequence
```

```
<220> FEATURE:
<223> OTHER INFORMATION: synthetic RT-PCR forward primer for Rex-1

<400> SEQUENCE: 72
tgaaagtgag attagccccg ag                                          22

<210> SEQ ID NO 73
<211> LENGTH: 22
<212> TYPE: DNA
<213> ORGANISM: Artificial Sequence
<220> FEATURE:
<223> OTHER INFORMATION: synthetic RT-PCR reverse primer for Rex-1

<400> SEQUENCE: 73
gtcccatccc cttcaatagc ac                                          22

<210> SEQ ID NO 74
<211> LENGTH: 18
<212> TYPE: DNA
<213> ORGANISM: Artificial Sequence
<220> FEATURE:
<223> OTHER INFORMATION: synthetic RT-PCR forward primer for Stella

<400> SEQUENCE: 74
gaaactcctc agaagaaa                                               18

<210> SEQ ID NO 75
<211> LENGTH: 20
<212> TYPE: DNA
<213> ORGANISM: Artificial Sequence
<220> FEATURE:
<223> OTHER INFORMATION: synthetic RT-PCR reverse primer for Stella

<400> SEQUENCE: 75
ctcttgttct ccacaggtac                                             20

<210> SEQ ID NO 76
<211> LENGTH: 22
<212> TYPE: DNA
<213> ORGANISM: Artificial Sequence
<220> FEATURE:
<223> OTHER INFORMATION: synthetic RT-PCR forward primer for Stra8

<400> SEQUENCE: 76
gcaaccaacc cagtgatgat gg                                          22

<210> SEQ ID NO 77
<211> LENGTH: 21
<212> TYPE: DNA
<213> ORGANISM: Artificial Sequence
<220> FEATURE:
<223> OTHER INFORMATION: synthetic RT-PCR reverse primer for Stra8

<400> SEQUENCE: 77
catctggtcc aacagcctca g                                           21

<210> SEQ ID NO 78
<211> LENGTH: 30
<212> TYPE: DNA
<213> ORGANISM: Artificial Sequence
<220> FEATURE:
<223> OTHER INFORMATION: synthetic bisulfite-sequencing PCR forward
      primer for Fgf4

<400> SEQUENCE: 78
tttaggtttt aagagtgttg gggagaagat                                  30
```

```
<210> SEQ ID NO 79
<211> LENGTH: 30
<212> TYPE: DNA
<213> ORGANISM: Artificial Sequence
<220> FEATURE:
<223> OTHER INFORMATION: synthetic bisulfite-sequencing PCR reverse
      primer for Fgf4

<400> SEQUENCE: 79
tacaaaacaa aaacatcaaa cccattctaa                                        30

<210> SEQ ID NO 80
<211> LENGTH: 26
<212> TYPE: DNA
<213> ORGANISM: Artificial Sequence
<220> FEATURE:
<223> OTHER INFORMATION: synthetic bisulfite-sequencing PCR forward
      primer for Stella

<400> SEQUENCE: 80
attttgtgat tagggttggt ttagaa                                            26

<210> SEQ ID NO 81
<211> LENGTH: 27
<212> TYPE: DNA
<213> ORGANISM: Artificial Sequence
<220> FEATURE:
<223> OTHER INFORMATION: synthetic bisulfite-sequencing PCR reverse
      primer for Stella

<400> SEQUENCE: 81
ccaaaacatc ctcttcatct ttcttct                                           27

<210> SEQ ID NO 82
<211> LENGTH: 22
<212> TYPE: DNA
<213> ORGANISM: Artificial Sequence
<220> FEATURE:
<223> OTHER INFORMATION: synthetic bisulfite-sequencing PCR forward
      primer for Stella nest

<400> SEQUENCE: 82
tttttggaat tggttgggat tg                                                22

<210> SEQ ID NO 83
<211> LENGTH: 28
<212> TYPE: DNA
<213> ORGANISM: Artificial Sequence
<220> FEATURE:
<223> OTHER INFORMATION: synthetic bisulfite-sequencing PCR reverse
      primer for Stella nest

<400> SEQUENCE: 83
cttctaaaaa atttcaaaat ccttcatt                                          28

<210> SEQ ID NO 84
<211> LENGTH: 20
<212> TYPE: DNA
<213> ORGANISM: Artificial Sequence
<220> FEATURE:
<223> OTHER INFORMATION: synthetic chromatin immunoprecipitation
      (ChIP-qPCR) forward primer for Stella

<400> SEQUENCE: 84
gatccagctg gtctgagcta                                                   20
```

<210> SEQ ID NO 85
<211> LENGTH: 20
<212> TYPE: DNA
<213> ORGANISM: Artificial Sequence
<220> FEATURE:
<223> OTHER INFORMATION: synthetic chromatin immunoprecipitation
      (ChIP-qPCR) reverse primer for Stella

<400> SEQUENCE: 85
gtgcagggat cataggagtg                                            20

<210> SEQ ID NO 86
<211> LENGTH: 20
<212> TYPE: DNA
<213> ORGANISM: Artificial Sequence
<220> FEATURE:
<223> OTHER INFORMATION: synthetic real-time PCR primer Dppa3

<400> SEQUENCE: 86
caacctacat cccagggtct                                            20

<210> SEQ ID NO 87
<211> LENGTH: 20
<212> TYPE: DNA
<213> ORGANISM: Artificial Sequence
<220> FEATURE:
<223> OTHER INFORMATION: synthetic real-time PCR primer Dppa3

<400> SEQUENCE: 87
tcaacgtctc ggaggagatt                                            20

<210> SEQ ID NO 88
<211> LENGTH: 19
<212> TYPE: DNA
<213> ORGANISM: Artificial Sequence
<220> FEATURE:
<223> OTHER INFORMATION: synthetic real-time PCR primer Gbx2

<400> SEQUENCE: 88
aaaggcttcc tggccaaag                                             19

<210> SEQ ID NO 89
<211> LENGTH: 20
<212> TYPE: DNA
<213> ORGANISM: Artificial Sequence
<220> FEATURE:
<223> OTHER INFORMATION: synthetic real-time PCR primer Gbx2

<400> SEQUENCE: 89
ttgactcgtc tttcccttgc                                            20

<210> SEQ ID NO 90
<211> LENGTH: 22
<212> TYPE: DNA
<213> ORGANISM: Artificial Sequence
<220> FEATURE:
<223> OTHER INFORMATION: synthetic real-time PCR primer Klf4

<400> SEQUENCE: 90
agcctaaatg atggtgcttg gt                                         22

<210> SEQ ID NO 91
<211> LENGTH: 23
<212> TYPE: DNA
<213> ORGANISM: Artificial Sequence
<220> FEATURE:

```
<223> OTHER INFORMATION: synthetic real-time PCR primer Klf4

<400> SEQUENCE: 91
ttgaaaactt tggcttcctt gtt                                        23
```

GENERATION AND MAINTENANCE OF STEM CELLS

CROSS-REFERENCE TO RELATED APPLICATIONS

This application is a continuation of U.S. application Ser. No. 13/140,108, filed Sep. 1, 2011, issued as U.S. Pat. No. 8,906,677, which is a U.S. National Phase application under 35 U.S.C. §371 of International Application No. PCT/US2009/068274, filed Dec. 16, 2009, which claims priority to U.S. Provisional Application No. 61/138,407, filed Dec. 17, 2008, the disclosures of which are incorporated by reference herein.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -29-2.TXT, created on Oct. 13, 2014, 20,480 bytes, machine format IBM-PC, MS-Windows operating system, is hereby incorporated by reference in its entirety for all purposes.

BACKGROUND OF THE INVENTION

Although embryonic stem cells (ESCs) have been established from mice since 1981, attempts to derive their counterparts from various other mammals, including rats, have not succeeded. Recently, pluripotent stem cells were derived from the post-implantation egg cylinder stage Epiblasts of mouse and rat (Brons et al., *Nature* 448, 191-195 (2007); Tesar et al., *Nature* 448, 196-199 (2007)). These novel stem cells were named Epiblast stem cells (EpiSCs). EpiSCs seem to correspond very closely to human embryonic stem cells (hESCs) in the colony morphology and culture/signaling requirements for maintaining pluripotency, but exhibit a range of significant phenotypic and signaling response differences from the mouse ES cells (mESCs).

Leukemia inhibitory factor (LIF) is essential for maintaining the pluripotency of mESCs in the presence of serum through JAK-STAT3 pathway (Niwa et al., *Genes Dev* 12, 2048-2060 (1998)). However, in serum-free medium, BMP4 is also required, together with LIF, to sustain mESC self-renewal by inducing inhibitor of differentiation (Id) protein expression (Ying et al., *Cell* 115, 281-292 (2003)) and inhibiting ERK activation (Qi et al., *Proc Natl Acad Sci USA* 101, 6027-6032 (2005)). In contrast to mESCs, LIF cannot support EpiSCs/hESCs, which typically require basic fibroblast growth factor (bFGF)/Activin A for long term self-renewal. Undifferentiated hESCs display high-level basal activity of ERK through bFGF signaling (Dvorak et al., *Stem Cells* 23, 1200-1211 (2005)). BMP4 doesn't support EpiSC/hESC self-renewal either, but instead induces EpiSC/hESC to differentiate into trophoblasts or primitive endoderm (Brons et al., *Nature* 448, 191-195 (2007); Tesar et al., *Nature* 448, 196-199 (2007); Xu et al., *Nat Biotechnol* 20, 1261-1264 (2002)). In addition to bFGF, Activin A/Nodal signaling has been shown to support the undifferentiated state of hESCs/EpiSCs (Brons et al., *Nature* 448, 191-195 (2007); Sato et al., *Dev Biol* 260, 404-413 (2003); Tesar et al., *Nature* 448, 196-199 (2007)), while is dispensable for mESCs. These results strongly support the notion that EpiSCs and hESCs are intrinsically similar and raise an attractive hypothesis that mESCs and EpiSCs/hESCs represent two distinct pluripotent states: the mESC-like state representing the pre-implantation inner cell mass (ICM) and EpiSC-like state representing later Epiblast cells, respectively.

mESCs can be usually derived from certain mouse strains using feeder layer based cell culture conditions (Martin, G. R., *Proc Natl Acad Sci USA* 78, 7634-7638 (1981)). However, it has been proven difficult to derive authentic ES cells from rats under similar conditions. Establishments of rat ESC-like cells have been reported (Demers et al., *Cloning Stem Cells* 9, 512-522 (2007); Ruhnke et al., *Stem Cells* 21, 428-436 (2003); Schulze et al., *Methods Mol Biol* 329, 45-58 (2006); Ueda et al., *PLoS ONE* 3, e2800 (2008)), but these cells either could not be stably maintained or lacked true in vivo pluripotency (e.g. fail to form teratoma or no/little contribution to chimerism). Similarly, although (in vitro) pluripotent rat EpiSCs had been derived, both rat and mouse EpiSCs show little or no ability to be reincorporated into the pre-implantation embryo and contribute to chimaeras (Brons et al., *Nature* 448, 191-195 (2007); Tesar et al., *Nature* 448, 196-199 (2007)).

Recently, induced pluripotent stem cells (iPSCs) generated from both mouse and human somatic cells by defined genetic transduction have attracted enormous interests (Dimos et al., *Science* 321, 1218-1221 (2008); Han, J., and Sidhu, K. S. *Curr Stem Cell Res Ther* 3, 66-74 (2008); Takahashi et al., *Cell* 131, 861-872 (2007); Takahashi, K., and Yamanaka, S., *Cell* 126, 663-676 (2006); Yu et al., *Science* 318, 1917-1920 (2007)).

BRIEF SUMMARY OF THE INVENTION

The present invention provides for methods of culturing pluripotent cells through at least one cell divisional. In some embodiments, the methods comprise culturing pluripotent animal cells in the presence of a sufficient amount of:
a. an ALK5 inhibitor (or other TGFβ/activin pathway inhibitor), and
b. a second compound selected from one or more of a MEK inhibitor, an Erk inhibitor, a p38 inhibitor, and an FGF receptor inhibitor; and
c. sufficient nutrients for a sufficient time, to allow for at least one cell division while maintaining cell pluripotency.

In some embodiments, the culturing step further comprises culturing the cells in the presence of an amount of a GSK3β inhibitor. In some embodiments, the GSK3β inhibitor is CHIR99021.

In some embodiments, the second compound is a MEK inhibitor. In some embodiments, the MEK inhibitor is PD0325901.

In some embodiments, the second compound is a Erk inhibitor.

In some embodiments, the culturing step is performed in the further presence of Leukemia inhibiting factor (LIF).

In some embodiments, the ALK5 inhibitor is A-83-01. In some embodiments, the ALK5 inhibitor is SB431542.

In some embodiments, the pluripotent cells are cultured through at least five cell divisions while maintaining cell pluripotency.

In some embodiments, the method further comprises introducing a heterologous nucleic acid into the pluripotent cells and culturing the resulting cells to allow for at least one additional cell divisional while maintaining pluripotency. In some embodiments, a heterologous nucleic acid is introduced into animal cells, then induced to pluripotency, and then submitted to the culturing step.

In some embodiments, the cell is a rat or human cell. In some embodiments, the cell is a primate, ovine, bovine, feline, canine, or porcine cell.

In some embodiments, the pluripotent cells are embryonic stem cells. In some embodiments, the pluripotent cells are induced pluripotent stem cells.

In some embodiments, the cells are non-human animal cells and the method further comprises introducing the pluripotent cells into a blastocyst, wherein the blastocyst is from the same species of animal as the cells, and introducing the blastocyst into the uterus of an animal of the same species. In some embodiments, the method comprises selecting chimeric progeny of the animal based on the presence of a nucleic acid from the pluripotent cells.

The present invention also provides for cultures of pluripotent mammalian cells. In some embodiments, the cultures comprise a sufficient amount of:
a. an ALK5 inhibitor (or other TGFβ/activin pathway inhibitor), and
b. a second compound selected from one or more of a MEK inhibitor, an Erk inhibitor, a p38 inhibitor, and an FGF receptor inhibitor;
to allow for at least one cell division while maintaining cell pluripotency.

In some embodiments, the cultures further comprise LIF.

In some embodiments, the cultures further comprise an amount of a GSK3β inhibitor. In some embodiments, the GSK3β inhibitor is CHIR99021.

In some embodiments, the second compound is a MEK inhibitor. In some embodiments, the MEK inhibitor is PD0325901.

In some embodiments, the second compound is a Erk inhibitor. In some embodiments, the ALK5 inhibitor is A-83-01. In some embodiments, the ALK5 inhibitor is SB431542.

In some embodiments, the cell is a rat or human cell. In some embodiments, the cell is a primate, ovine, bovine, feline, canine, or porcine cell. In some embodiments, the cells are induced pluripotent stem cells or embryonic stem cells.

The present invention also provides a cell culture medium. In some embodiments, the medium comprises a sufficient amount of:
a. an ALK5 inhibitor (or other TGFβ/activin pathway inhibitor), and
b. a second compound selected from one or more of a MEK inhibitor, an Erk inhibitor, a p38 inhibitor, and an FGF receptor inhibitor to allow for at least one cell division while maintaining cell pluripotency when pluripotent cells are cultured in the medium.

In some embodiments, the medium further comprises LIF.

In some embodiments, the medium further comprises an amount of a GSK3β inhibitor. In some embodiments, the GSK3β inhibitor is CHIR99021.

In some embodiments, the second compound is a MEK inhibitor. In some embodiments, the MEK inhibitor is PD0325901.

In some embodiments, the second compound is a Erk inhibitor. In some embodiments, the ALK5 inhibitor is A-83-01. In some embodiments, the ALK5 inhibitor is SB431542.

In some embodiments, the medium is in a pre-packaged, seal container. In some embodiments, the medium comprises DMEM or other media compatible for growing human, rat, mouse or other animal cells.

The present invention also provides isolated pluripotent animal cells that replicates and maintains pluripotency in the presence of leukemia inhibitory factor (LIF) and bone morphogenic protein (BMP), or under inhibition of the TGFβ and activin signaling pathway, inhibition of the MAPK signaling pathway, and optionally inhibition of the FGF pathway. In some embodiments, the isolated pluripotent animal cell is not a murine embryonic stem cell (mESC). In some embodiments, the cell is a human cell. In some embodiments, the cell is a human embryonic stem cell. In some embodiments, the cell is a human iPS cell. In some embodiments, the cell is a rat cell. In some embodiments, the cell is a rat embryonic stem cell. In some embodiments, the cell is a rat iPS cell. In some embodiments, the cell maintains pluripotency under inhibition of ALK5 and MEK. In some embodiments, the cell comprises a heterologous expression cassette, including but not limited to an expression cassette encoding a selectable or detectable marker (e.g., alkaline phosphatase).

The isolated pluripotent cell of the present invention expresses a higher level of E-cadherin as compared to conventionally-cultured hESCs, Epiblast stem cells and human induced pluripotent cells. For example, the isolated pluripotent animal cell expresses a 2-fold higher level of E-cadherin as compared to conventionally-cultured hESCs, EpiSCs and human induced pluripotent cells. In some embodiments, the isolated pluripotent animal cell expresses a higher level of markers as compared to conventionally-cultured hESCs, Epiblast stem cells and human induced pluripotent cells, wherein the markers include Gbx2, Dppa3, Klf4, and Rex1.

In some embodiments, the isolated pluripotent cell of the present invention is cultured in the presence of an ALK5 inhibitor, a second compound selected from a MEK inhibitor, an Erk inhibitor, a p38 inhibitor, and an FGF receptor inhibitor. In some embodiments, the isolated pluripotent cell of the present invention is obtained or obtainable by culturing a cell in the presence of an ALK5 inhibitor, and a second compound selected from one or more of a MEK inhibitor, an Erk inhibitor, a p38 inhibitor, and an FGF receptor inhibitor. For example, the isolated pluripotent cell of the present invention is obtained or obtainable by culturing conventionally-cultured hESCs, EpiSCs, rat ESCs, or primate ESCs.

The present invention also provides methods of increasing the pluripotency of a partially pluripotent mammalian cell to a more fully pluripotent cell. In some embodiments, the methods comprise,
(a) contacting the partially pluripotent cell with an epigenetic modifier selected from a histone deacetylase inhibitor, an inhibitor of histone H3K4 demethylation or an activator of H3K4 methylation;
(b) after step (a) culturing the cell with two or more of (i) an ALK5 inhibitor, (ii) a MEK inhibitor, an Erk inhibitor, or a p38 inhibitor, and (iii) an FGF receptor inhibitor and in the absence of the epigenetic modifier, thereby generating the more fully pluripotent cell as compared to the partially pluripotent mammalian cell.

In some embodiments, the methods further comprise
(c) culturing the partially pluripotent mammalian cell after step (b) with (i) an ALK5 inhibitor, (ii) a MEK inhibitor, an Erk inhibitor, or a p38 inhibitor, and (iii) an FGF receptor inhibitor and (iv) a GSK3 inhibitor.

In some embodiments, culturing steps (a) and/or (b) and/or (c) further comprises culturing the partially pluripotent mammalian cell in the presence of Leukemia inhibitory factor (LIF).

In some embodiments, the partially pluripotent cell is an Epiblast stem cell.

In some embodiments, the partially pluripotent cell does not express at least one marker selected from the group consisting of Oct4, Nanog, SSEA-1, and REX-1 and the more fully pluripotent cell expresses one or more or all of the markers.

In some embodiments, the partially pluripotent cell does not express ALP-1 and the more fully pluripotent cell expresses ALP-1.

In some embodiments, the epigenetic modifier is valproic acid or parnate.

BRIEF DESCRIPTION OF THE DRAWINGS

The patent or patent application file contains at least one drawing executed in color. Copies of this patent or patent application publication with color drawing(s) will be provided by the U.S. Patent and Trademark Office upon request and payment of the necessary fee.

FIG. 2A-I. riPSCs have pluripotent developmental potential in vitro and in vivo Immunostaining showed riPSCs could differentiate into endoderm (Albumin and Pdx1) (A and B), neuroectoderm (βIII-tubulin, Tuj1) (C) and mesoderm (Brachyury) (D) derivatives in vitro. Also, riPSCs can form teratoma in SCID mice, which consisted of all three germ layers (E~H). In addition, after injected into Brown-Norway rat blastocysts, riPSCs with WB F344 background were capable of producing chimera rats (I). Relative magnification: A~E (100×), F~H and J~Q (200×).

FIG. 3A-L. The generation of novel "mESC-like" hiPSCs. IMR90 human fibroblasts were transduced with Oct4, Sox2, Nanog, and Lin28 by lentiviruses. The hiPSC colonies were observed three weeks after transduction (A), picked up at the fourth week after transduction and were stably maintained under the cocktail of hLIF, 0.5 µM PD0325901, 0.5 µM A-83-01, and 3 µM CHIR99021. Such hiPSCs formed domed colonies similar to mESCs (B). Under such conditions, hiPSCs were positive to ALP (C) and other typical pluripotency markers (D~I). RT-PCR analysis of four clonal hiPSC lines confirmed the expression of endogenous pluripotency genes (J), but the virally transduced genes were largely silenced. Oct4 promoter of hiPSCs clones exhibited a demethylation pattern similar to conventionally-cultured human ES cells, but is distinct from that of the parental IMR90 fibroblasts (K). A karyotype analysis of hiPSCs is provided (L).

FIG. 4A-E. Immunostaining showed that the hiPSCs could effectively differentiate into endoderm (Albumin) (A), neuroectoderm (βIII-tubulin, Tuj1) (B) and mesoderm (Brachyury) (C) derivatives in vitro. After transplanted into the SCID mice, hiPSCs could form teratoma, which consisted of all three germ layers including neuroepithelium-like structure (ectoderm) (D), tube-like structure (endoderm) (D), cartilage-like structure (mesoderm) (E). Relative magnification: A (100×), B~E (200×).

FIG. 8A-E. Molecular characterizations of the converted Parnate/mAMFGi cells. (A) Immunocytochemistry showed homogeneous expression of pluripotency markers, Oct4 (Green), Nanog (Red), and SSEA-1(Red) in Parnate/mAMFGi cells. (B) Expression of specific ICM marker genes (Rex-1, Pecam1, Dax 1, Dppa5, Esrrb, Fgf4, and Fbxo15), germline competence associated marker genes (Stella and Stra8), and Epiblast gene (fgf5) in mESCs, EpiSCs, and parnate/mAMFGi cells were analyzed by semi-quantitative RT-PCR. GADPH was used as a control. (C) Transcriptome analysis of mESCs, EpiSCs, and parnate/mAMFGi cells showed that Parnate/mAMFGi cells are much more similar to mESCs than EpiSCs. Two biological replicates were used for all three cell types. (D) Methylation analysis of Stella and Fgt4 promoters by bisulfate genomic sequencing. Open and closed circles indicate unmethylated and methylated CpGs, respectively. (E) ChIP-QPCR analysis of the indicated histone modifications in the stella locus in various cells. Genomic DNAs were immunoprecipitated from feeder-free cultured EpiSCs, R1-mESCs, and Parnate/mAMFGi cells with antibodies as indicated, followed by Q-PCR analysis using a primer set specific to the endogenous genomic locus encoding Stella. Levels of histone modifications were represented as percentage of input. IgG served as no-antibody control.

DEFINITIONS

Figure 1A:
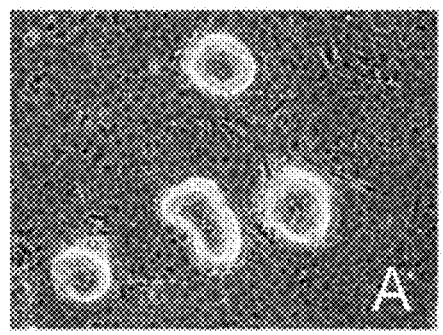
FIG. 1. mESC-like riPSCs could be generated from rat WB-F344 cells after transduced with Oct4, Sox2 and Klf4 by retroviruses and captured/maintained under combination of LIF, 0.5 µM PD0325901, 0.5 µM A-83-01 and 3 µM CHIR99021. ESC-like colonies were observed 10 days after transduction (A), but could not be maintained in the conventional mESC culture condition (B). In the presence of 0.5 µM PD0325901 and 3 µM CHIR99021, riPSCs can be short-term maintained in culture but show extensive spontaneous differentiation (C). With the combination of 0.5 µM PD0325901, 3 µM CHIR99021, and 0.5 µM A-83-01, riPSCs can long-term and homogenously self-renew (D), and form mESC-like domed colonies in culture (E). Immunocytochemistry revealed that riPSCs express typical mESC markers, such as Oct4 (F), Sox2 (G), SSEA-1(H, Green) and Nanog (H, red). RT-PCR analysis of four clonal riPSC lines confirmed the expression of endogenous typical pluripotency markers (I), but the virally transduced genes were largely silenced. Oct4 promoter of riPSC clones exhibited a demethylation pattern and is distinct from that of the parental WB-F344 cells (J). Karyotyping analysis showed the chromosome number of riPSCs was 42 (K).

The term "pluripotent" or "pluripotency" refers to cells with the ability to give rise to progeny that can undergo differentiation, under the appropriate conditions, into cell types that collectively demonstrate characteristics associated with cell lineages from all of the three germinal layers (endoderm, mesoderm, and ectoderm). Pluripotent stem cells can contribute to many or all tissues of a prenatal, postnatal or adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells. Cell pluripotency is a continuum, ranging from the completely pluripotent cell that can form every cell of the embryo proper, e.g., embyronic stem cells and iPSCs, to the incompletely or partially pluripotent cell that can form cells of all three germ layers but that may not exhibit all the characteristics of completely pluripotent cells, such as, for example, germline transmission or the ability to generate a whole organism. In particular embodiments, the pluripotency of a cell is increased from an incompletely or partially pluripotent cell to a more pluripotent cell or, in certain embodiments, a completely pluripotent cell. Pluripotency can be assessed, for example, by teratoma formation, germline transmission, and tetraploid embryo complementation. In some embodiments, expression of pluripotency genes or pluripotency markers as discussed elsewhere herein, can be used to assess the pluripotency of a cell.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics.

The term "library" is used according to its common usage in the art, to denote a collection of molecules, optionally organized and/or cataloged in such a way that individual members can be identified. Libraries can include, but are not limited to, combinatorial chemical libraries, natural products libraries, and peptide libraries.

A "recombinant" polynucleotide is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

"Expression cassette" refers to a polynucleotide comprising a promoter or other regulatory sequence operably linked to a sequence encoding a protein.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "heterologous sequence" or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA, being linked to a heterologous promoter, being linked to a reporter gene, etc.

The terms "agent" or "test compound" refer to any compound useful in the screening assays described herein. An agent can be, for example, an organic compound, a polypeptide (e.g., a peptide or an antibody), a nucleic acid (e.g., DNA, RNA, double-stranded, single-stranded, an oligonucleotide, antisense RNA, small inhibitory RNA, micro RNA, a ribozyme, etc.), an oligosaccharide, a lipid. Usually, the agents used in the present screening methods have a molecular weight of less than 10,000 daltons, for example, less than 8000, 6000, 4000, 2000 daltons, e.g., between 50-1500, 500-1500, 200-2000, 500-5000 daltons. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., ability to induce pluripotency under certain conditions such as are described herein, creating variants of the lead compound, and evaluating the property and activity of those variant compounds. Often, high throughput screening (HTS) methods are employed for such an analysis.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Inhibitors," "activators," and "modulators" of expression or of activity are used to refer to inhibitory, activating, or modulating molecules, respectively, identified using in vitro and in vivo assays for expression or activity of a described target protein (or encoding polynucleotide), e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100%. Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more higher.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include, Oct-1, Oct-2, Oct-3/4, Oct-6, Oct-7, Oct-8, Oct-9, and Oct-11. e.g. Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G. *Genes Dev.* 11, 1207-1225 (1997). In some embodiments, variants have at least 85%, 90%, or 95% amino acid sequence identity across their whole sequence compared to a naturally occurring Oct polypeptide family member such as to those listed above or such as listed in Genbank accession number NP_002692.2 (human Oct4) or NP_038661.1 (mouse Oct4). Oct polypeptides (e.g., Oct3/4) can be from human, mouse, rat, bovine, porcine, or other animals. Generally, the same species of protein will be used with the species of cells being manipulated.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W. *Cell* Biol. 32, 1103-1121 (2000). Exemplary Klf family members include, Klf1, Klf2, Klf3, Klf-4, Klf5, Klf6, Klf7, KB, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. See, Nakagawa, et al., *Nature Biotechnology* 26:101-106 (2007). In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. To the extent a Klf polypeptide is described herein, it can be replaced with an estrogen-related receptor beta (Essrb) polypeptide. Thus, it is intended that for each Klf polypeptide embodiment described herein, a corresponding embodiment using Essrb in the place of a Klf4 polypeptide is equally described.

A "Myc polypeptide" refers any of the naturally-occurring members of the Myc family (see, e.g., Adhikary, S. & Eilers, M. *Nat. Rev. Mol. Cell. Biol.* 6:635-645 (2005)), or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, e.g., Dang, D. T., et al., *Int. J. Biochem. Cell Biol.* 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. See, Nakagawa, et al., *Nature Biotechnology* 26:101-106 (2007). In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated.

DETAILED DESCRIPTION OF THE INVENTION

I. Introduction

The present invention is based in the surprising finding that ALK5 inhibitors significantly improve the maintenance, and optionally, induction of pluripotency in cells. Combination of an inhibitor of ALK5 with a MAPK inhibitor (e.g., a MEK inhibitor, an Erk inhibitor or a p38 inhibitor) or combination of an ALK5 inhibitor with an FGF pathway inhibitor (e.g., an FGF receptor inhibitor) allows for:

maintenance of pluripotency of cells with new functional properties that are defined below and are significantly different from the conventional human embryonic stem cells or induced pluripotent stem cells described previously (e.g. in U.S. Pat. Nos. 5,843; 6,200,806; and 7,029,913) and more similar to mESC characteristics; and greatly improved efficiency and stability of cells compared to, for example, methods for maintaining pluripotency known previously (e.g., involving GSK3 and MEK inhibitors—see, WO2008/015418). Indeed, it is surprising that an inhibitor of ALK5 is effective in improving maintenance of pluripotency in part because the art to date has focused on agonizing, not antagonizing, the TGFβ pathway to stimulate pluripotency. See, e.g., WO 2008/056173.

The invention provides in part for cell cultures comprising an ALK5 inhibitor (or other TGFβ/activin pathway inhibitor) and an MAPK inhibitor or a FGF signaling pathway inhibitor, optionally comprising a mammalian cell that is already pluripotent or that is to be, or has been, induced to pluripotency in the presence of the inhibitors. Optionally, the cell cultures can also include a GSK3β inhibitor and/or Leukemia Inhibitory Factor (LIF). Other media components and conditions can be as generally known in the art and can include, e.g., basal media components, vitamins, minerals, etc.

The ability to maintain cells in pluripotency allows for study and use of such cells in many ways that would otherwise be impossible. For example, many pluripotent stems cells quickly differentiate or die in culture and therefore do not allow for screening assays, genetic engineering, and other uses where it is necessary or convenient to maintain pluripotency for a certain time period or through multiple cell passages (e.g., cell divisions). The present invention allows for one to circumvent such problems.

II. Cultures

Cell cultures are provided that include an ALK5 inhibitor (or other TGFβ/activin pathway inhibitor), optionally with a MAPK (e.g., a MEK or Erk or p38 inhibitor) or FGF signaling pathway inhibitor (e.g., an FGF receptor inhibitor) and, to induce or maintain pluripotency of a mammalian cell. In some embodiments, the cells cultured with such inhibitors have the characteristics described in the examples, including but not limited to, forming domed colonies in cultures, expression of ESC markers (e.g., Oct4, Sox2, and Nanog), having nearly complete demethylation of the Oct4 promoter, expressing Rex-1 and ALP (e.g., markers of ESCs and early Epiblasts that are absent in post-implantation stage Epiblasts and EpiSCs), the ability to differentiate in vitro into endoderm, neuroectoderm, and mesoderm as well as in vivo pluripotency characteristics such as the ability to form teratoma (e.g., in SCID mice) and for non-human cells, the ability to form chimeric progeny when injected into blastocysts and implanted into a receptive uterus. Moreover, in some embodiments, the cells in the cultures retain such characteristics for multiple cell passages, e.g., at least 1, 2, 3, 4, 5, 7, 10, 20, 30, or more while in the same culture conditions.

The cell cultures can optionally also include one or both of a GSk3β inhibitor and LIF. As explained in the examples, the presence of LIF can in some embodiments improve long-term maintenance of pluripotent cells (e.g., over more than 10 passages) and thus a sufficient amount of LIF can be included in the cultures to allow for long-term maintenance of pluripotency. Further, with or without LIF, a sufficient amount of a GSK3β inhibitor can also be included. In some embodiments, the amount of the GSK3β inhibitor is sufficient to improve efficiency of the culture, i.e., the number of positive pluripotent colonies that are formed.

The amount of each inhibitor can vary and be determined for optimum advantage depending on the precise culture conditions, specific inhibitors used, and type of cell cultured. In some embodiments, the cultures of the invention include 0.05-10 µM, e.g., 0.1-1 µM, e.g., 0.5 µM of an ALK5 inhibitor (e.g., A-83-01, and 0.1~20 µM, e.g., 2~10 µM of SB431542). The inventors have found that TGF-β RI Kinase Inhibitor II [2-(3-(6-Methylpyridin-2-yl)-1H-pyrazol-4-yl)-1,5-naphthyridine] can be used as an ALK5 inhibitor, as described herein, for example at a concentrations of about 1.5 µM. Thus in some embodiments, cultures of the invention include 0.05-20 µM, e.g., 0.1-10 µM of TGF-β RI Kinase Inhibitor II. In some embodiments, the cultures of the invention include 10 nM-5 µM, e.g., 50 nM-1 µM of an FGF pathway inhibitor (e.g., PD173074). In some embodiments, the cultures of the invention include 0.05-50 µM, e.g., 0.1-5 µM, e.g., 0.5 µM of a MEK inhibitor (e.g., PD0325901). In some embodiments, the cultures of the invention include 0.05-20 µM, e.g., 0.5-5 µM, e.g., 3 µM of a GSK3β inhibitor (e.g., CHIR99021).

TGF β receptor (e.g., ALK5) inhibitors can include antibodies to, dominant negative variants of and antisense nucleic acids that target TGF β receptors (e.g., ALK5). Exemplary TGFβ receptor/ALK5 inhibitors include, but are not limited to, SB431542 (see, e.g., Inman, et al., *Molecular Pharmacology* 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al., *Cancer Science* 96(11):791-800 (2005), and commercially available from, e.g., Toicris Bioscience); TGF-β RI Kinase Inhibitor II [2-(3-(6-Methylpyridin-2-yl)-1H-pyrazol-4-yl)-1,5-naphthyridine]; 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (-{4-[3-(pyridin-2-yl)-1H-pyrazol-4-yl]pyridin-2-yl}-N-(tetrahydro-2H-pyran-4-yl)benzamide) (see, e.g., Gellibert, et al., *Journal of Medicinal Chemistry* 49(7):2210-2221 (2006)), SM16 (see, e.g., Suzuki, et al., *Cancer Research* 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim, et al., *Xenobiotica* 38(3):325-339 (2008)), GW6604 (2-phenyl-4-(3-pyridin-2-yl-1H-pyrazol-4-yl)pyridine) (see, e.g., de Gouville, et al., *Drug News Perspective* 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., *Molecular Pharmacology* 65(3):744-752 (2004)) and pyrimidine derivatives (see, e.g., those listed in Stiefl, et al., WO2008/006583, herein incorporated by reference). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e. reprogramming) process.

In view of the data herein showing the effect of inhibiting ALK5, it is believed that inhibition of the TGFβ/activin pathway will have similar effects. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGFβ receptor inhibitors can include antibodies to, dominant negative variants of and antisense nucleic acids that target TGFβ receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGFβ receptors. (See, e.g., Wrzesinski, et al., *Clinical Cancer Research* 13(18):5262-5270 (2007); Kaminska, et al., *Acta Biochimica Polonica* 52(2):329-337 (2005); and Chang, et al., *Frontiers in Bioscience* 12:4393-4401 (2007).)

Inhibitors of SMAD 2/3 phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., *Oncogene* 26:3311-3320 (2007); and Kataoka, et al., EP1992360, incorporated herein by reference.)

Inhibitors of the interaction of SMAD 2/3 and smad4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., *Oncogene* 24:3864-3874 (2005) and Zhao, et al., *Molecular Biology of the Cell*, 17:3819-3831 (2006).)

Inhibitors of MEK can include antibodies to, dominant negative variants of and antisense nucleic acids that target MEK. Specific examples of MEK inhibitors include, but are not limited to, PD0325901, (see, e.g., Rinehart, et al., *Journal of Clinical Oncology* 22: 4456-4462 (2004)), PD98059 (available, e.g., from Cell Signaling Technology), U0126 (available, for example, from Cell Signaling Technology), SL 327 (available, e.g., from Sigma-Aldrich), ARRY-162 (available, e.g., from Array Biopharma), PD184161 (see, e.g., Klein, et al., *Neoplasia* 8:1-8 (2006)), PD184352 (CI-1040) (see, e.g., Mattingly, et al., *The Journal of Pharmacology and Experimental Therapeutics* 316: 456-465 (2006)), sunitinib (see, e.g., Voss, et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluate in Phase I and II clinical trials for cancer (see, e.g., Rinehart, et al., *Journal of Clinical Oncology* 22(22):4456-4462 (2004)). Other MEK inhibitors being evaluated in clinical trials include PD184352 (see, e.g., English, et al., *Trends in Pharmaceutical Sciences* 23(1):40-45 (2002)), BAY 43-9006 (see, e.g., Chow, et al., *Cytometry (Communications in Clinical Cytometry)* 46:72-78 (2001)), PD-325901 (also PD0325901), GSK1120212, ARRY-438162, RDEA119, AZD6244 (also ARRY-142886 or ARRY-886), R05126766, XL518 and AZD8330 (also ARRY-704). (See, e.g., information from the National Institutes of Health located on the World Wide Web at clinicaltrials.gov as well as information from the Nation Cancer Institute located on the World Wide Web at cancer.gov/clinicaltrials.

p38 (also known as CSBP, mHOG1, RK and SAPK2) inhibitors can include antibodies to, dominant negative variants of and antisense nucleic acids that target p38. Specific examples of inhibitors include but are not limited to SB203580 (4-(4-Fluorophenyl)-2-(4-methylsulfinylphenyl)-5-(4-pyridyl)1H-imidazole); SB202190 (4-(4-fluorophenyl)-2-(4-hydroxyphenyl)-5(4-pyridyl)-1H-imidazole); SB 220025; N-(3-tert-butyl-1-methyl-5-pyrazolyl)-N'-(4-(4-pyridinylmethyl)phenyl)urea; RPR 200765A; UX-745; UX-702; UX-850; SC10-469; RWJ-67657 (RW Johnson Pharmaceutical Research Institute); RDP-58 (SangStat Medical Corp.; acquired by Genzyme Corp.); Scios-323 (SCIO 323; Scios Inc.); Scios-469 (SCIO-469; Scios Inc.); MKK3/MKK6 inhibitors (Signal Research Division); p38/MEK modulators (Signal Research Division); SB-210313 analogs; SB-238039; HEP-689 (SB 235699); SB-239063; SB-239065; SB-242235 (SmithKline Beecham Pharmaceuticals); VX-702 and VX-745 (Vertex Pharmaceuticals Inc.); AMG-548 (Amgen Inc.); Astex p38 kinase inhibitors (Astex Technology Ltd.); RPR-200765 analogs (Aventis SA); Bayer p38 kinase inhibitors (Bayer Corp.); BIRB-796 (Boehringer Ingelheim Pharmaceuticals Inc.); Celltech p38 MAP kinase inhibitor (Celltech Group plc.); FR-167653 (Fujisawa Pharmaceutical Co. Ltd.); SB-681323 and SB-281832 (GlaxoSmithKline plc); LEO Pharmaceuticals MAP kinase inhibitors (LEO Pharma A/S); Merck Co. p38 MAP kinase inhibitors (Merck research Laboratories); SC-040 and SC-XX906 (Monsanto Co.); adenosine A3 antagonists (Novartis AG); p38 MAP kinase inhibitors (Novartis Pharma AG); CNI-1493 (Picower Institute for Medical Research); RPR-200765A (Rhone-Poulenc Rorer Ltd.); and Roche p38 MAP kinase inhibitors (e.g., R03201195 and R04402257; Roche Bioscience). See, e.g., Roux, et al., *Microbiology and Molecular Biology Reviews* 68(2):320-344 (2004); Engelman, et al., *Journal of Biological Chemistry* 273(48):32111-32120 (1998); Jackson, et al., *Journal of Pharmacology and Experimental Therapeutics* 284(2): 687-692 (1998); Kramer, et al., *Journal of Biological Chemistry* 271(44):27723-27729 (1996); and Menko, et al., US20080193504.

Additional inhibitors of p38 include but are not limited to 1,5-diaryl-substituted pyrazole and substituted pyrazole compounds (U.S. Pat. No. 6,509,361 and U.S. Pat. No. 6,335,336); substituted pyridyl compounds (US20030139462); quinazoline derivatives (U.S. Pat. No. 6,541,477, U.S. Pat. No. 6,184,226, U.S. Pat. No. 6,509,363 and U.S. Pat. No. 6,635,644); aryl ureas and heteroaryl analogues (U.S. Pat. No. 6,344,476); heterocyclic ureas (WO1999/32110); other urea compounds (WO1999/32463, WO1998/52558, WO1999/00357 and WO1999/58502); and substituted imidazole compounds and substituted triazole compounds (U.S. Pat. No. 6,560,871 and U.S. Pat. No. 6,599,910).

Inhibitors of Erk can include antibodies to, dominant negative variants of and antisense nucleic acids that target Erk. Specific examples of Erk inhibitors include but are not limited to PD98059 (see, e.g., Zhu, et al., *Oncogene* 23:4984-4992 (2004)), U0126 (see, Zhu, supra), FR180204 (see, e.g., Ohori, *Drug News Perspective* 21(5):245-250 (2008)), sunitinib (see, e.g., Ma, et al., US2008004287 incorporated herein by reference), sorafenib (see, Ma, supra), Vandetanib (see, Ma, supra), pazopanib (see, Ma, supra), Axitinib (see, Ma, supra) and PTK787 (see, Ma, supra). Erk inhibitors can include molecules that inhibit Erk alone or that also inhibit a second target as well. For example, in some embodiments, the Erk inhibitor is:

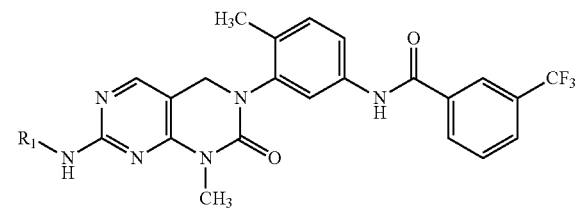

in which:
$R_1$ is selected from hydrogen, $C_{1-6}$alkyl, $C_{2-6}$alkenyl, $C_{6-10}$aryl-$C_{0-4}$alkyl, $C_{5-10}$heteroaryl-$C_{0-4}$-alkyl, $C_{3-10}$cycloalkyl-$C_{0-4}$alkyl and $C_{3-10}$heterocycloalkyl-$C_{0-4}$alkyl; wherein any alkyl or alkenyl of $R_1$ is optionally substituted by one to three radicals independently selected from halo, hydroxy, $C_{1-6}$alkyl and —$NR_2R_3$; wherein any aryl, heteroaryl, cycloalkyl or heterocycloalkyl of $R_1$ is optionally substituted by one to three radicals selected from halo, hydroxy, cyano, $C_{1-6}$alkyl, $C_{1-6}$alkoxy, $C_{2-6}$alkenyl, halo-substituted-alkyl, halo-substituted-alkoxy, —$XNR_2R_3$, —$XOXNR_2R_3$, —$XNR_2S(O)_{0-2}R_3$, —$XC(O)NR_2R_3$, —$XNR_2C(O)XOR_2$, —$XNR_2C(O)NR_2R_3$, —$XNR_2XNR_2R_3$, —$XC(O)NR_2XNR_2R_3$, —$XNR_2XOR_2$, —$XOR_2$, —$XNR_2C(=NR_2)NR_2R_3$, —$XS(O)_{0-2}R_4$, —$XNR_2C(O)R_2$, —$XNR_2C(O)XNR_2R_3$, —$XNR_2C(O)R_4$, —$XC(O)R_4$, —$XR_4$, —$XC(O)OR_3$ and —$XS(O)_{0-2}NR_2R_3$; wherein X is a bond or $C_{1-4}$alkylene; $R_2$ and $R_3$ are independently selected from hydrogen, $C_{1-6}$alkyl and $C_{3-12}$cycloalkyl; and $R_4$ is $C_{3-10}$heterocycloallyl optionally substituted with 1 to 3 radicals selected from $C_{1-6}$alkyl, —$XNR_2R_3$, —$XNR_2XNR_2R_2$, $XNR_2XOR_2$ and —$XOR_2$; wherein X, $R_2$ and $R_3$ are as described above; and the N-oxide derivatives, prodrug derivatives, protected derivatives, individual isomers and mixture of isomers thereof; and the pharmaceutically acceptable salts and solvates (e.g. hydrates) of such compounds or as otherwise described in WO 06/135824.

Inhibitors of the FGF signaling pathway include, but are not limited to FGF receptor inhibitors. FGF receptor (FGFR) inhibitors can include antibodies to, dominant negative variants of and antisense nucleic acids that target FGFR. Specific examples of FGFR inhibitors include, but are not limited to, SU6668 (see, e.g., Klenke, *BMC Cancer* 7:49 (2007)), SU5402 (3-[3-(2-Carboxyethyl)-4-methylpyrrol-2-methylidenyl]-2-indolinone) and PD173074 (see, e.g., Bansal, et al., *J. Neuro. Res.* 74(4):486-493 (2003)).

Inhibitors of GSK3 can include antibodies to, dominant negative variants of and antisense nucleic acids that target GSK3. Specific examples of GSK3 inhibitors include, but are not limited to, CHIR99021, CHIR98014, AR-A014418 (see, e.g., Gould, et al., *The International Journal of Neuropsychopharmacology* 7:387-390 (2004)), CT 99021 (see, e.g., Wagman, *Current Pharmaceutical Design* 10:1105-1137 (2004)), CT 20026 (see, Wagman, supra), SB216763 (see, e.g., Martin, et al., *Nature Immunology* 6:777-784 (2005)), AR-A014418 (see, e.g., Noble, et al., *PNAS* 102: 6990-6995 (2005)), lithium (see, e.g., Gould, et al., *Pharmacological Research* 48: 49-53 (2003)), SB 415286 (see, e.g., Frame, et al., *Biochemical Journal* 359:1-16 (2001)) and TDZD-8 (see, e.g., Chin, et al., *Molecular Brain Research*, 137(1-2):193-201 (2005)). Further exemplary GSK3 inhibitors available from Calbiochem (see, e.g., Dalton, et al., WO2008/094597, herein incorporated by reference), include but are not limited to BIO (2'Z,3'£)-6-Bromoindirubin-3'-oxime (GSK3 Inhibitor IX); BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWSI 19 pyrrolopyrimidine compound (GSK3beta Inhibitor XII); L803 H-KEAPPAPPQSpP-NH$_2$ (SEQ ID NO:1) or its Myristoylated form (GSK3beta Inhibitor XIII); 2-Chloro-1-(4,5-dibromo-thiophen-2-yl)-ethanone (GSK3beta Inhibitor VI); AR-AO144-18; SB216763; and SB415286. Residues of GSK3b that interact with inhibitors have been identified. See, e.g., Bertrand et al., *J. Mol Biol.* 333(2): 393-407 (2003).

Where inhibitors of a particular gene product are described herein, it should be understood that the inhibitor can be replaced with an siRNA targeting the gene encoding the gene product. For example, the present invention provides for use of an siRNA that inhibits expression of ALK5 in place of an ALK5 inhibitor. Similarly, MEK inhibitors, Erk inhibitors, p38 inhibitors, FGF receptor inhibitors and GSK3β inhibitors can be replaced with a MEK siRNA, Erk siRNA, p38 siRNA, FGF receptor siRNA and GSK3β siRNA, respectively. Further, an inhibitory antibody (e.g., a humanized or chimeric antibody) can be used as an inhibitor of ALK5, MEK, Erk, p38, FGF receptor, and GSK3β.

In some embodiments, cells are initially cultured with an epigenetic modifier followed by a culturing step lacking the modifier but including the inhibitors described herein (e.g., and AKL5 inhibitor, MEK inhibitors, Erk inhibitors, p38 inhibitors, FGF receptor inhibitors and GSK3β inhibitors, Leukemia inhibiting Factor (LIF), etc.). Exemplary epigenetic modulators include an inhibitor of histone H3K4 demethylation or an activator of H3K4 methylation. Exemplary epigenetic modifiers include, e.g., histone demethylase inhibitors such as LSD1 inhibitors (e.g., parnate) or MAO inhibitors.

The terms "histone deacetylase inhibitor," "inhibitor of histone deacetylase" and "HDAC inhibitor" refer to a compound capable of interacting with a histone deacetylase and inhibiting its enzymatic activity. "Inhibiting histone deacetylase enzymatic activity" means reducing the ability of a histone deacetylase to remove an acetyl group from a histone. In some embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Some representative HDAC inhibitors include butyric acid, MS-27-275, SAHA, Trichostatin A, apicidin, oxanflatin, FK228, and trapoxin. These inhibitors can be divided into several classes based on their structures, including short-chain fatty acids (butyrates and Valproic acid), hydroxamic acids (Trichostatin A and SAHA), cyclic tetrapeptides (depsipeptide), benzamides (MS-27-275), and epoxide-containing agents (trapoxin). Most of them inhibit HDACs in a reversible manner except trapoxin, which possesses an epoxide group capable of irreversibly alkylating HDACs. The reversible inhibitors generally have a long aliphatic tail containing a nucleophilic end, such as —SH or —OH, which interacts with the active zinc center located on the bottom of HDAC binding pocket. Other HDAC inhibitors are emerging based on modification of the listed structures. Most of the new agents are derivatives of hydroxamic acids, including amide analogues of Trichostatin A (TSA) and thio/phosphorus-based SAHA. Replacement of the amide linkage in MS-27-275 structure with a sulfonamide led to discovery of a new class of potent HDAC inhibitors. Promising HDAC inhibitors that have entered clinical trials include hydroxamic acid derivative LAQ824, butyric acid derivative Titan, valproic acid, MS-27-275, SAHA, and depsipeptide FK228.

Histone demethylase inhibitors include inhibitors to lysine-specific demethylase I (LSD1; also known as lysine-specific histone demethylase, BHCl 10 and KIAA0601). International Patent Application No. WO 2006/071608 is directed to a method for monitoring eukaryotic histone demethylase activity, methods for up-regulating and down-regulating methylated histone-activated genes, and a method for treating or preventing a disease (e.g., a hyperproliferative disease such as cancer) by modulating the level of protein or the activity of a histone demethylase. In view of the importance of gene regulation, and the ability to affect gene regulation by inhibiting or modulating LSD1, inhibitors of the enzyme may have significant therapeutic potential; Bi, X. et al., Bioorg. Med. Chem. Lett. 16:3229-3232 (2006) and International Patent Application Nos. WO2007/021839 and WO2008/127734 describe certain compounds useful as inhibitors of LSD1.

The present invention also provides for a culture medium for maintaining pluripotency of cells. The cell culture media optionally does not include a cell. The culture medium can comprise the culture media contents described above, albeit with the cells. Such media is useful culturing cells as described herein.

As provided elsewhere herein, the cells in the cultures can be selected from embryonic stem cells (e.g., human embryonic stem cells (hESCs), primate embryonic stem cells, rat embryonic stem cells, or embryonic stem cells from other animals, optionally non-mouse embryonic stem cells). Alternatively, the cells include induced pluripotent stem cells (iPSCs). In some embodiments, the iPSCs are from humans, primates, rat, or mice, or other non-mouse animals. The iPSCs can be generated from non-pluripotent cells as recently as within the previous cell division or alternatively, the cells can have been maintained for 1, 2, 3, 4, 5, 7, 10, 20, or more cell divisions or passages previously as iPSCs. In other words, the cell cultures can contain iPSCs that were created previously (e.g., a week, a month, or more previously). One benefit of the small molecule combinations provided herein is that in addition and separate to their use in reprogramming, they allow one to maintain a desired pluripotency for what appears to be an indefinite period of time.

The present invention provides for pluripotent cells in a mixture with one or more inhibitor as described herein. In some embodiments, the compound is in the mixture at a concentration sufficient to induce or improve efficiency of induction to pluripotency. For example, in some embodiments, the compounds are in a concentration of at least 0.1 nM, e.g., at least 1, 10, 100, 1000, 10000, or 100000 nM, e.g., between 0.1 nM and 100000 nM, e.g., between 1 nM and 10000 nM, e.g., between 10 nM and 10000 nM, between 0.01 µM and 5 µM, between 0.1 µM and 5 µM. For example, A-83-01 can be used in a concentration of about 0.1 µM to about 0.5 µM, e.g., 0.25 µM to about 0.5 µM. In some embodiments, the concentration of A-83-01 is 0.25 µM. In some embodiments, the concentration of A-83-01 is 0.5 µM. CHIR99021 can be used in a concentration of about 3 µM. PD325901 can be used in a concentration of about 0.5 µM. PD173074 can be used in a concentration of about 0.1 µM. In some embodiments, the mixtures are in a synthetic vessel (e.g., a test tube, Petri dish, etc.). Thus, in some embodiments, the cells are isolated cells (not part of an animal). In some embodiments, the cells are isolated from an animal (human or non-human), placed into a vessel, contacted with one or more compound as described herein. The cells can be subsequently cultured and optionally, inserted back into the same or a different animal, optionally after the cells have been stimulated to become a particular cell type or lineage.

In some embodiments, the cells comprise an expression cassette for heterologous expression of at least one or more of an Oct polypeptide, a Myc polypeptide, a Sox polypeptide and a Klf polypeptide. In some embodiments, the cells do not include an expression cassette to express any of the Oct, Myc, Sox of Klf polypeptides. Cells with or without such expression cassettes are useful, for example, screening methods as described herein.

III. Cells

Cells can be pluripotent prior to initial contact with the inhibitors of the invention or the cells can be contacted with one or more of the inhibitors of the invention and then induced to pluripotency (e.g., by introduction of the appropriate transcription factors and/or by contact with the appropriate small molecules to induce pluripotency).

Any animal cells can be used in the methods of the invention. Thus, for example, in some embodiments, the cells are mammalian cells. Exemplary mammalian cells include, but are not limited to, human cells or non-human cells, including but not limited to rat, mouse (e.g., SCID or other mice), pig, bovine, ovine, canine, feline, and primate (e.g., rhesus monkey, chimpanzee, etc.).

Pluripotent cells used according to the methods of the invention can be either naturally-occurring stem cells or can be induced pluripotent cells. Exemplary naturally-occurring stem cells include, e.g., embryonic stem cells. Methods of isolating embryonic stems cells are well known. See, e.g., Matsui et al., Cell 70:841, 1992; Thomson et al., U.S. Pat. No. 5,843,780; Thomson et al., Science 282:114, 1998; Shamblott et al., Proc. Natl. Acad. Sci. USA 95:13726, 1998; Shamblott et al., U.S. Pat. No. 6,090,622; Reubinoff et al., Nat. Biotech. 18:399, 2000; PCT WO00/27995, Iannaccone et al., Dev. Biol. 163:288, 1994; Loring et al., PCT WO99/27076, Pain et al., Development 122:2339, 1996; U.S. Pat. No. 5,340,740; U.S. Pat. No. 5,656,479, Wheeler et al., Reprod. Fertil. Dev. 6:563, 1994; Shim et al., Biol. Reprod. 57:1089, 1997. In some embodiments, the stem cells are derived from a blastocyst (e.g., obtained from a blastocyst) that are subsequently cultured in the presence of at least an ALK5 inhibitor and an Erk or MEK inhibitor, optionally with other inhibitors as descried herein.

A number of ways have now been reported for inducing pluripotency in cells. Pluripotency can be induced, for example, by introduction of transcription factors or otherwise induce or mimic expression of certain transcription factors. In some embodiments, one or more of the following transcription factors are expressed endogenously or recombinantly (e.g., by introduction of heterologous expression cassettes expressing one or more transcription factors). Exemplary technologies for induction of pluripotency include, but are not limited to introduction of at least one or more expression cassette for expression of at least one of Oct3/4, Sox2, c-Myc, and Klf4 (see, e.g., Takahashi, Cell 131(5):861-872 (2007); Cell Stem Cell 2, 10-12 (2008)), optionally with one or more small molecules, including but not limited to, an agent that inhibits H3K9 methylation, e.g., a G9a histone methyltransferase such as BIX01294. See, e.g., Kubicek, et al., Mol. Cell 473-481 (2007).

The pluripotent cells of the invention can be characterized by several criteria. In addition to the gene expression, methylation, and in vitro and in vivo characteristics described herein, the pluripotent cells of the invention will maintain pluripotency over at least one (e.g., 1, 2, 3, 4, 5, 10, 20, etc.) cell divisions in the presence of leukemia inhibitory factor (LIF) and bone morphogenic protein (BMP) or, alternatively, under inhibition of the TGFβ and activin signaling pathway, inhibition of the MAPK signaling pathway, and optionally inhibition of the FGF pathway. For example, as described herein, animal cells (e.g., human and rat cells) contacted with an ALK5 inhibitor and MEK inhibitor were maintained in pluripotency through multiple divisions. Further, as described herein, inhibition of the TGFβ and activin signaling pathway (e.g., TGFβ signaling) in conjunction with inhibition of MEK, FGFR and GSK3 has strong reprogramming activity and can promote partial conversion of EpiSCs to a mESC-like state. In contrast, conventional hESCs, epiblast stem cells (EpiSCs) and human induced pluripotent cells cultured under conventional conditions differentiate when contacted with an inhibitor of ALK5. See, e.g., Saha, et al., *Biophys. J.* 94: 4123-4133 (2008). It has been reported that conventional hESCs, EpiSCs and human induced pluripotent cells cultured under conventional conditions appear dependent on MAPK, FGF, and TGFβ/Activin/Nodal pathway activity for self-renewal, and differentiate rapidly when treated with MEK, FGFR and/or ALK4/5/7 inhibitors (Brons et al., Nature 448, 191-195, 2007; Li et al., Differentiation 75, 299-307, 2007; Peerani et al., EMBO J. 26, 4744-4755, 2007; Tesar et al., Nature 448, 196-199, 2007). In addition, the inventors have found that the cells of the invention (e.g., human or rat cells cultured as described in the examples) maintain pluripotency (i.e., do not differentiate) in the presence of an inhibitor of the FGF signaling pathway (e.g., PD173074). In contrast, hESCs, EpiSCs and human induced pluripotent cells cultured under conventional conditions differentiate when contacted with PD173074. Notably, mESCs do not differentiate when contacted with PD173074. Thus, the cells of the present invention (e.g., cultured as described herein) are in a state more similar to mESCs than conventionally-cultured hESCs, EpiSCs and human induced pluripotent cells. Similar to mESCs, the cells of the present invention have more compact and domed colony morphology, while conventionally-cultured hESCs, EpiSCs and human induced pluripotent cells have flat colony morphology. Like mESCs, the cells of the present invention have the ability to give rise to all cell types in vitro, and contribute to an entire animal in vivo, including germline, when placed back into blastocyts. In contrast, conventionally-cultured hESCs, EpiSCs and human induced pluripotent cells are incapable of incorporating into the inner cell mass (ICM) and contributing to chimerism. It will be appreciated that other animal cells aside from rat and human can be generated with similar characteristics using the methods described herein. Exemplary additional animal cells include e.g., dogs, cats, pigs, cows, sheep, goats, monkeys and chimpanzees.

Certain markers are helpful to distinguish the cells of the present invention from conventionally-cultured hESCs, EpiSCs and human induced pluripotent cells. For example, Stra8, Dppa3, Gbx2, Pecam1, and Klf4 express at a higher level in the human cells of the present invention as compared to their expression levels in conventionally-cultured hESCs, epiSCs and human induced pluripotent cells. In contrast, many lineage specific genes, e.g., Foxa2, Otx2, Lefty1, Gata6, Sox17, Cer1, express at a higher level in epiSCs and conventional human ES cells, as compared to their expression levels in the cells of the present invention. Conventionally-cultured human iPSC or ESC cells differentiate when treated with MEK, FGFR and/or ALK4/5/7 inhibitors (Brons et al., *Nature* 448, 191-195, 2007; Li et al., *Differentiation* 75, 299-307, 2007; Peerani et al., *EMBO J* 26, 4744-4755, 2007; Tesar et al., *Nature* 448, 196-199, 2007).

In particular, Gbx2, Dppa3 and Klf4 are useful marker to characterize the pluripotent animal cells of the invention. These markers are highly expressed in the pluripotent cells of the invention. For example, in some embodiments, the cells of the present invention express these markers at a level that is at least 2-fold of their level in conventionally-cultured hESCs, EpiSCs and human induced pluripotent cells, e.g., Hues9 cells (hES facility, Harvard University, http://mcb-.harvard.edu/melton/hues/). In some embodiments, the expression levels of these markers in the pluripotent cells of the invention are at least 2-fold, 2.5-fold, 3-fold, 4-fold, 5-fold or higher. Other useful markers include an ICM marker Rex1.

In some embodiments, Gbx2 is expressed in the pluripotent cells of the invention at a level that is at least 5-fold of that in Hues9 cells. In some embodiments, Klf4 is expressed in the pluripotent cells of the invention at a level that is at least 2.5-fold of that in Hues9 cells. In some embodiments, Dppa3 is expressed in the pluripotent cells of the invention at a level that is at least 2-fold of that in Hues9 cells.

Another useful marker for the pluripotent cells of the invention is E-cadherin. Without intending to limit the scope of the invention it is believed that E-cadherin plays a role in the pluripotency of the cells of the invention. In some embodiments, E-cadherin is expressed in the pluripotent cells of the invention at a level that is 2-fold of that in Hues9 cells.

Other typical pluripotent markers can be used for characterization of the cells of the invention, e.g., Oct4, Sox2, Nanog, SSEA-1, SSEA-3, SSEA4, TRA-1-61, TRA-1-81, and alkaline phosphatase (ALP). These typical pluripotent markers, or a subset of them, can be useful for distinguishing the pluripotent cells of the invention from conventionally-cultured hESCs, EpiSCs and human induced pluripotent cells.

Methods known in the art can be used to characterize the cells of the invention. Gene expression levels can be detected by, e.g., real-time PCR or real-time RT-PCR (e.g., to detect mRNA), and/or by western blot or other protein detection technique.

The pluripotent cells of the invention differentiate toward mesoderm lineages in response to BMP treatment. Conventionally-cultured hESCs, EpiSCs and human induced pluripotent cells, in contrast, generate trophoblasts or primitive endoderm cells (Brons et al., *Nature* 448, 191-195, 2007; D'Amour et al., *Nat Biotechnol* 23, 1534-1541, 2005; Xu et al., *Nat Biotechnol* 20, 1261-1264, 2002).

IV. Transformation

Where transformed cells are desired (e.g., to generate iPSCs or to express a desired protein or nucleic acid), the cells contacted with the inhibitors of the invention (e.g., ALK5 inhibitors, MAPK inhibitors, FGF pathway inhibitors, and optionally GSK3β inhibitors) can be transformed before the contacting and/or can be transformed following contacting. For example, one advantage of the present invention is that it allows for maintenance of pluripotent cells through multiple cell passage and therefore allows for manipulations and subsequent selection of progeny while maintaining the pluripotent characteristics of the cells. This is useful, inter alia, for generation of transgenic animals, including generation of knockout animals via sequence-specific recombination events as described herein.

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

In some embodiments, where positive expression of a protein is desired, the species of cell and protein to be expressed is the same. For example, if a mouse cell is used, a mouse ortholog is introduced into the cell. If a human cell is used, a human ortholog is introduced into the cell.

It will be appreciated that where two or more proteins are to be expressed in a cell, one or multiple expression cassettes can be used. For example, where one expression cassette is to express multiple polypeptides, a polycistronic expression cassette can be used.

A. Plasmid Vectors

In certain embodiments, a plasmid vector is contemplated for use to transform a host cell. In general, plasmid vectors containing replicon and control sequences which are derived from species compatible with the host cell are used in connection with these hosts. The vector can carry a replication site, as well as marking sequences which are capable of providing phenotypic selection in transformed cells.

B. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

i. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a ~36 kb, linear, double-stranded DNA virus, allows substitution of large pieces of adenoviral DNA with foreign sequences up to 7 kb (Grunhaus et al., Seminar in Virology, 200(2):535-546, 1992)).

ii. AAV Vectors

The nucleic acid may be introduced into the cell using adenovirus assisted transfection. Increased transfection efficiencies have been reported in cell systems using adenovirus coupled systems (Kelleher and Vos, Biotechniques, 17(6): 1110-7, 1994; Cotten et al., Proc Natl Acad Sci USA, 89(13):6094-6098, 1992; Curiel, Nat Immun, 13(2-3):141-64, 1994.). Adeno-associated virus (AAV) is an attractive vector system as it has a high frequency of integration and it can infect non-dividing cells, thus making it useful for delivery of genes into mammalian cells, for example, in tissue culture (Muzyczka, Curr Top Microbiol Immunol, 158:97-129, 1992) or in vivo. Details concerning the generation and use of rAAV vectors are described in U.S. Pat. Nos. 5,139,941 and 4,797,368, each incorporated herein by reference.

iii. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller et al., Am. J. Clin. Oncol., 15(3):216-221, 1992).

In order to construct a retroviral vector, a nucleic acid (e.g., one encoding gene of interest) is inserted into the viral genome in the place of certain viral sequences to produce a virus that is replication-defective. To produce virions, a packaging cell line containing the gag, pol, and env genes but without the LTR and packaging components is constructed (Mann et al., Cell, 33:153-159, 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986; Mann et al., Cell, 33:153-159, 1983). The media containing the recombinant retroviruses is then collected, optionally concentrated, and used for gene transfer. Retroviral vectors are able to infect a broad variety of cell types. However, integration and stable expression typically involves the division of host cells (Paskind et al., Virology, 67:242-248, 1975).

Lentiviruses are complex retroviruses, which, in addition to the common retroviral genes gag, pol, and env, contain other genes with regulatory or structural function. Lentiviral vectors are well known in the art (see, for example, Naldini et al., Science, 272(5259):263-267, 1996; Zufferey et al., Nat Biotechnol, 15(9):871-875, 1997; Blomer et al., J. Virol., 71(9):6641-6649, 1997; U.S. Pat. Nos. 6,013,516 and 5,994, 136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

iv. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., Proc. Nat'l Acad. Sci. USA, 86:9079-9083, 1989). Using antibodies against major histocompatibility complex class I and class II antigens, they demonstrated the infection of a variety of human cells that bore those surface antigens with an ecotropic virus in vitro (Roux et al., 1989).

C. Vector Delivery and Cell Transformation

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art. Such methods include, but are not limited to, direct delivery of DNA such as by ex vivo transfection (Wilson et al., *Science*, 244:1344-1346, 1989, Nabel and Baltimore, *Nature* 326: 711-713, 1987), optionally with Fugene6 (Roche) or Lipofectamine (Invitrogen), by injection (U.S. Pat. Nos. 5,994, 624, 5,981,274, 5,945,100, 5,780,448, 5,736,524, 5,702,932, 5,656,610, 5,589,466 and 5,580,859, each incorporated herein by reference), including microinjection (Harland and Weintraub, *J. Cell Biol.*, 101:1094-1099, 1985; U.S. Pat. No. 5,789,215, incorporated herein by reference); by electroporation (U.S. Pat. No. 5,384,253, incorporated herein by reference; Tur-Kaspa et al., *Mol. Cell. Biol.*, 6:716-718, 1986; Potter et al., *Proc. Nat'l Acad. Sci. USA*, 81:7161-7165, 1984); by calcium phosphate precipitation (Graham and Van Der Eb, *Virology*, 52:456-467, 1973; Chen and Okayama, *Mol. Cell. Biol.*, 7(8):2745-2752, 1987; Rippe et al., *Mol. Cell. Biol.*, 10:689-695, 1990); by using DEAE-dextran followed by polyethylene glycol (Gopal, *Mol. Cell. Biol.*, 5:1188-1190, 1985); by direct sonic loading (Fechheimer et al., *Proc. Nat'l Acad. Sci. USA*, 84:8463-8467, 1987); by liposome mediated transfection (Nicolau and Sene, *Biochim. Biophys. Acta*, 721:185-190, 1982; Fraley et al., *Proc. Nat'l Acad. Sci. USA*, 76:3348-3352, 1979; Nicolau et al., *Methods Enzymol.*, 149:157-176, 1987; Wong et al., *Gene*, 10:87-94, 1980; Kaneda et al., *Science*, 243:375-378, 1989; Kato et al., *J Biol. Chem.*, 266:3361-3364, 1991) and receptor-mediated transfection (Wu and Wu, *Biochemistry*, 27:887-892, 1988; Wu and Wu, *J. Biol. Chem.*, 262: 4429-4432, 1987); each incorporated herein by reference); and any combination of such methods.

V. Culturing of Cells

Pluripotent cells, including embryonic stem cells and cells induced, or to be induced, to pluripotency can be cultured according to any method known in the art. As described herein, in some embodiments, pluripotent cells are cultured with an ALK5 inhibitor and one of a MEK or Erk inhibitor, optionally with a GSK3β inhibitor and/or LIF. Culture media can include any other component of culture media as known in the art. In some embodiments, the culture media include basal media components for cell survival (e.g., vitamins and minerals, optionally in an isotonic condition). An exemplary basal media is DMEM or a variation thereof, such as DMEM Knockout. The culture can further be supplemented with Knock-out serum replacement (KSP). The cultures of the invention can include one or more carbon sources. In some embodiments, the cultures comprise L-analyl-L-glutamine. The cultures can include serum or can be serum-free.

In some embodiments, the cells are cultured in contact with feeder cells. Exemplary feeder cells include, but are not limited to fibroblast cells, e.g., mouse embryonic fibroblast (MEF) cells, or x-ray inactivated CF1 feeder cells. Methods of culturing cells on feeder cells is known in the art.

In some embodiments, the cells are cultured in the absence of feeder cells. Cells, for example, can be attached directly to a solid culture surface (e.g., a culture plate), e.g., via a molecular tether. The inventors have found that culturing cells induced to pluripotency have a much greater efficiency of induction to pluripotency (i.e., a greater portion of cells achieve pluripotency) when the cells are attached directly to the solid culturing surface compared the efficiency of otherwise identically-treated cells that are cultured on feeder cells. Exemplary molecular tethers include, but are not limited to, matrigel, an extracellular matrix (ECM), ECM analogs, laminin, fibronectin, or collagen. Those of skill in the art however will recognize that this is a non-limiting list and that other molecules can be used to attach cells to a solid surface. Methods for initial attachment of the tethers to the solid surface are known in the art.

VI. Uses for Pluripotent Cells

The present invention allows for the further study and development of stem cell technologies, including but not limited to, prophylactic or therapeutic uses. For example, in some embodiments, cells of the invention (either pluripotent cells cultured in the inhibitors of the invention or cells derived from such cells and induced to differentiate along a desired cell fate) are introduced into individuals in need thereof, including but not limited to, individuals in need of regeneration of an organ, tissue, or cell type. In some embodiments, the cells are originally obtained in a biopsy from an individual; induced into pluripotency as described herein, optionally induced to differentiate (for examples into a particular desired progenitor cell) and then transplanted back into the individual. In some embodiments, the cells are genetically modified prior to their introduction into the individual.

In some embodiments, the pluripotent cells generated according to the methods of the invention are subsequently induced to form, for example, hematopoietic (stem/progenitor) cells, neural (stem/progenitor) cells (and optionally, more differentiated cells, such as subtype specific neurons, oligodendrocytes, etc), pancreatic cells (e.g., endocrine progenitor cell or pancreatic hormone-expressing cells), hepatocytes, cardiovascular (stem/progenitor) cells (e.g., cardiomyocytes, endothelial cells, smooth muscle cells), retinal cells, etc.

A variety of methods are known for inducing differentiation of pluripotent stem cells into desired cell types. A non-limiting list of recent patent publications describing methods for inducing differentiation of stem cells into various cell fates follows: U.S. Patent Publication No. 2007/0281355; 2007/0269412; 2007/0264709; 2007/0259423; 2007/0254359; 2007/0196919; 2007/0172946; 2007/0141703; 2007/0134215.

A variety of diseases may be ameliorated by introduction, and optionally targeting, of pluripotent cells of the invention to a particular injured tissue or tissue other tissue where pluripotent cells will generate a benefit. Examples of disease resulting from tissue injury include, but are not limited to, neurodegeneration disease, cerebral infarction, obstructive vascular disease, myocardial infarction, cardiac failure, chronic obstructive lung disease, pulmonary emphysema, bronchitis, interstitial pulmonary disease, asthma, hepatitis B (liver damage), hepatitis C (liver damage), alcoholic hepatitis (liver damage), hepatic cirrhosis (liver damage), hepatic insufficiency (liver damage), pancreatitis, diabetes mellitus, Crohn disease, inflammatory colitis, IgA glomerulonephritis, glomerulonephritis, renal insufficiency, decubitus, burn, sutural wound, laceration, incised wound, bite wound, dermatitis, cicatricial keloid, keloid, diabetic ulcer, arterial ulcer and venous ulcer.

In some embodiments, transgenic animals (e.g., non-human animals) are generated from pluripotent cells incubated with the inhibitors of the invention. Such cells can be transgenic cells, knockout lines (e.g., comprising one or more gene knockout introducing a selectable marker via site-specific recombination). Pluripotent cells incubated with the inhibitors as described herein can be introduced into a blastocyst from a compatible animal and subsequently introduced into a receptive uterus of an animal and resulting progeny can be selected for cells derived from the pluripotent cells (e.g., via a selectable marker or other phenotypic characteristics such as fur color). Chimeric progeny can be identified and lines can be established that pass the characteristics (e.g., a transgene) from the pluripotent cells to progeny. Homozygous animal lines can be established by breeding sibling animals.

The invention provides for generation of any type of transgenic animal according to the present methods. Exemplary animals include non-human mammals, and non-human primates. Exemplary animals include, e.g., mice (including SCID mice), rats, dogs, cats, pigs, cows, sheep, goats, monkeys and chimpanzees.

Culturing cells with the inhibitors of the invention, and thus maintaining pluripotency of the cells, conveniently allows for screening for cell phenotypes, drug responses, and also allows for screening of libraries of compounds or other agents (e.g., protein, nucleic acid, or antibodies) for the ability to modulate a pluripotent cell's phenotype or to induce a desired cellular response. Library screens can be designed to screen for a library member's ability to affect essentially any desired phenotype. Exemplary phenotypes can include, for example, cellular differentiation, apoptosis or other cell death, cell survival, death, or other phenotype in the presence of an additional compound or drug of interest, etc.

The agents in the library can be any small chemical compound, or a biological entity, such as a protein, sugar, nucleic acid or lipid. Typically, test agents will be small chemical molecules and peptides. Essentially any chemical compound can be used as a potential agent in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

EXAMPLES

Summary

Here, we report successful establishment of novel rat iPSCs (riPSCs), which can be homogenously maintained by LIF and a cocktail of ALK5 inhibitor, GSK3 inhibitor and MEK inhibitor. riPSCs share mouse ESC characteristics and most importantly can contribute extensively to chimaeras. We also generated novel human iPSCs (hiPSCs) with "mouse ESC-like" characteristics, which can be surprisingly maintained in culture in the presence of MEK inhibitor and ALK5 inhibitor. We propose that our experiments will provide a framework to generate pluripotent stem cells by reprogramming from rats or other species, whose authentic embryonic stem cells are still not available.

Example 1

This example demonstrates generation and maintenance of rat pluripotent cells.

Generation of Novel riPSCs from WB-F344 Cells by Oct41Klf41Sox2 Viral Transduction and Chemical Cocktails.

Figure 1B:
Figure 1C:
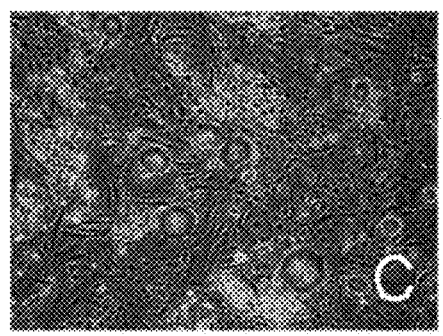
Figure 1D:
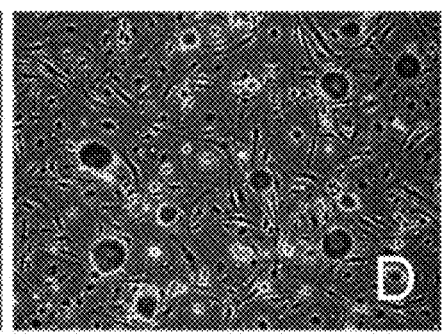
Figure 1E:
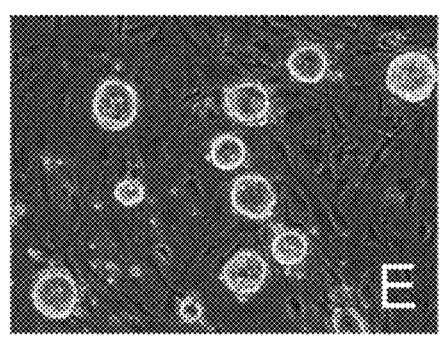
Figure 1F:
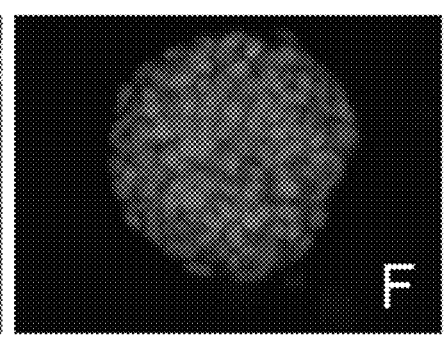
Figure 1G:
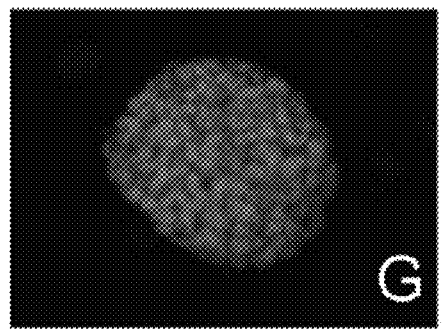
Figure 1H:
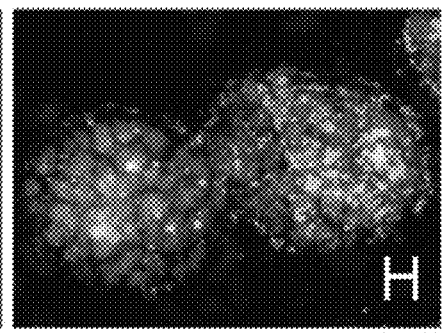
Figure 1I:
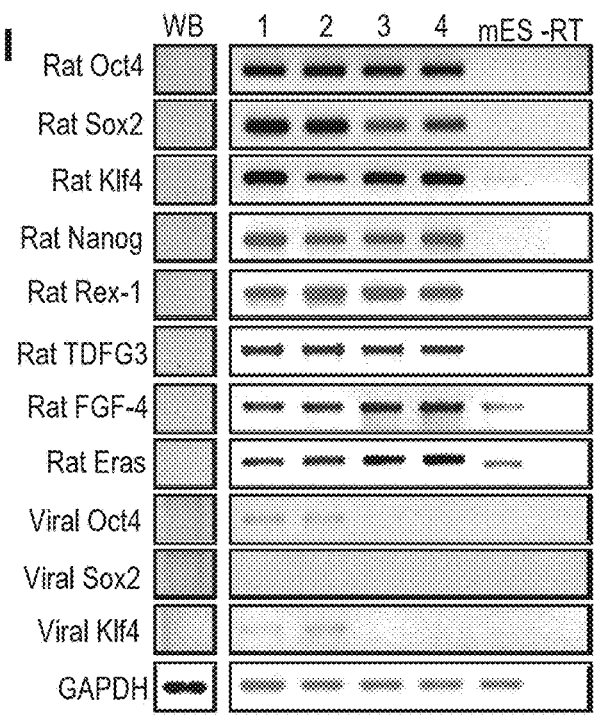
Figure 1J:
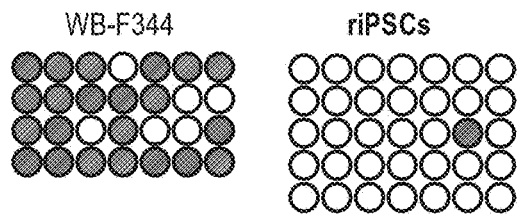
Figure 1K:
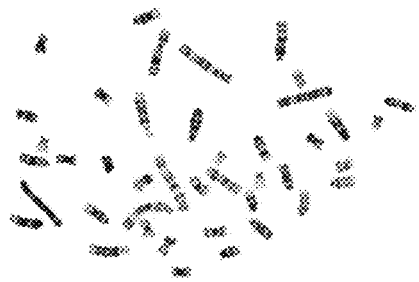
Figure 5A:
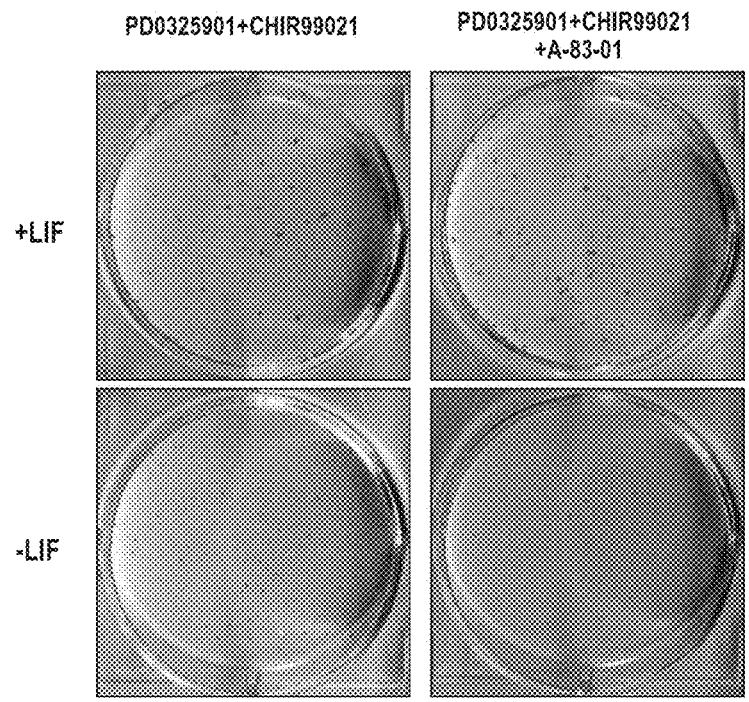
FIG. 5A-B. The effects of different small molecule combinations on maintaining the pluripotency of riPSCs in culture. riPSCs were trypsinized into single cells and seeded into 6-well plate at the density of 103 cells per well and treated with different inhibitor combinations. Five days latter, ALP staining was performed to visualize the riPSC colonies (A). The ALP positive colonies for each condition were counted from ten random 40× visual fields and the relative colony number was summarized in (B).
Figure 5B:
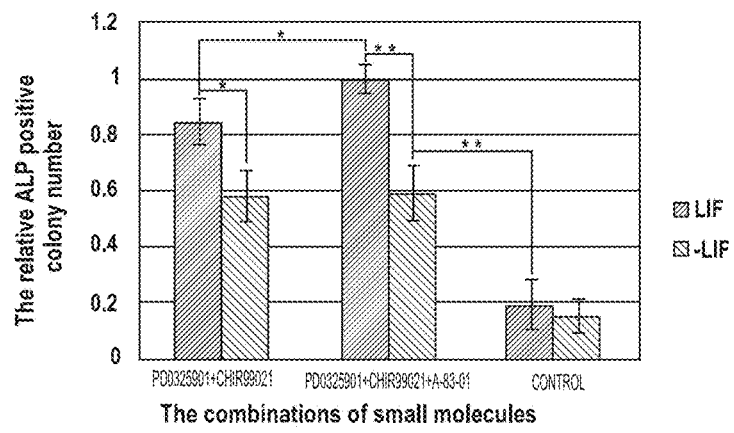

WB-F344, a diploid rat liver progenitor cell line (Grisham et al., *Proc Soc Exp Biol Med* 204, 270-279 (1993)), were transduced with Oct4, Sox2 and Klf4 by retroviruses and then split onto MEF feeder cells in the conventional mESC medium. Compact and alkaline phosphatase (ALP) positive ESC-like colonies were observed 10 days after transduction (the efficiency is about 0.4%) (FIG. 1A). When the ESC-like colonies were picked up and sub-cultured in the same medium, however, they quickly differentiated and lost ESC morphology (FIG. 1B), suggesting that the conventional mESC medium condition is not sufficient to maintain the pluripotency of riPSCs. Given the notion that small molecules can inhibit key differentiation-inducing pathways, we and others have previously identified and used small molecules to support mESC self-renewal in a more robust manner (Schugar et al., Gene Ther 15, 126-135 (2008); Xu et al., Nat Biotechnol 20, 1261-1264 (2002)). Based on such chemical strategy and the signaling differences for maintaining self-renewal of mESC and EpiSC/hESC, we selected MEK inhibitor PD0325901, ALK5 (the principle type I receptor of TGF β signaling) inhibitor A-83-01, GSK3β inhibitor CHIR99021, and FGFR inhibitor PD173074, and tested the effects of different small molecule combination on maintaining the pluripotency of riPSCs. Using combination of 0.5 µM PD0325901 and 3 µM CHIR99021, riPSCs can be short-term maintained in culture but showing extensive spontaneous differentiation (FIG. 1C). After serial passages, cells grown under this condition proliferated slower and the culture deteriorated due to the proliferation of differentiated cells. Recent studies demonstrated that PD0325901 combined with CHIR99021 and FGFR inhibitor PD173074 can maintain mESC pluripotency in a LIF independent manner (Ying et al., Cell 115, 281-292 (2003)). However, similar to the combination of PD0325901 and CHIR99021, including PD173074 (0.1 µM) in medium didn't show further benefit. Because Activin A/Nodal signaling is important to maintain the undifferentiated state of hESCs and EpiSCs, but dispensable for mESC self-renewal, we then tested whether the combination of PD0325901, CHIR99021 and the TGF-β inhibitor A-83-01 can suppress the differentiation and promote self-renewal of riPSCs. Interestingly, with the combination of 0.5 µM PD0325901, 3 µM CHIR99021 and 0.5 µM A-83-01, riPSCs grow as a more homogeneous population and the spontaneous differentiation was substantially inhibited (FIG. 1D). Under such condition, the clonal expansion efficiency was also significantly increased in comparison to the combination of PD0325901 and CHIR99021 (FIG. 5). Furthermore, although LIF itself was not sufficient to sustain riPSC self-renewal, only very small ALP positive colonies were observed and could not be long-term maintained in the absence of LIF (FIG. 5). Moreover, the unique chemical inhibitor cocktail was required for long term self-renewal of riPSCs. riPSCs have been cultured in the presence of LIF, PD0325901, A-83-01, and CHIR99021 for more than 30 passages without obvious differentiation and decrease in proliferation, but they lose ESC morphology and differentiate within one passage after the chemical inhibitors are removed from the medium. Under this condition, riPSCs are similar to the conventional mESCs in forming typical domed colonies in culture (FIG. 1E) Immunocytochemistry revealed that riPSCs express typical mESC markers, such as Oct4 (FIG. 1F), Sox2 (FIG. 1G), SSEA-1 (FIG. 1H, Green), Nanog (FIG. 1H Red), but are negative to the hESC markers, such as SSEA3, SSEA4 and TRA-1-81. RT-PCR analysis of four clonal riPSC lines using rat gene primers confirmed the expression of the endogenous rat Oct4, Sox2, Nanog, Klf4, Rex-1, TDGF2, FGF4 and Eras (FIG. 1I). By using the specific primers for transgenes, RT-PCR analysis revealed that the transduced mouse Oct4, Sox2 and Klf4 genes were largely silenced (FIG. 1I). Analysis of the methylation status of the rat Oct4 promoter showed differential methylation between riPSCs and WB-F344 cells. riPSC clones exhibited an almost complete demethylation pattern and is distinct from that of the parental WB-F344 cells (FIG. 1J). Notably, riPSCs share common molecular features with mESCs, especially express Rex-1 and ALP, markers of ESCs and early epiblasts that are absent in post-implantation stage epiblasts and EpiSCs.

The riPSCs are Pluripotent Stem Cells In Vitro and In Vivo.

To examine the developmental potential of riPSCs, in vitro differentiation assay was performed. Immunostaining showed riPSCs could differentiate into endoderm (Albumin and Pdx1) (FIG. 2A, 2B), neuroectoderm (βIII-tubulin, Tuj1) (FIG. 2C) and mesoderm (brachyury) (FIG. 2D) derivatives under standard embryoid body differentiation methods. Next, we examined riPSC's in vivo developmental potential. After transplanted into the Severe Combined Immunodeficient (SCID) mice, riPSCs formed teratoma, which consisted of all three germ layers including neuroepithelium-like structure (ectoderm), airway epithelium (endoderm), cartilage-like structure (mesoderm) and smooth muscle (mesoderm) (FIG. 2E~2H). Most remarkably, after injected into Brown-Norway rat (black fur) blastocysts (n=18), three rats were born and all exhibited extensive coat-color chimerism (FIG. 2I). However, no germline transmission has been detected yet. Taken together, the above results defined our riPSCs, distinct from rat EpiSCs, as a pluripotent mESC-like rat stem cell line.

Example 2

This example demonstrates culture media for inducing and maintaining human pluripotent cells in a state analogous to mouse embryonic stem cells.

Figure 3K:
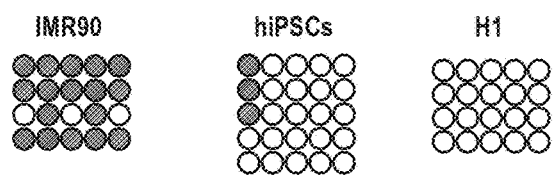
Figure 3L:
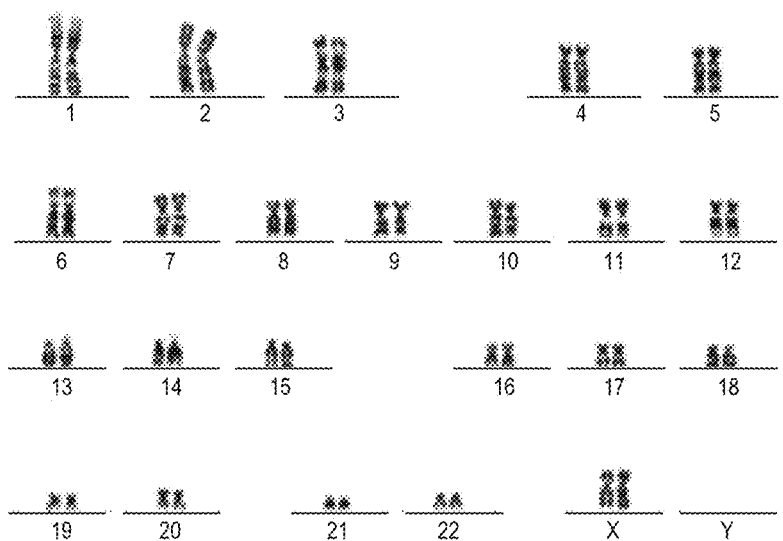

In contrast to mESCs, bFGF and TGFβ/Activin/Nodal signaling are essential for maintaining self-renewal of the conventional hESCs and EpiSCs. Inhibition of either TGFβ/Activin/Nodal or FGFR signals causes dramatic and rapid differentiation of hESCs and EpiSCs under the conventional hESC culture conditions. Recently, human induced pluripotent stem cells (hiPSCs) have been generated from fibroblasts by expression of either Oct4, Sox2, c-Myc, and Klf4 or Oct4, Sox2, Nanog, and Lin28 under the bFGF culture condition (Dimos et al., Science 321, 1218-1221 (2008); Lowry et al., Proc Natl Acad Sci U SA 105, 2883-2888 (2008); Nakagawa et al., Nat Biotechnol 26, 101-106 (2008); Takahashi et al., Cell 131, 861-872 (2007); Yu et al., Science 318, 1917-1920 (2007)). Such hiPSCs closely resemble the conventional hESCs and EpiSCs in the signaling requirements for self-renewal and cell morphology. Based on the rat studies, we explored whether a mESC-like pluripotency state for human pluripotent stem cells could be captured and maintained. Remarkably, we found hiPSCs could be effectively generated from IMR90 human fibroblasts by viral expression of Oct4, Sox2, Nanog, and Lin28 in the mESC medium containing hLIF with a similar timing and efficiency (FIG. 3A, 15~20 iPS cell colonies from $1 \times 10^5$ transduced cells on average) as that under the conventional condition (Yu et al., Science 318, 1917-1920 (2007)), and subsequently selected and expanded by addition of the chemical cocktail of ALK5, GSK3 and MEK inhibitors. Such hiPSCs long-term and homogenously self-renew (>20 passages) under hLIF and the chemical cocktail of PD0325901, A-83-01 and CHIR99021 (FIG. 3B). In contrast to the conventional hESCs, these hiPSCs formed ALP-positive domed colonies similar to mESCs (FIG. 3C), were resistant to MEK inhibitor and ALK5 inhibitor, and whereas the conventional hESC line H1 differentiated rapidly under the same conditions. These hiPSCs homogenously express typical pluripotency markers, such as Oct4, Sox2, Nanog, TRA-1-81, SSEA3 and SSEA-4 (FIG. 3D-3I). RT-PCR analysis of four clonal hiPSC lines under such condition confirmed the expression of the endogenous human Oct4, Sox2, Nanog, Rex-1, TDGF2 and FGF4 (FIG. 3J). By using the specific primers for transgenes, RT-PCR analysis revealed that the transduced Oct4, Sox2 and Nanog genes were largely silenced (FIG. 3J). Moreover, these hiPSCs showed similar DNA methylation patterns on Oct4 promoter as H1 human ESCs and are distinct from the parental IMR90 fibroblast (FIG. 3K). Similar to riPSCs, the inhibitor cocktail was required for maintaining the domed colony morphology and long term in vitro self-renewal of hiPSCs. Removing the inhibitor cocktail caused the cells to lose colony morphology within one passage. Removing hLIF from the medium did not show immediate/dramatic effects on the cells. However, hLIF seems to be useful for the long-term culture of hiPSCs. When cultured in the medium containing the chemical inhibitors but without hLIF, hiPSC culture deteriorates gradually and could not be homogenously passaged beyond 10 passages. Nevertheless, the exact signaling mechanism in self-renewal of such novel hiPSCs remains to be determined.

Importantly, immunocytochemistry confirmed that such novel hiPSCs could differentiate into endoderm (Albumin) (FIG. 4A), neuroectoderm (βIII-tubulin, Tuj1) (FIG. 4B) and mesoderm (brachyury) (FIG. 4C) derivatives in vitro. Furthermore, after transplanted into the SCID mice, such hiPSCs formed teratoma, which consisted of all three germ layers including neuroepithelium-like structure (ectoderm) (FIG. 4D), epithelial tube structure (endoderm) (FIG. 4D), and cartilage-like structure (mesoderm) (FIG. 4E). Taken together, the above results suggested that a mESC-like human pluripotent stem cell can be captured and long-term maintained.

Discussion

Although embryonic stem cells have been established from mice since 1981 (Martin, G. R., *Proc Natl Acad Sci USA* 78, 7634-7638 (1981)), attempts to derive their counterparts from other animals such as rat, have not completely succeeded (Demers et al., *Cloning Stem Cells* 9, 512-522 (2007); Ruhnke et al., *Stem Cells* 21, 428-436 (2003), 2003; Schulze et al., *Methods Mol Biol* 329, 45-58 (2006); Ueda et al., "Establishment of rat embryonic stem cells and making of chimera rats," *PLoS ONE* 3, e2800 (2008)). By combining the genetic reprogramming and chemical approach, we were able to generate novel mESC-like rat and human pluripotent stem cells that share key characteristics of the conventional mESCs in colony morphology and culture requirements/signaling responses. Under the unique cocktail of small molecules, our stable riPSCs were capable of extensively contributing to chimerism in vivo. Rats are more suited for physiological and behavioral studies and are excellent model for multigenic human diseases. However, the utilization of this invaluable model was hindered due to the unavailability of rat stem cells that are pluripotent in vivo. Our establishment of rat pluripotent cells and strategy of using the appropriate chemical cocktails will pave the way to generate gene-targeted rats for biomedical researches. Our hiPSCs grow more robustly and seem to represent a novel pluripotent state that is similar to the conventional mESCs and different from the conventional hESCs.

Taken together, such findings underscore the unique advantage of the chemical approach, and pinpoint the importance of inhibiting TGF-β pathway for maintaining the mESC-like pluripotent state of rat and human cells. Our studies collectively provide a framework to generate pluripotent stem cells by reprogramming or derive early ICM-stage ESCs from rats or other species, whose embryonic stem cells are still not available.

Experimental Procedures

Cell culture and viral transduction: Diploid rat WB-F344 cells (Grisham et al., *Proc Soc Exp Biol Med* 204, 270-279 (1993)), a kind gift from Prof. William B. Coleman at University of North Carolina, at passage 7 were transduced by pMXs-based retroviruses for mouse Oct4, Klf4 and Sox2 (Addgene) as described (Takahashi, K., and Yamanaka, S., *Cell* 126, 663-676 (2006)). 24 hours later, $1 \times 10^5$ transduced WB-F344 cells were seeded on the X-ray inactivated CF1 MEFs in 100 mm dish and incubated with mESC growth medium: Knockout™ DMEM, 20% Knockout serum replacement, 1% Glutamax, 1% Non-essential amino acids, 1% penicillin/streptomycin, 0.1 mM β-mercaptoethanol and $10^3$ U/ml mLIF (Millipore). After 10 days, the riPSC colonies were picked up for expansion on MEF feeder cells in mESC growth medium, and treated with MEK inhibitor PD0325901 (Stemgent, 0.5 μM), ALK5 inhibitor A-83-01 (Tocris Bioscience, 0.5 μM), and GSK3β inhibitor CHIR99021 (Stemgent, 3 μM).

Human fibroblasts IMR90 (ATCC No. CCL-186) were cultured and transduced by pSin-EF2-Puro-based lentiviruses for human Oct4, Sox2, Nanog and Lin28 (Addgene) as described (Yu et al., *Science* 318, 1917-1920 (2007)). 24 hours later, $1 \times 10^5$ transduced IMR-90 cells were seeded on the X-ray inactivated CF1 MEF feeder cells in a 100 mm dish. 24 hours later, the media was changed to mESC medium supplemented with $10^3$ U/ml hLIF (Millipore). After three weeks, the hiPSC colonies were observed and picked up at the fourth week post-infection for expansion on feeder cells in the same medium containing MEK inhibitor PD0325901 (0.5 μM), ALK5 inhibitor A-83-01 (0.25 μM), and GSK3β inhibitor CHIR99021 (3 μM).

Blastocyst Injection:

The blastocysts were recovered from the uterus of Brown-Norway (BN) females at 4.5 days post coitum. The blastocysts were placed in a drop of HEPES under mineral oil. 8~15 riPSCs were injected into the blastocyst cavity using a microinjection pipette. After injection, blastocysts were transferred to pseudo-pregnant recipient females. All animal procedures were in accordance with the guidelines of the National Institute of Health.

Supplemental Data

The Supplemental data includes the supplemental experimental procedures, one table and one figure.

Supplemental Experimental Procedures:

Differentiation of iPSCs in vitro: The in vitro differentiation of riPSCs or hiPSCs was carried out by the standard embryoid body differentiation methods. The riPSCs or hiPSCs were dissociated by 0.05% Trypsin-EDTA and cultured in ultra-low attachment 100-mm dish in DMEM medium supplemented with 10% FBS to form embryoid body (EBs). The medium was changed every another day. One week later, the EBs were harvested and transferred into Matrigel-coated 6-well plate in DMEM medium with 10% FBS. Three to seven day later, the cells were fixed for immunocytochemistry analysis. All cell culture products were from Invitrogen/Gibco BRL except where mentioned.

Cytochemistry and immunofluorescence assay: Alkaline Phosphatase staining was performed according to the manufacturer's protocol using the Alkaline Phosphatase Detection Kit (Millipore). For immunofluorescence assay, cells were fixed in 4% paraformaldehyde for 10 minutes and washed three times with PBS containing 0.1% Triton X-100 (Sigma-Aldrich). The fixed cells were then incubated in blocking buffer, 0.1% Triton X-100 and 10% normal donkey serum (Jackson ImmunoResearch Laboratories Inc) in PBS (Invitrogen/Gibco BRL), for 30 min at room temperature (RT). The cells were then incubated with primary antibody overnight at 4° C. in blocking buffer. The day after, cells were washed with PBS and incubated with secondary antibody in PBS containing 0.1% Triton X-100 for one hour at RT. Mouse anti-Oct4 antibody (1:250) (Santa Cruz Biotechnology), rabbit anti-Sox2 antibody (1:2000) (Chemicon), mouse anti-SSEA1 antibody (1:250) (Santa Cruz Biotechnology), rabbit anti-Nanog antibody (1:500) (Abcam), rat anti-SSEA3 antibody (1:1000) (Chemicon), mouse anti-SSEA4 antibody (1:1000) (Chemicon), mouse anti-TRA-1-81 antibody (1:1000) (Chemicon), rabbit anti-Pdx1 (1:1500), a gift from Dr. C. Wright (Vanderbilt University, TN), mouse anti-βIII-Tubulin (Tuj1) antibody (1:1000) (Covance Research Products), rabbit anti-albumin antibody (1:1000) (DAKO) were used as primary antibodies. Secondary antibodies were Alexa Fluor 486/555 donkey anti-mouse, anti-rat, anti-goat or anti-rabbit IgG (1:500) (Invitrogen). Nuclei were visualized by DAPI (Sigma-Aldrich) staining Images were captured using a Nikon Eclipse TE2000-U microscope.

RT-PCR analysis: RNA was extracted from riPSCs and hiPSCs using the RNeasy Plus Mini Kit in combination with QIAshredder (Qiagene). Reverse transcription was performed with 1 µg RNA using iScript™ cDNA Synthesis Kit (BioRad). Amplification of specific genes was done using primers showed in Table 1. The PCR conditions were 95° C. for 5 minutes, 94° C. for 30 seconds, annealing temperature for 30 seconds, and 72° C. for 30 seconds, 2535 cycles, and then 72° C. for 10 minutes. For Oct4 promoter methylation study using bisulfite-sequencing, DNAs from WB-F344 cells, riPSCs, IMR90, and hiPSCs were isolated using the Non Organic DNA Isolation Kit (Millipore). The DNAs were then treated with the EZ DNA Methylation-Gold Kit (Zymo Research Corp., Orange, Calif.). The treated DNAs were then used as templates to amplify sequences of interest. Primers used for Oct4 promoter fragment amplification were showed in Table 1. The resulting fragments were cloned using the TOPO TA Cloning Kit for sequencing (Invitrogen) and sequenced.

Teratoma Formation: The serially passaged riPSCs or hiPSCs were harvested by using 0.05% Trypsin-EDTA. Three to five million cells were injected under the kidney capsule of SCID mice (n=3). After 4-5 weeks, all mice developed teratomas, which were removed and then histologically analyzed.

TABLE 1

| Genes | Forward primer (SEQ ID NO:) | Reverse primer (SEQ ID NO:) | Size (bp) |
|---|---|---|---|
| | List of primers information for PCR | | |
| | For RT-RCR (rat cells) | | |
| Rat Oct4 | TACTGCCCGCCCCAGCG (2) | GCTGCTTGGCAATGCTAGT (3) | 449 |
| Rat Sox2 | AAGGCCGTGCACGCCGACGA (4) | ACCACACCATGAAGGCATTCAT (5) | 285 |
| Rat Nanog | TAGCCCTGATTCTTCTAGCA (6) | TTTGCTGCAACGGCACATAA (7) | 617 |
| Rat Rex-1 | AAATCATGACGAGGCAAGGC (8) | TGAGTTCGCTCCAACAGTCT (9) | 350 |
| Rat Klf4 | CAGACCTGGAAAGTGGTGG (10) | ACCTGTGTTGCCCGCAGCC (11) | 283 |
| Rat TDGF2 | AACACCAACAATATTTTATGTGGCC (12) | TCATTTCTAGGAAAAGGCAGATGC (13) | 511 |
| Rat FGF-4 | TGTGGTGAGCATCTTCGGAGTGG (14) | CCTTCTTGGTCCGCCCGTTCTTA (15) | 198 |
| Rat Eras | GCTGCCCCTCAGCCGACTGCTACT (16) | CACTGCCTTGTACTCCGGTAGCTG (17) | 210 |
| Transgenic Oct4 | GGGGTGGACCATCCTCTA (18) | CCTCCGCAGAACTCGTAT (19) | 271 |
| Transgenic Sox2 | CCCACCGCCCTCAAAGTA (20) | GGACCATACCATGAAGGCGTT (21) | 278 |
| Transgenic Klf4 | CCCACCGCCCTCAAAGTA (22) | GCTGGACGCAGTGTCTTCT (23) | 190 |
| GADPH | CCTTCATTGACCTCAACTAC (24) | GGAAGGCCATGCCAGTGAGC (25) | 594 |
| | For RT-RCR (human cells) | | |
| Endogenous Oct4 | AGTTTGTGCCAGGGTTTTTG (26) | ACTTCACCTTCCCTCCAACC (27) | 113 |
| Endogenous Nanog | TTTGGAAGCTGCTGGGGAAG (28) | GATGGGAGGAGGGGAGAGGA (29) | 194 |
| Endogenous Sox2 | CAAAAATGGCCATGCAGGTT (30) | AGTTGGGATCGAACAAAAGCTATT (31) | 162 |
| Rex-1 | CAGATCCTAAACAGCTCGCAGAAT (32) | GCGTACGCAAATTAAAGTCCAGA (33) | 307 |
| FGF-4 | CTACAACGCCTACGAGTCCTACA (34) | GTTGCACCAGAAAAGTCAGAGTTG (35) | 369 |
| TDGF2 | CTGCTGCCTGAATGGGGGAACCTGC (36) | GCCACGAGGTGCTCATCCATCACAAGG (37) | 242 |

TABLE 1-continued

List of primers information for PCR

| Genes | Forward primer (SEQ ID NO:) | Reverse primer (SEQ ID NO:) | Size (bp) |
|---|---|---|---|
| Transgenic Oct4 | CAGTGCCCGAAACCCACAC (38) | AGAGGAACTGCTTCCTTCACGACA (39) | 656 |
| Transgenic Sox2 | TACCTCTTCCTCCCACTCCA (40) | AGAGGAACTGCTTCCTTCACGACA (41) | 467 |
| Transgenic Nanog | CAGAAGGCCTCAGCACCTAC (42) | AGAGGAACTGCTTCCTTCACGACA (43) | 732 |
| GADPH | GTGGACCTGACCTGCCGTCT (44) | GGAGGAGTGGGTGTCGCTGT (45) | 152 |
| For bisulfate-sequencing | | | |
| Rat Oct4 | ATGGGATTTTGGAGGATTTTTAG (46) | CTCAAACCCAAATACCCCTACTT (47) | 206 |
| Human Oct4 | GGATGTTATTAAGATGAAGATAGTTGG (48) | CCTAAACTCCCCTTCAAAATCTATT (49) | 406 |

Example 3 Derivation of Rat Embryonic Stem Cells

To derive rat ES cells from blastocyst, zona pellucida-removed rat blastocysts (E4.5) are seeded on x-ray inactivated CF1 feeder cells with the Knock-out DMEM medium supplemented with 20% Knock-out serum replacement (KSR), 1% non-essential amino acid, 1000 U/ml mouse LIF, 1% Glutmax, 3 μM CHIR99021, 0.5 μM PD0325901, 0.25 μM A-83-01 (or 2 μM SB431542). After 3-5 days, the ICM derived cell clumps were dissociated by Accutase and transferred onto the new feeders. Colonies with typical ES cell morphology were picked up, dissociated with Accutase and then seeded on new feeders. The established rat ES cells were cultured with above medium and passaged about every 3 days (1:6). Both rat ES cells and riPSCs require the presence of LIF and inhibitor cocktail (CHIR99021, PD0325901, A-83-01) for long-term self-renewal. Rat ES cells and riPSCs express the pluripotent markers of mouse ES cells, such as Oct4, Sox2, Nanog and SSEA-1, etc., but not the markers, such as SSEA-3, SSEA-4, TRA-1-61 and TRA-1-81, that were expressed by conventionally-cultured human ES cells. Both rat ES cells and riPSCs express the ICM markers Rex-1 and ALP, which are not expressed in mouse EpiSCs.

Example 4 Derivation of Human and Monkey Embryonic Stem Cells

To convert human and monkey ES cells to mouse ES cell-like (early ICM) pluripotent state, human ES cells (Hues9) and Monkey ES cells (R366.4) were cultured with the DMEM/F-12 medium supplemented with 20% Knock-out serum replacement (KSR), 1% non-essential amino acid, 1% Glutmax, 10 ng/ml bFGF. When the cells get to 50% confluence, the media were switched to Advance DMEM/F-12, 1×N2, 1×B27, 1% Glutmax, 50 μg/ml BSA medium supplemented with 2 μM Lysine-Specific Demethylase 1 inhibitor (Parnate). After three days, the cells were cultured with the same medium containing 10 μg/ml human LiF, 3 μM CHIR99021, 0.5 μM PD0325901, and 2 μM SB431542, but without Parnate. Despite the extensive differentiation, the compact mouse ES cell-like colonies were visualized about one week treatment. The converted human/monkey ES cells were cultured with above medium and passaged about every 4~5 days (1:6). The cells express the pluripotent markers, such as Oct4, Sox2, Nanog, SSEA-3, SSEA-4, TRA-1-61, TRA-1-81 and also the ICM markers Rex-1 and ALP.

Example 5 Conversion of Epiblast Stem Cells to Embryonic Stem Cells by Small Molecules Conventional murine embryonic stem cells (ESCs) are derived from and represent pluripotent cells of the inner cell mass (ICM) of pre-implantation blastocysts. They can self-renew indefinitely and have the ability to give rise to all cell types in vitro, and most importantly contribute to an entire animal in vivo, including germline, when placed back into blastocysts. More recently, a different type of pluripotent cells was derived from post-implantation stage epiblasts, termed epiblast stem cells (EpiSCs) (Brons et al., Nature 448, 191-195, 2007; Tesar et al., Nature 448, 196-199, 2007). While EpiSCs can long-term self-renew and appear to be pluripotent in vitro as well as in vivo in teratoma assays, in contrast to mESCs, they are incapable of incorporating into ICM and contributing to chimerism, confirming that EpiSCs are from and represent an advanced/later developmental stage of pluripotency than ICM-derived ESCs and suggesting they could not be "reprogrammed" back into ICM-stage pluripotent cells even under the in vivo environment. Conventional human ESCs, although derived using blastocysts, seem to correspond very closely to the EpiSCs with respect to many characteristics, including some gene expression, colony morphology (i.e. flat colony) and the signaling responses in self-renewal and differentiation. EpiSCs/hESCs are also functionally and mechanistically distinct from mESCs (which have more compact and domed colony morphology) in many other ways. For example, while mESCs self-renew under leukemia inhibitory factor (LIF) and bone morphogenic protein (BMP) (Ying et al., Cell 115, 281-292, 2003), or under inhibition of MEK and/or FGFR (Ying et al., Nature 453, 519-523, 2008), EpiSCs/hESCs appear dependent on MAPK, FGF, and TGFβ/Activin/Nodal pathway activity for self-renewal, and differentiate rapidly when treated with MEK, FGFR and/or ALK4/5/7 inhibitors (Brons et al., Nature 448, 191-195, 2007; Li et al., Differentiation 75, 299-307, 2007; Peerani et al., EMBO J. 26, 4744-4755, 2007; Tesar et al., Nature 448, 196-199, 2007). In addition, in response to BMP treatment under defined differentiation conditions, mESCs differentiate toward mesoderm lineages while EpiSCs/hESCs generate trophoblasts or primitive endoderm cells (Brons et al., Nature 448, 191-195, 2007; D'Amour et al., Nat Biotechnol 23, 1534-1541, 2005; Xu et al., Nat Biotechnol 20, 1261-1264, 2002). These observations strongly support the notion that EpiSCs and hESCs are intrinsically similar, and raise an attractive hypothesis: as mESCs and EpiSCs/hESCs represent two distinct pluripotency states: the mESC-like state representing the ICM of pre-implantation blastocyst and the EpiSC-like state representing the post-implantation epiblasts, whether the epiblast state (including conventional hESCs) can be converted back to the ICM state. Because of the distinct difference in their ability to contribute to chimerism from mESCs or mEpiSCs (which would offer a definitive confirmation of functional conversion of EpiSCs to mESCs), the murine system represents an ideal platform to study such an intriguing process, and provides a basis for generating perhaps a new type of ICM/mESC-like human pluripotent cells from conventional hESCs.

Figure 6A:
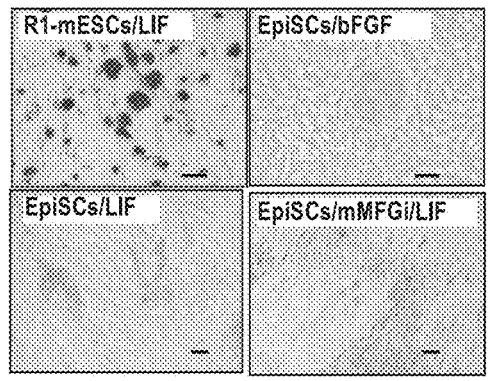
FIG. 6A-F. EpiSCs differentiate in mESC growth conditions and do not readily convert to ICM/mESC-like state. (A) Murine ESCs R1 grew as compact and domed colonies in conventional mESC growth medium supplemented with LIF, and the colonies showed positive ALP activity (top left). EpiSCs grew as large and flat colonies in conventional hESC culture medium supplemented with bFGF, and the colonies showed negative ALP activity (top right). EpiSCs differentiated in conventional mESC growth medium supplemented with LIF (bottom left); EpiSCs differentiated in conventional mESC growth medium supplemented with LIF and 0.5 µM MEK inhibitor PD0325901, 0.1 µM FGFR inhibitor PD173074 and 3 µM GSK3 inhibitor CHIR99021 (m/MFGi) (bottom right). (B) Schematic for the generation of converted cells. EpiSCs were trypsinized to single cells, and plated on feeder cells under the mESC self-renewal condition with supplements of the indicated chemical compounds for about 4 days to induce conversion, followed by another 4 days of selection. The culture was subsequently replated and further selected and expanded for another two weeks, during which time stable clones were picked. (C) Inhibition of TGFβ signaling by a selective ALK4/5/7 inhibitor A-83-01 (0.5 µM) induced EpiSCs to form more compact and domed colonies that express ALP. (D) These colonies could be further stably expanded in mESC growth medium supplemented with LIF and 0.5 µM A-83-01, 0.5 PD0325901, 0.1 µM PD173074 and 3 µM CHIR99021 (mAMFGi). (E) LSD inhibitor parnate induced EpiSCs to form more compact and domed colonies that express ALP. These colonies could be further stably expanded in mMFGi or (F) mAMFGi conditions. Note the mESC-like domed colonies and positive ALP activities. Scale bar, 50 µm.
Figure 6B:
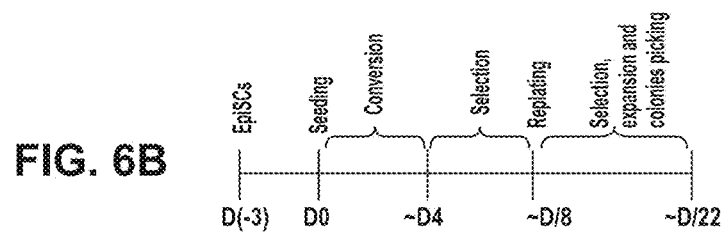

EpiSCs express master pluripotency genes, including Oct4, Sox2 and Nanog. Overexpression of Oct4, Sox2 and Klf4 has been shown to induce reprogramming of murine somatic cells to become germline-competent pluripotent cells (Nakagawa et al., Nat Biotechnol 26, 101-106, 2008). In addition, it has been shown that germline stem cells, which express fewer pluripotency genes (e.g. lack of Nanog expression), can convert to mESC-like cells in culture (Chambers et al., Nature 450, 1230-1234, 2007; Kanatsu-Shinohara et al., Cell 119, 1001-1012, 2004). Furthermore, recently a non-pluripotent cell type (called FAB-SC) was derived from blastocytes, and was shown to generate pluripotent mESC-like cells simply under LIF and BMP condition (Chou et al., Cell 135, 449-461, 2008). Moreover, recent studies suggested sub-populations of cells within mESC colonies exhibited dynamic expression of several key transcription factors (e.g. Nanog, Rex1, and Stella) that makes them fluctuate between different states continuously (e.g. between an ESC- and epiblast-like phenotypes) (Chambers et al., Nature 450, 1230-1234, 2007; Hayashi et al., Cell Stem Cell 3, 391-401, 2008; Singh et al., Stem Cells 25, 2534-2542, 2007; Toyooka et al., Development 135, 909-918, 2008). These studies raise the possibility that EpiSCs existing in a less "stable" pluripotency state than ICM-mESCs may have the ability to transition back to a mESC state "spontaneously" under culture fluctuation in vitro. To test this hypothesis, EpiSCs were trypsinized to single cells and plated under mESC self-renewal conditions, based on the notion that "converted" mESC-like cells within EpiSC colonies would be captured/selected and expanded under the conditions that promote self-renewal of mESCs but induce differentiation of EpiSCs. We found EpiSCs differentiated (e.g. cells spread/migrated out of colonies) in the first passage and no colony could be identified over several passages when they were cultured under the conventional mESC growth condition with feeder cells and supplemented with LIF (FIG. 6A). Given that the "spontaneous" conversion from EpiSCs to mESCs might be very inefficient, a stronger and more stringent differential self-renewal promoting and differentiation inducing condition might be required to select/capture and expand those "rare" converted mESC-like cells from EpiSCs (e.g. achieving cleaner phenotypic distinction and minimizing the overgrowth of differentiated EpiSCs). Based on the differential signaling responses (self-renewal vs. differentiation) between mESCs and EpiSCs in the context of FGF and MAPK signaling pathways, as well as the observation that inhibition of MEK-ERK signaling promotes reprogramming of cells towards more primitive state (Chen et al., Proc Natl Acad Sci USA 104, 10482-10487, 2007; Shi et al., Cell Stem Cell 2, 525-528, 2008; Silva et al., PLoS Biol 6, e253, 2008), we next treated EpiSCs with a combination of selective FGFR inhibitor PD173074 (0.1 µM) and MEK inhibitor PD0325901 (0.5 µM) under the regular mESC self-renewal condition. Under this 2PD/LIF condition that promotes robust clonal growth of mESCs and inhibits growth of differentiated cells, we observed accelerated differentiation of EpiSCs and decreased growth of overall cell culture. Most of cells died when kept culturing in the 2PD/LIF medium and no mESC-like colony was identified over serial passages. Similarly, adding CHIR99021 (3 µM) to the 2PD/LIF condition for improved mESC growth/survival did not promote or capture the conversion of EpiSCs to mESC-like state (FIG. 6A). These results suggested that the EpiSCs represent a "stable" pluripotency state that does not readily convert to an ESC-like state spontaneously under conditions promoting mESC self-renewal. This is also consistent with a more recent study where it was shown that conversion of EpiSCs to mESC-like state could only be achieved by overexpression of Klf4 in conjunction with using chemical inhibitors of MEK and GSK3 (Guo et al., Development 136, 1063-1069, 2009).

Figure 6C:
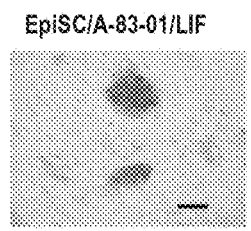
Figure 6D:
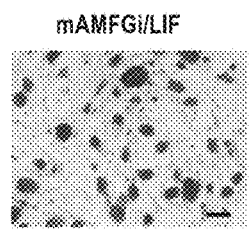
Figure 7A:
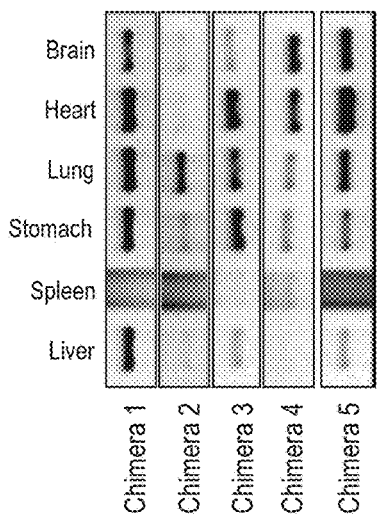
FIG. 7A-E. EpiSCs convert to ICM/mESC-like state by treatment with parnate and inhibitors of ALK4/5/7, MEK, FGFR and GSK3. (A) Efficiency in producing chimerism from three types of compound-treated cells. (B) Stable mESC-like cells converted from EpiSCs by the parnate/mAMFGi condition contributed to chimerism in adult mice after aggregated embryos were transplanted into pseudopregnant mice. The Agouti coat color originated from Parnate/mAMFGi cells. (C) PCR genotyping for the presence of GFP integration in multiple adult tissues. (D) An E13.5 embryo was examined by fluorescence for contribution from the parnate/mAMFGi cells that were labeled with GFP, and GFP-positive cells were observed in multiple tissues of the embryo (higher magnification pictures are shown in FIG. 10A). (E) GFP/SSEA-1 double positive cells in the gonad were isolated by FACS and examined by real-time PCR for germline markers. The results demonstrated the specific expression of germline markers Blimp1 and Stella in the Parnate/mAMFGi cells-contributed germline lineage. Bar: ±STDV.
Figure 7B:
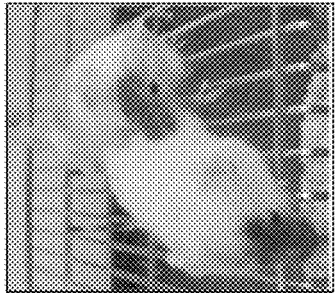
Figure 7C:
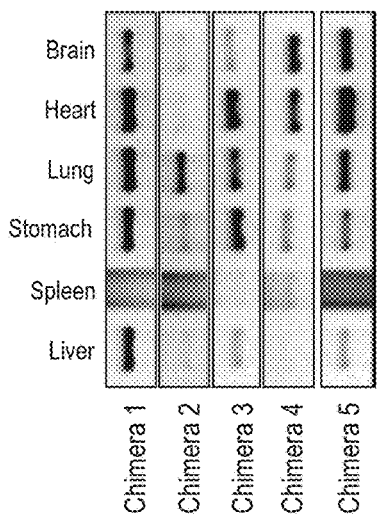
Figure 7D:

TGFβ/Activin/Nodal activity is dynamically regulated temporally and spatially during mouse embryogenesis and is required during implantation to control fate of early progenitor cells in the epiblasts (Mesnard et al., Development 133, 2497-2505, 2006). The derivation of EpiSCs requiring FGF and TGFβ/Activin/Nodal pathway activities suggests that TGFβ/Activin/Nodal provides an anti-differentiation signal for EpiSCs (Brons et al., Nature 448, 191-195, 2007; Tesar et al., Nature 448, 196-199, 2007). In addition, it was reported that E-cadherin is expressed in embryos from the one-cell-stage, and down-regulation of E-cadherin by signaling facilitates the implantation of blastocyst (Li et al., J Biol Chem 277, 46447-46455, 2002). Moreover, TGFβ/Activin/Nodal activities also promote epithelial-mesenchymal transition (EMT) by down-regulating E-cadherin during gastrulation (Derynck and Akhurst, Nat Cell Biol 9, 1000-1004, 2007; Gadue et al., Proc Natl Acad Sci USA 103, 16806-16811, 2006; Sirard et al., Genes Dev 12, 107-119, 1998). Based on these studies, we hypothesized that inhibition of TGFβ/Activin/Nodal signaling might promote the process of mesenchymal-epithelial transition (MET) and consequently the conversion of EpiSC to the mESC-like state. A-83-01 is a selective ALK4/5/7 inhibitor, which has no cross inhibitory effect on the BMP receptors (Tojo et al., Cancer Sci 96, 791-800, 2005). Consistent with the previous reports, blocking TGFβ/Activin/Nodal signaling by 0.5 µM A-83-01 induced rapid differentiation of EpiSCs under EpiSC/hESC culture condition that is supplemented with bFGF. In dramatic contrast, under mESC culture condition that is supplemented with LIF, A-83-01 induced overall population of EpiSCs to form more compact and domed colonies that resemble mESC colony morphology and express ALP (a pluripotency marker highly expressed in mESCs, but not in EpiSCs) (FIG. 6C). Another widely used specific ALK4/5/7 inhibitor SB431542 has a similar effect on EpiSCs. When the A-83-01 treated colonies were exposed to 2PD/LIF condition for selection, more than 50% of colonies could self-renew and maintain ALP activity, suggesting the cells acquired some mESC properties. Those domed ALP positive colonies were further maintained and expanded in mESC growth media supplemented with inhibitors of ALK5, MEK, FGFR and GSK3 (named mAMFGi condition). These cells can long term self-renew under the mAMFGi condition, have an indistinguishable mESC colony morphology (FIG. 6D), and express pluripotency markers such as Oct4, Nanog, SSEA-1, as well as regain the ICM marker Rex-1. However, when these cells were labeled with a constitutively active GFP by lentiviruses, and aggregated with morulas, we did not obtain chimeric animals after the resulted embryos were transplanted into mice (FIG. 7A). These results indicated that inhibition of TGFβ signaling in conjunction with inhibition of MEK, FGFR and GSK3 has strong reprogramming activity and can promote partial conversion of EpiSCs to a mESC-like state.

Figure 6E:
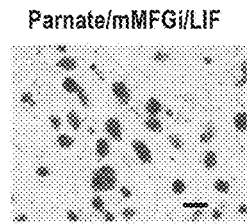
Figure 6F:
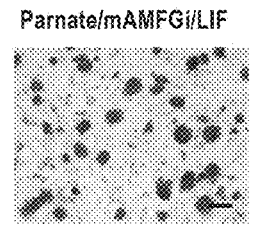
Figure 7E:
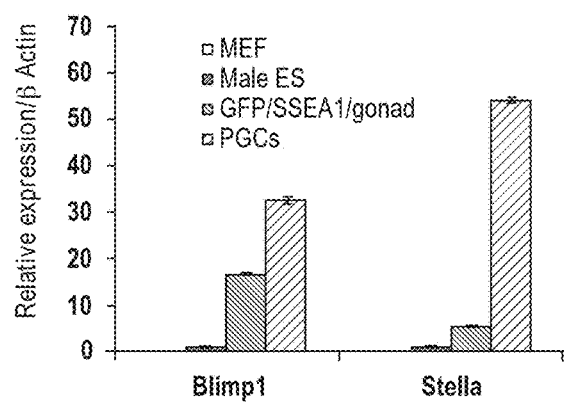

Histone modifications, such as acetylation and methylation, have been established to play important roles in gene regulation. It has been indicated that Stella is an important gene in mESC's competence to germline, and is transcriptionally silent in EpiSCs and epiblast-like cells within mESCs. Moreover, histone modification regulates the Stella expression in mESCs (Hayashi et al., Cell Stem Cell 3, 391-401, 2008; Tesar et al., Nature 448, 196-199, 2007). We hypothesized that a derepression of the silenced gene loci responsible for true in vivo pluripotency may promote EpiSCs to overcome the epigenetic restriction/threshold toward mESC-like state. Consequently, we chose the small molecule parnate, which has been shown to increase global H3K4 methylation by inhibiting the histone demethylase LSD1 that specifically demethylates mono- and di-methylated histone H3K4 (Lee et al., Chem Biol 13, 563-567, 2006). Remarkably, after four days of 2 µM parnate treatment, up to 70-80% of the EpiSCs formed small and compact colonies in the mESC growth condition. When the parnate-treated cells were then selected with 2PD/LIF, roughly 20% of cells survived the selection as domed and ALP positive colonies. Those colonies were further expanded with inhibitors of MEK, FGFR and GSK3 (named mMFGi condition) or with the mAMFGi condition. Both conditions resulted in a stable cell culture (>80 passages over 8 months), that is morphologically indistinguishable from mESCs (FIG. 6E, F). We next examined GFP-labeled parnate/mMFGi cells and parnate/mAMFGi cells in vivo by morula aggregation and transplantation of resulted embryos. Remarkably, we obtained 7 (out of 9 born pups) adult chimeras from parnate/mAMFGi cells as determined by coat color and PCR genotyping for the presence of GFP integration in multiple adult tissues (FIG. 7A, B, C). Consistently, widespread GFP positive cells were observed in multiple tissues (i.e. three germ layers, including gonad) of E13.5 embryos from transplantation of the parnate/mAMFGi cell-aggregated morulas (FIG. 7A, D, 10A). To examine germline contribution from parnate/mAMFGi cells, the GFP/SSEA-1 double positive cells from the gonad were isolated by FACS and confirmed to express germ line markers Blimp1 and Stella by real-time PCR (FIG. 7E). These data suggest that parnate/mAMFGi cells converted from EpiSCs regain true in vivo pluripotency. In contrast, GFP-positive cells were only found in the yolk sac of E13.5 embryos recovered from transplantation of parnate/mMFGi cell-aggregated morulas (FIG. 7A).

Figure 8A:
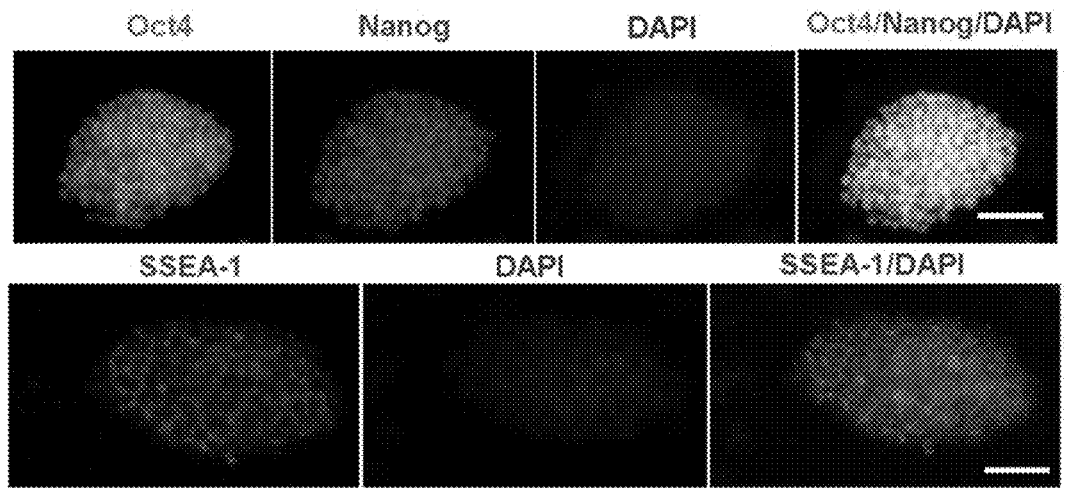
Figure 8B:
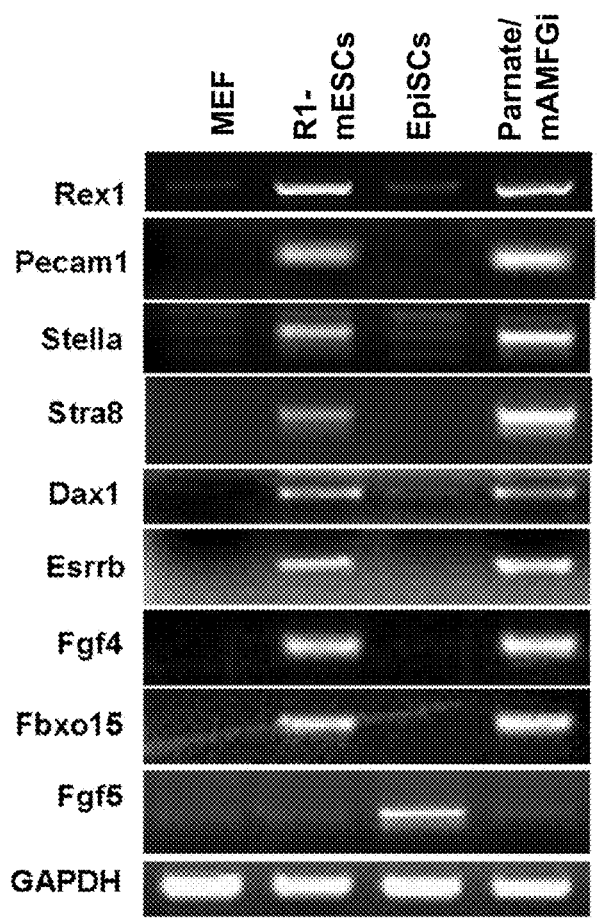
Figure 9B:
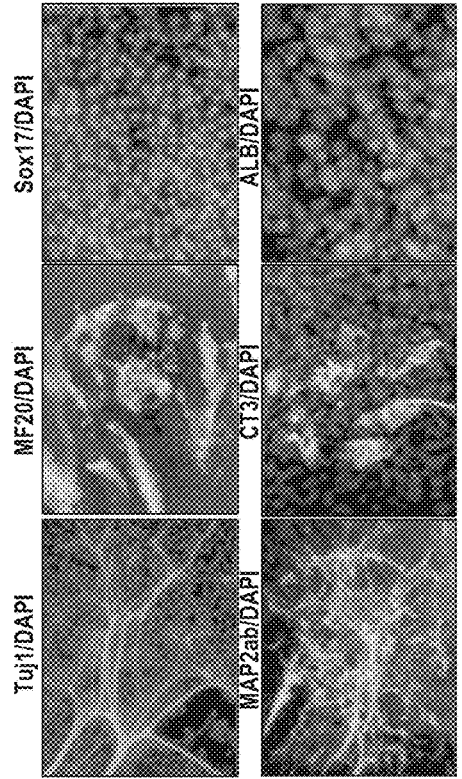
FIG. 9A-D. Functional characterizations of the converted Parnate/mAMFGi cells. (A) Parnate/mAMFGi cells have similar growth rate as mESCs. R1-mESCs and Parnate/mAMFGi cells were passaged every 3 days, and cell number was counted every 24 hr. (B) Parnate/mAMFGi cells can effectively differentiate in vitro into cells in the three germ layers, including characteristic neuronal cells (βIII-tubulin and MAP2ab positive), cardiomyocytes (cardiac troponin and MHC positive), and endoderm cells (Sox17 or Albumin positive). Nuclei were stained with DAPI. (C) BMP4 has differential effect on induction of mesoderm marker (Brachyury), trophoblast marker (Cdx2), and primitive endoderm marker (Gata6) expression in EpiSCs, mESCs, and parnate/mAMFGi cells. (D) Directed step-wise cardiomyocyte differentiation under a monolayer and chemically defined condition demonstrated that Parnate/mAMFGi cells share similar differentiation response as R1-mESCs, and are different from EpiSCs. Cells were characterized with CT3 staining and beating phenotype.
Figure 9D:
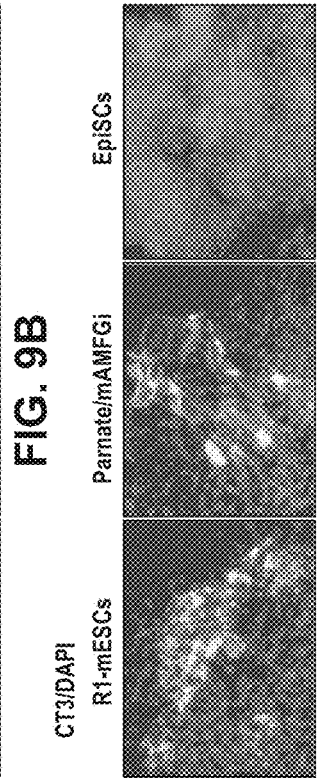
Figure 9A:
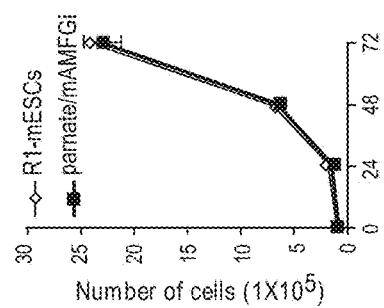
Figure 9C:
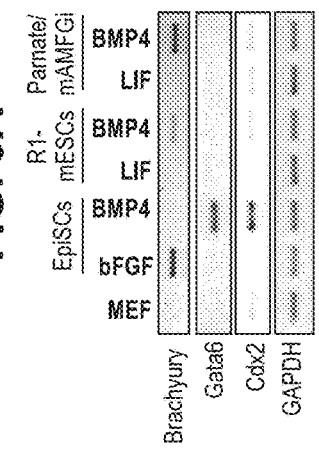
Figures 10A, 10B:
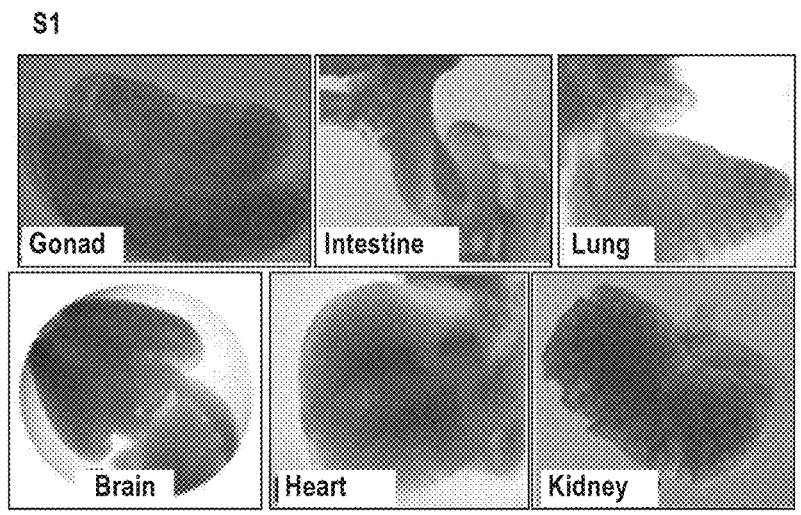
FIG. 10A-B. Parnate/mAMFGi cells contributed to chimeric mice efficiently. (A) Tissues from chimeric embryos. GFP positive cells contributed from Parnate/mAMFGi cells were observed in gonad, brain, heart, intestine, lung, and kidney. (B) GFP genotyping of chimeric adult mice. Five mice were randomly picked, and GFP integration in five different tissues, namely heart, lung, liver, brain, and spleen, were analyzed by genomic PCR. Positive detection of GFP integration in all five tissues of 2 adult mice, in four tissues of 3 mice, confirmed that parnate/mAMFGi cells could contribute to the three germ layers (mesoderm, endoderm and ectoderm) in vivo.
Figure 11A:
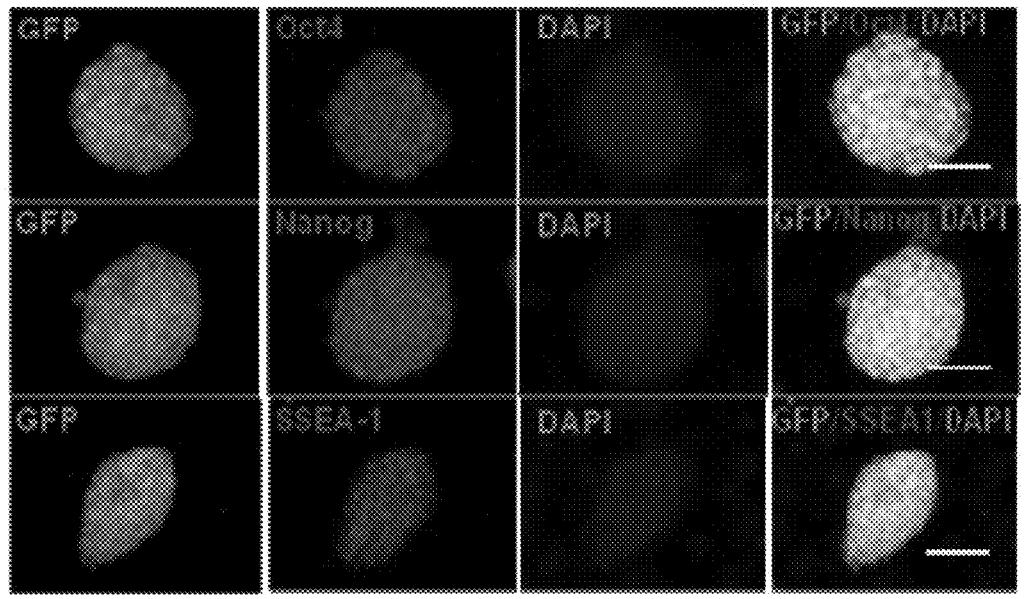
FIG. 11A-B. Homogenous expression of pluripotency markers in converted parnate/mAMFGi cells under feeder cells or feeder-free culture conditions. (A) The parnate/mAMFGi cells were labeled with GFP, and were propagated on feeders. Immunostaining results showed homogeneous expression of GFP and pluripotency-markers Oct4 (Red), Nanog (Red), and SSEA-1 (Red). (B) Left panel: Undifferentiated Oct4-positive colonies developed from single parnate/mAMFGi cells as efficiently as from single OG2-ES cells. The colonies were expanded for several passages after single cell seeding in a feeder-free and N2B27-chemically defined condition. Scale bar, 50 µm. Right panel: Parnate/mAMFGi cells differentiated and lost Oct4 expression in the absence of LIF. Parnate/mAMFGi cells were expanded after single cells seeding in a feeder-free and N2B27-chemically defined condition; the growth factor supplement was indicated.
Figure 12:
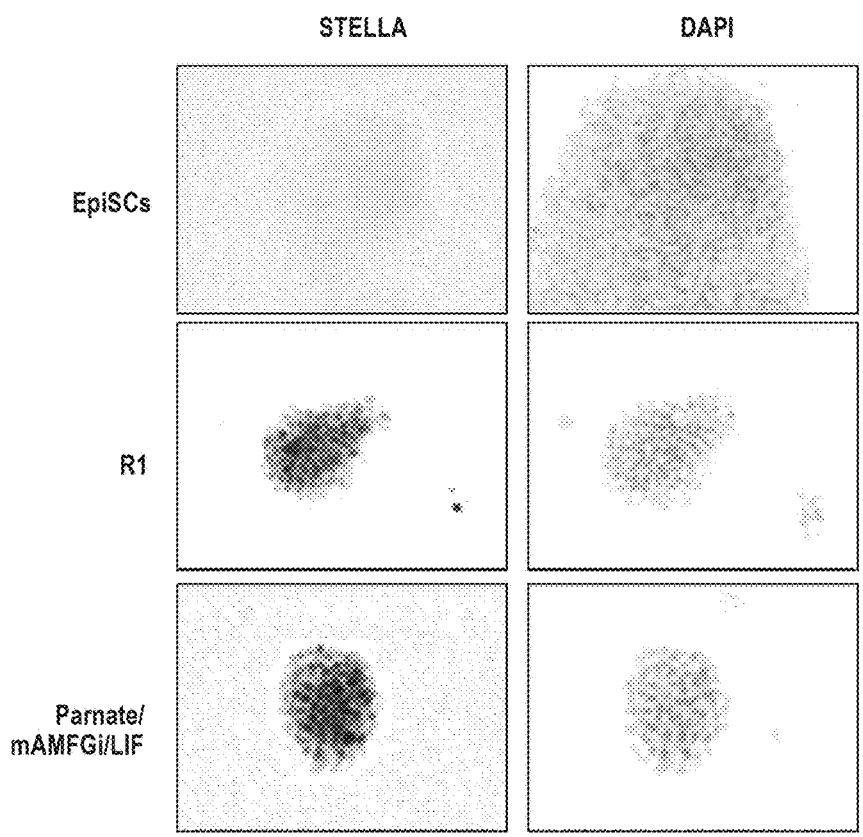
FIG. 12. Expression of STELLA was detected in converted parnate/mAMFGi cells and R1-mESC cells, but not in EpiSCs Immunostaining results showed the expression of STELLA, and DAPI.

The parnate/mAMFGi cells were therefore further characterized. Immunocytochemistry confirmed homogeneous expression of pluripotency-associated markers in long-term expanded parnate/mAMFGi cells, including Oct4, Nanog, SSEA1, and STELLA (FIG. 8A, 11A, 12). In addition, semi-quantitative RT-PCR analysis demonstrated restoration of gene expression of specific ICM and germline-competence markers (that are expressed in mESCs, but absent in EpiSCs) in parnate/mAMFGi cells, including Rex1, Pecam1, Stella, Stra8, Dax1, Fbxo15, Esrrb, and Fgf4 (FIG. 8B). In contrast, transcripts of genes associated with the epiblast and early germ layers such as Fgf5 and Brachyury (T) were decreased or undetectable in parnate/mAMFGi cells (FIG. 8B, 9C). Furthermore, transcriptome analysis by microarray demonstrated that the converted parnate/mAMFGi cells are much more similar to mESCs (Pearson correlation value: 0.87), while the original EpiSCs are more distant from mESCs (Pearson correlation value: 0.74) (FIG. 8C), consistent with previous reports. To further analyze specific epigenetic changes associated with the conversion, we examined the promoter DNA methylation of Stella and Fgf4, whose expressions are closely associated with ICM properties (Hayashi et al., Cell Stem Cell 3, 391-401, 2008; Imamura et al., BMC Dev Biol 6, 34, 2006), using bisulphite genomic sequencing. It revealed that the promoter regions of Stella and Fgf4 were largely unmethylated in parnate/mAMFGi cells and mESCs, but were hypermethylated in EpiSCs (FIG. 8D). To further examine the epigenetic state of Stella, which is restricted to the mESC-like state, we performed a ChIP-QPCR analysis of its promoter region in EpiSCs, converted parnate/mAMFGi cells, and mESCs. We found that the H3K4 and H3K27 methylation pattern of Stella in parnate/mAMFGi cells is similar to that observed in mESCs, but is distinct from that in EpiSCs, confirming that the epigenetic status of Stella in the converted parnate/mAMFGi cells was switched to the mESC-like status (FIG. 8E).

Figure 11B:
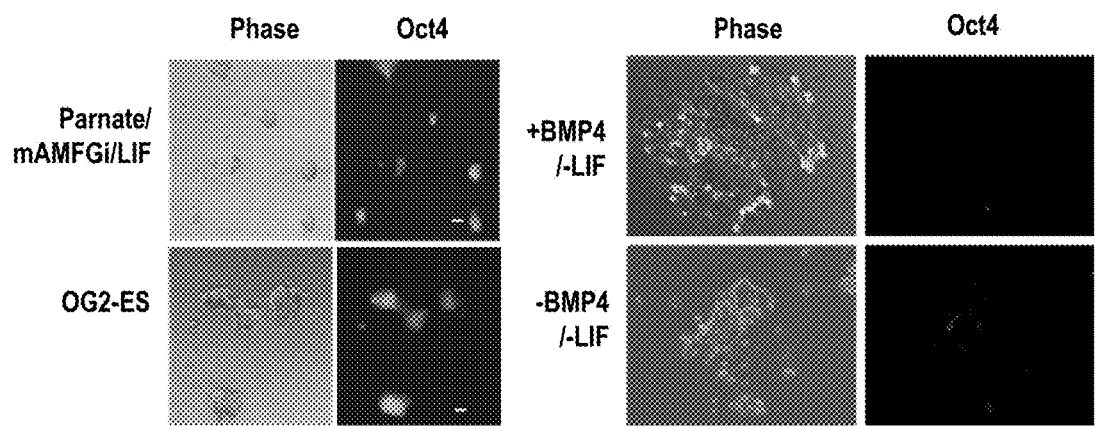

Parnate/mAMFGi cells were also examined for their in vitro functional properties. They were found to have similar growth rate as mESCs (FIG. 9A). When Parnate/mAMFGi cells were differentiated through embryoid bodies in suspension, they were able to effectively generate cell derivatives in the three primary germ layers as shown by immunocytochemistry, including characteristic neuronal cells (βIII-tubulin and MAP2ab positive), beating cardiomyocytes (cardiac troponin and MHC positive), and endoderm cells (Sox17 or Albumin positive) (FIG. 9B. Because mESCs and EpiSCs/hESCs have different responses to signaling inputs (e.g. growth factors) in self-renewal and differentiation, conditions that were developed and work effectively for mESC differentiation may often be inefficient in inducing corresponding differentiation of EpiSCs/hESCs. One of the advantages for converting EpiSC/hESC to a mESC-like state is that differentiation conditions may be more readily translated from mESC work to EpiSC/hESC work. Differential response to BMP4 treatment represents a functional assay to distinguish between mESCs and EpiSCs. Consistent with the previous studies (Beddington and Robertson, Development 105, 733-737, 1989; Czyz and Wobus, Differentiation 68, 167-174, 2001; Qi et al., Proc Natl Acad Sci USA 101, 6027-6032, 2004; Winnier et al., Genes Dev 9, 2105-2116, 1995), we found that parnate/mAMFGi cells were induced to express the mesoderm specific marker gene Brachyury (T) when treated with BMP4 as mESCs, but under the same condition couldn't give rise to trophectoderm (no induction of trophoblast marker Cdx2) or primitive endoderm cells (Gata6) as EpiSCs, suggesting a similar in vitro differentiation potential/response of parnate/mAMFGi cells to mESCs (FIG. 9C). To further demonstrate this, we attempted and compared EpiSCs, converted parnate/mAMFGi cells, and mESCs in a monolayer chemically defined directed step-wise cardiac differentiation process. In this multi-step process, where BMP activity plays an essential role in the early steps of mesoderm differentiation, we found that parnate/mAMFGi cells differentiated into beating cardiomyocytes as efficiently as mESCs, but differentiation of EpiSCs under the same condition hardly produced cells that expressed appropriate cardiac markers or have characteristic beating phenotype (FIG. 9D), confirming again that parnate/mAMFGi cells are functionally similar to mESCs. Moreover, a single cell survival assay also demonstrated that parnate/mAMFGi cells clonally expand as Oct4-positive colonies as efficiently as mESCs in feeder-free and N2/B27-chemically defined conditions, while EpiSCs survive poorly from single cells under the same condition (FIG. 11B). These data further demonstrated that EpiSCs could be functionally converted to the mESC-like state by pharmacological manipulation that targets epigenetic modifications and differential signaling pathways required by mESCs or EpiSCs.

Concurrent with our studies, EpiSC cells have recently been reported to convert to a mESC-like state by overexpression of reprogramming genes (i.e. Klf4) in conjunction with chemical compounds (Guo et al., Development 136, 1063-1069, 2009). In this study, we devised a chemically defined treatment to convert stable EpiSCs to a mESC-like, developmentally earlier pluripotency state without any genetic manipulation. Despite studies providing evidence that epiblast-like cells exist and transition back and forth within colony of conventional mESCs (Hayashi et al., Cell Stem Cell 3, 391-401, 2008); mESCs and EpiSCs share substantial set of pluripotency transcriptional factors, including Oct4, Sox2 and Nanog; and mESCs are more stable in culture, in the present study we found that EpiSCs differentiated rapidly under the conventional mESC culture conditions and no "spontaneously" converted mESC could be readily identified and isolated over serial passages at the population or clonal level. Remarkably, we found that blockage of the TGFβ pathway or inhibition of the H3K4 demethylase LSD1 with small molecule inhibitors induced dramatic morphological changes of EpiSCs towards mESC-like phenotypes with activation of some ICM-specific gene expression. However, full conversion of EpiSCs to a mESC-like state with competence to chimeric contribution can only be readily generated with a combination of inhibitors of LSD1, ALK5, MEK, FGFR, and GSK3. These observations underscore a powerful and direct induction of reprogramming from the developmentally later-stage EpiSCs to the ICM-stage mESCs by a synergy of signaling and direct epigenetic modulations. It also highlights a significant role for TGFβ pathway inhibition in promoting reprogramming and sustaining true pluripotency, which further supports our recent studies in generating chimerism-competent rat pluripotent cells (Li et al., Cell Stem Cell 4, 16-19, 2009). Collectively, our studies provide a proof-of-concept demonstration that pluripotency-restricted EpiSCs can be readily converted to a mESC-like state in the absence of any genetic manipulation by precise pharmacological control of signaling pathways that distinguish the two pluripotency states and an epigenetic target simultaneously, and offer a convenient experimental system to further study the mechanism. Such method and concept may also provide an avenue for generating a new type of mESC-like human pluripotent cell.

Experimental Procedures

Cell Culture:

The murine EpiSC line was a gift from Dr. Paul Tesar (Case Western Reserve University). EpiSCs (line EpiSC-5, male) were maintained on irradiated CF1 MEFs in human ESC medium supplemented with 10 ng/ml bFGF as described previously (Tesar et al., Nature 448, 196-199, 2007). EpiSCs were passaged every 3-4 days with 1 mg/ml collagenase type IV (Invitrogen). The R1 mESCs were cultured on irradiated CF1 MEFs with conventional mESC growth media, which consist of Knockout DMEM (Invitrogen) supplemented with 20% KSR (Invitrogen), 0.1 mM 2-ME (Sigma-Aldrich), 2 mM L-glutamine (Invitrogen), 0.1 mM NEAA (Invitrogen), and $10^3$ units/ml recombinant murine leukemia inhibitory factor (LIF) (ESGRO, Millipore). The mESCs and converted cells were passaged every 3 days as a single cell suspension using 0.05% trypsin/EDTA and seeded at $1.0 \times 10^4$ cells per $cm^2$ for routine culture. For feeder-free culture, cells are grown on gelatin-coated tissue culture dishes in chemically defined media, which consist of Knockout DMEM supplemented with 1×N2 (Invitrogen), 1×B27 (Invitrogen), 0.1 mM 2-ME, 2 mM L-glutamine, 0.1 mM NEAA, 50 µg/ml BSA fraction V (GIBCO), $10^3$ units/ml LIF and 10 ng/ml BMP4 (R&D). For growth curve experiment, cells were cultured in the feeder-free condition in gelatin-coated 12-well plates. Duplicate samples of cells were plated at a density of $1 \times 10^5$ cells per well. For each time point (24 hr apart), cells from duplicate wells were trypsinized and counted using hemocytometer. Those counts were averaged, and plotted. ALK inhibitor A-83-01, SB431542, MEK inhibitor PD0325901, GSK3 inhibitor CHIR99021, and FGF receptor inhibitor PD173074 were purchased from Stemgent Inc. Parnate was purchased from Sigma (P8511).

Semi-Quantitative RT-PCR and Real-Time PCR:

Total RNA were extracted by using RNeasy plus mini kit (Qiagen), reverse transcribed with iScript cDNA Synthesis Kit (Bio-Rad) using oligo dT primers according to manufacturer instructions. PCR products were resolved on (1.5%) agarose gels and visualized by ethidium bromide staining. Images were taken using Bio-Rad Gel document system. Diluted cDNA was used in each of duplicate quantitative PCRs on a Bio-Rad real-time PCR detection system with IQ SYBR Green (Bio-Rad). Primers used are listed in Supplemental Table 2.

Bisulfite Sequencing Analysis:

DNAs from R1 mESCs, EpiSCs, and Parnate/mAMFGi cells were isolated using the Non Organic DNA Isolation Kit (Millipore). The DNAs were then treated for bisulfate sequencing with the EZ DNA Methylation-Gold Kit (Zymo Research Corp., Orange, Calif.). The treated DNAs were then used to amplify sequences of interest. Primers used for promoter fragment amplification were as previously published (Hayashi et al., Cell Stem Cell 3, 391-401, 2008; Imamura et al., BMC Dev Biol 6, 34, 2006) and listed in Supplemental Table 2. The resulting fragments were cloned using the TOPO TA Cloning Kit for sequencing (Invitrogen) and sequenced.

Flow Cytometry and Cell Sorting:

Adherent cells were washed twice in PBS and then incubated for 20 minutes at 37° C. in Cell Dissociation Buffer (Invitrogen). Cells were dissociated and re-suspended in PBS+3% normal goat serum (blocking buffer). Cells were incubated for 40 minutes at 4° C. with antibody anti-SSEA1 (1:50, Santa Cruz) and then incubated with the corresponding secondary antibody followed by washing steps. Cells were analyzed and sorted using a FACSAria cell sorter and FACSDiva software (BD Biosciences). Using a 488-nm laser for excitation, GFP positivity was determined according to fluorescence intensity in the GFP channel. SSEA-1 positivity was determined according to fluorescence in the red channel.

In Vitro Differentiation:

Parnate/mAMFGi cells were trypsinized into single cells and cultured in suspension to form embryoid bodies/EBs in low adhesion plates (Corning) in DMEM medium supplemented with 10% FBS. Media were refreshed every other day and EBs were allowed to grow for 6 days in suspension. EBs were then replated onto 0.1% gelatin-coated plates. Spontaneous differentiations were examined by immunostaining of representative lineage specific markers with indicated antibodies at various time points (3 up to 16 days). For directed cardiac differentiation, cells were plated on Matrigel coated plates at $2\times10^4/cm^2$. 24 hours after plating, cells are switched into chemically defined medium (CDM) [consisting of RPMI 1640, 0.5×N2, 1×B27 (without Vitamin A), 0.5× Glutamax, 0.55 mM beta-mercaptoethanol, and 1× non-essential amino acids], and treated with 3 µM BIO (Calbiochem) and 20 ng/ml BMP-4 (R&D) for five days. Then, the medium is changed to CDM containing 100 ng/ml Dkk-1 and cells are cultured for additional five days. At Day 11, cells are briefly trypsinized/detached (0.05% trypsin) and replated onto gelatin coated 6-well plates in CDM with no additional growth factors, and cultured for additional 4-6 days when beating phenotype appears in most of cardiac colonies.

Characterization Assays:

ALP staining was performed using the Alkaline Phosphatase Detection Kit (Chemicon) as instructed by the manufacturer. Immunocytochemistry was performed using standard protocol. Briefly, cells were fixed in 4% paraformaldehyde (Sigma-Aldrich), washed three times by PBS, and then incubated in PBS containing 0.3% TritonX-100 (Sigma-Aldrich) and 5% normal donkey serum (Jackson Immuno Research) for 1 hr at room temperature. The cells were then incubated with primary antibody at 4° C. overnight: Albumin (Abcam, AB19188, 1:200); Brachyury (Santa Cruz, C-19, 1:200); Cardiac troponin t antibody (CT3) (Developmental Studies Hybridoma Bank, 1:700); MAP2ab (Abcam, ab5392, 1:1000); MF20 (Developmental Studies Hybridoma Bank, 1:200); Nanog (Abcam, ab21603, 1:500); Oct4 (Santa Cruz, sc-5279, 1:100); Sox17 (R&D systems, AF1924, 1:300); SSEA1 (Santa Cruz, sc-21702, 1:100); Stella (Millipore, MAB4388, 1:200); Tuj-1 (Covance, MMS-435P, 1:1000). After washing three times with PBS, cells were incubated with appropriate Alexa Fluor conjugated secondary antibodies (Invitrogen) for 2 hr at RT. Nuclei were detected by DAPI (Sigma) staining. Images were captured by Zeiss HXP 120.

Chimera Formation:

The converted cells were stably marked by GFP using lentiviruses. Cells were aggregated with 8-cell-stage mouse embryos, and were then transplanted into the uteri of 2.5 dpc pseudo-pregnant CD1 mice.

Microarray Analysis:

The Illumina Sentrix BeadChip Array MouseRef-8 v2 (Illumina, Calif., USA) was used for microarray hybridizations to examine the global gene expression of murine ES cells, EpiSCs cells and Parnate/mAMFGi cells. Biotin-16-UTP-labeled cRNA was synthesized from 500 ng total RNA with the Illumina TotalPrep RNA amplification kit (Ambion AMIL1791, Foster City, Calif., USA). The hybridization mix containing 750 ng of labeled amplified cRNA was prepared according to the Illumina BeadStation 500× System Manual (Illumina, San Diego, Calif., USA) using the supplied reagents and GE Healthcare Streptavidin-Cy3 staining solution. Hybridization to the Illumina Array MouseRef-8 v2 was for 18 h at 55° C. on a BeadChip Hyb Wheel. The array was scanned using the Illumina BeadArray Reader. All samples were prepared in two biological replicates. Processing and analysis of the microarray data were performed with the Illumina BeadStudio software. The microarray data of R1-mESC cells was from our previous studies GEO DataSet (GSM402334 and GSM402335). All raw data were subtracted for background and normalized together using the rank invariant option. We have deposited the microarray data of parnate/mAMFGi and EpiSCs to GEO DataSets with the accession number (GSM402334 and GSM402335 for R1 mouse ES cells; GSE17664 for parnate/mAMFGi and EpiSCs).

Real-Time PCR for Chromatin Immunoprecipitation (ChIP-qPCR):

ChIP was performed using a commercially available Magna ChIP™ G kit (catalog #17-611, Millipore). Briefly, feeder-free cultured $1\times10^6$ cells were fixed with 1% formaldehyde, lysed, and sonicated to obtain 200-500 bp DNA fragments conjugated with nucleosomes. The sonicated lysates were immunoprecipitated with anti-trimethyl-histone H3 lysine 4 (Millipore, Cat. #17-614, 3 ul/reaction) or anti-trimethyl-histone H3 lysine 27 (Millipore, Cat. #17-622, 4 µg/reaction) that were in advance reacted with secondary antibodies conjugated with magnetic beads. After incubation with each antibody for 24 hr, immunoprecipitants were recovered and DNA fragments contained were purified by incubation with Proteinase K. The DNA fragments were subjected to real-time PCR. Whole-cell lysates before incubation with antibodies were used as input. One microliter of DNA fragments from whole lysates and immunoprecipitants were subject to real-time PCR reaction. Immunoprecipitants with normal Rabbit IgG served as negative control samples and showed no detectable background. Primer sequences were listed in Table 2.

TABLE 2

Primers used for PCR

| Gene | Forward (SEQ ID NO:) | Reverse (SEQ ID NO:) |
|---|---|---|
| For RT-PCR | | |
| Blimp1 | TCAGCCTCTTCCCTAGGTTGTATC (50) | AATCTTAAGGATCCATCGGTTCAAC (51) |
| Brachyury | ATGCCAAAGAAAGAAACGAC (52) | AGAGGCTGTAGAACATGATT (53) |
| Cdx2 | AGGCTGAGCCATGAGGAGTA (54) | CGAGGTCCATAATTCCACTCA (55) |
| Dax1 | GTGGCAGGGCAGCATCCTCTACAA (56) | CAAAAGAAGCGGTACA (57) |
| Esrrb | CGC CAT CAA ATG CGA GTA CAT GC (58) | GAATCACCATCCAGGCAC TCTG (59) |
| Fbxo15/ECAT3 | TAGATTCTTGGACTTCCGTTCA (60) | ACCAAGGTCACCGCATCCAA (61) |

TABLE 2 -continued

Primers used for PCR

| Gene | Forward (SEQ ID NO:) | Reverse (SEQ ID NO:) |
|---|---|---|
| Fgf4 | CGTGGTGAGCATCTTCGGAGTGG (62) | CCTTCTTGGTCCGCCCGTTCTTA (63) |
| Fgf5 | CTGTACTGCAGAGTGGGCATCGG (64) | GACTTCTGCGAGGCTGCGACAGG (65) |
| GAPDH | GTGTTCCTACCCCCAATGTGT (66) | ATTGTCATACCAGGAAATGAGCTT (67) |
| Gata6 | ACCTTATGGCGTAGAAATGCTGAGGGTG (68) | CTGAATACTTGAGGTCACTGTTCTCGGG (69) |
| Pecam1 | GTCATGGCCATGGTCGAGTA (70) | AGCAGGACAGGTCCAACAAC (71) |
| Rex-1 | TGAAAGTGAGATTAGCCCCGAG (72) | GTCCCATCCCCTTCAATAGCAC (73) |
| Stella | GAAACTCCTCAGAAGAAA (74) | CTCTTGTTCTCCACAGGTAC (75) |
| Stra8 | GCAACCAACCCAGTGATGATGG (76) | CATCTGGTCCAACAGCCTCAG (77) |

For bisulfite-sequencing PCR

| Fgf4 | TTTAGGTTTTAAGAGTGTTGGGGAGAAGAT (78) | TACAAAACAAAAACATCAAACCCATTCTAA (79) |
|---|---|---|
| Stella | ATTTTGTGATTAGGGTTGGTTTAGAA (80) | CCAAAACATCCTCTTCATCTTTCTTCT (81) |
| Stella nest | TTTTTGGAATTGGTTGGGATTG (82) | CTTCTAAAAAATTTCAAAATCCTTCATT (83) |

For ChIP-Q PCR

| Stella | GATCCAGCTGGTCTGAGCTA (84) | GTGCAGGGATCATAGGAGTG (85) |
|---|---|---|

Example 6 Characterization of Pluripotent Animal Cell that Replicates and Maintains Pluripotency To characterize the newly generated hiPSCs, real-time PCR was employed to analyze the gene expression of hiPSCs. Human ES cell line, Hues9 (hES facility, Harvard University, http://mcb.harvard.edu/melton/hues/), was used as a control. Real-time PCR analysis reveal that, as compared to Hues9 cells, hiPSCs of the present invention express certain genes at higher levels, such as Gbx2 (5-fold), Dppa3 (2-fold) and Klf4 (2.5-fold). These markers are also found to be highly expressed in mouse ES cells, but not in mouse EpiSCs. The primers used in the real-time PCR assay are: Dppa3: 5'-CAACCTACATCCCAGGGTCT-3' (SEQ ID NO:86); 5'-TCAACGTCTCGGAGGAGATT-3' (SEQ ID NO:87); Gbx2: 5'-AAAGGCTTCCTGGCCAAAG-3' (SEQ ID NO:88); 5'-TTGACTCGTCTTTCCCTTGC-3' (SEQ ID NO:89); Klf4: 5'-AGCCTAAATGATGGTGCTTGGT-3' (SEQ ID NO:90); 5'-TTGAAAACTTTGGCTTCCTTGTT-3' (SEQ ID NO:91).

Using western-blot analysis, we have also analyze the expression of E-cadherin in hiPSCs. The expression of E-cadherin in hiPSCs is twice that of Hues9 human ES cells.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A method of culturing pluripotent cells through at least one cell division, the method comprising,
   culturing pluripotent animal cells in the presence of a sufficient amount of:
   (a) a compound selected from one or more of a MEK inhibitor, an Erk inhibitor, a p38 inhibitor, and an FGF receptor inhibitor;
   (b) a GSK3β inhibitor; and
   (c) nutrients;
   to allow for at least one cell division while maintaining cell pluripotency.

2. The method of claim 1, wherein the culturing step further comprises culturing the cells in the presence of a Leukemia inhibitory factor (LIF).

3. The method of claim 1, wherein the GSK3β inhibitor is CHIR99021.

4. The method of claim 1, wherein the compound is a MEK inhibitor.

5. The method of claim 4, wherein the MEK inhibitor is PD0325901.

6. The method of claim 1, wherein the pluripotent cells are cultured through at least five cell divisions while maintaining cell pluripotency.

7. The method of claim 1, further comprising introducing a heterologous nucleic acid into the pluripotent cells and culturing the resulting cells to allow for at least one additional cell division while maintaining pluripotency.

8. The method of claim 1, wherein the pluripotent cells are rat, human, non-human primate, ovine, bovine, feline, canine, or porcine cells.

9. A method of producing non-human chimeric animal progeny comprising culturing non-human pluripotent cells by the method of claim 1 and introducing the non-human pluripotent cell into a blastocyst, wherein the blastocyst is from the same species of animal as the non-human pluripotent cells, and introducing the blastocyst into the uterus of an animal of the same species as the non-human pluripotent cells.

10. A culture of pluripotent mammalian cells, comprising a sufficient amount of:
    (a) a compound selected from one or more of a MEK inhibitor and an FGF receptor inhibitor; and
    (b) a GSK3β inhibitor;
    to allow for at least one cell division while maintaining cell pluripotency.

11. The culture of claim 10, further comprising Leukemia inhibitory factor (LIF).

12. The culture of claim 10, wherein the GSK3β inhibitor is CHIR99021.

13. The culture of claim 10, wherein the compound is a MEK inhibitor.

14. The culture of claim 13, wherein the MEK inhibitor is PD0325901.

15. The culture of claim 10, wherein the pluripotent mammalian cells are human cells or rat cells.

16. The culture of claim 10, wherein the pluripotent mammalian cells are embryonic stem cells.

17. A cell culture medium, comprising a sufficient amount of:
    (a) a compound selected from one or more of a MEK inhibitor and an FGF receptor inhibitor; and
    (b) a GSK3β inhibitor;
    to allow for at least one cell division while maintaining cell pluripotency when pluripotent cells are cultured in the medium.

18. The cell culture medium of claim 17, further comprising Leukemia inhibitory factor (LIF).

19. The cell culture medium of claim 17, wherein the medium is in a pre-packaged, sealed container.

20. The cell culture medium of claim 17, wherein the GSK3β inhibitor is CHIR99021.

21. The cell culture medium of claim 17, wherein the compound is a MEK inhibitor.

22. The cell culture medium of claim 21, wherein the MEK inhibitor is PD0325901.

* * * * *